United States Patent
Lee et al.

(10) Patent No.: US 11,564,615 B2
(45) Date of Patent: Jan. 31, 2023

(54) METHOD AND SYSTEMS FOR ANALYZING FUNCTIONAL IMAGING DATA

(71) Applicant: The Board of Trustees of the Leland Stanford Junior University, Stanford, CA (US)

(72) Inventors: Jin Hyung Lee, Stanford, CA (US); David Bernal-Casas, East Palo Alto, CA (US)

(73) Assignees: The Board of Trastees of the Leland, Stanford, CA (US); Stanford Junior University, Stanford, CA (US)

( * ) Notice: Subject to any disclaimer, the term of this patent is extended or adjusted under 35 U.S.C. 154(b) by 1226 days.

(21) Appl. No.: 16/072,476

(22) PCT Filed: Jan. 30, 2017

(86) PCT No.: PCT/US2017/015659
§ 371 (c)(1),
(2) Date: Jul. 24, 2018

(87) PCT Pub. No.: WO2017/136285
PCT Pub. Date: Aug. 10, 2017

(65) Prior Publication Data
US 2018/0368720 A1 Dec. 27, 2018

Related U.S. Application Data

(60) Provisional application No. 62/289,741, filed on Feb. 1, 2016.

(51) Int. Cl.
*A61B 5/377* (2021.01)
*A61B 5/055* (2006.01)
(Continued)

(52) U.S. Cl.
CPC .............. *A61B 5/377* (2021.01); *A61B 5/055* (2013.01); *A61B 5/246* (2021.01); *A61B 5/4064* (2013.01);
(Continued)

(58) Field of Classification Search
None
See application file for complete search history.

(56) References Cited

U.S. PATENT DOCUMENTS 8,150,629 B2   4/2012 Geerts et al.
8,696,722 B2   4/2014 Deisseroth et al.
(Continued)

FOREIGN PATENT DOCUMENTS

WO   WO 2017015395   1/2017
WO   WO 2017040538   3/2017
WO   WO 2017100058   6/2017

OTHER PUBLICATIONS

Bernal-Casas et al., (2017) "Studying Brain Circuit Function with Dynamic Causal Modeling for Optogenic fMRI", Neuron 93(3):522-532.
(Continued)

*Primary Examiner* — Rodney E Fuller
(74) *Attorney, Agent, or Firm* — Rudy J. Ng; Bozicevic, Field & Francis

(57) ABSTRACT

Methods and systems for analyzing brain functional activity data are provided. Also provided are systems that find use in performing the present methods.

40 Claims, 48 Drawing Sheets

(51) Int. Cl.
*A61B 5/00* (2006.01)
*G01R 33/48* (2006.01)
*G16H 50/50* (2018.01)
*G16H 50/20* (2018.01)
*G06T 7/00* (2017.01)
*A61N 5/06* (2006.01)
*A61B 5/246* (2021.01)
*G16Z 99/00* (2019.01)
*A61B 5/245* (2021.01)
*A61B 5/369* (2021.01)

(52) U.S. Cl.
CPC ....... *A61N 5/0622* (2013.01); *G01R 33/4806* (2013.01); *G06T 7/0012* (2013.01); *G16H 50/20* (2018.01); *G16H 50/50* (2018.01); *G16Z 99/00* (2019.02); *A61B 5/245* (2021.01); *A61B 5/369* (2021.01); *A61B 2576/026* (2013.01)

(56) References Cited

U.S. PATENT DOCUMENTS

| | | |
|---|---|---|
| 8,834,546 B2 | 9/2014 | Deisseroth et al. |
| 9,271,674 B2 | 5/2016 | Deisseroth et al. |
| 2004/0092809 A1 | 5/2004 | DeCharms |
| 2009/0318794 A1 | 12/2009 | DeCharms |
| 2014/0364721 A1 | 12/2014 | Lee et al. |
| 2015/0088024 A1 | 3/2015 | Sackellares et al. |
| 2016/0019693 A1 | 1/2016 | Silbersweig et al. |
| 2016/0270723 A1 | 9/2016 | Deisseroth et al. |
| 2019/0150742 A1* | 5/2019 | Lee .................... G01R 33/4824 |
| 2019/0264285 A1* | 8/2019 | Li ...................... G01N 33/6893 |

OTHER PUBLICATIONS

Friston et al., (2013) "A DCM for Resting State fMRI", Neuroimage 94:396-407.

Lee (2010) "Global and Local fMRI Signals Driven by Neurons Defined Optogenetically by Type and Wiring", Nature 465(7299):788-792.

Berndt et al., (2014) "Structure-Guided Transformation of Channelrhodopsin into a Light-Activated Chloride Channel," *Science*, 344: 420-424.

Berndt & Deisseroth (2015) "Expanding the optogenetics toolkit," *Science*, 349(6248): 590-591.

* cited by examiner

The basal ganglia-thalamocortical complex in mice

Anterior Caudate Putamen (CPu)
Globus Pallidus External (GPe)
Globus Pallidus Internal (GPi)
Subthalamic Nucleus (STN)
Substantia Nigra (SN)
Thalamus (THL)
Motor Cortex (MOT)

The basal ganglia-thalamocortical complex in humans

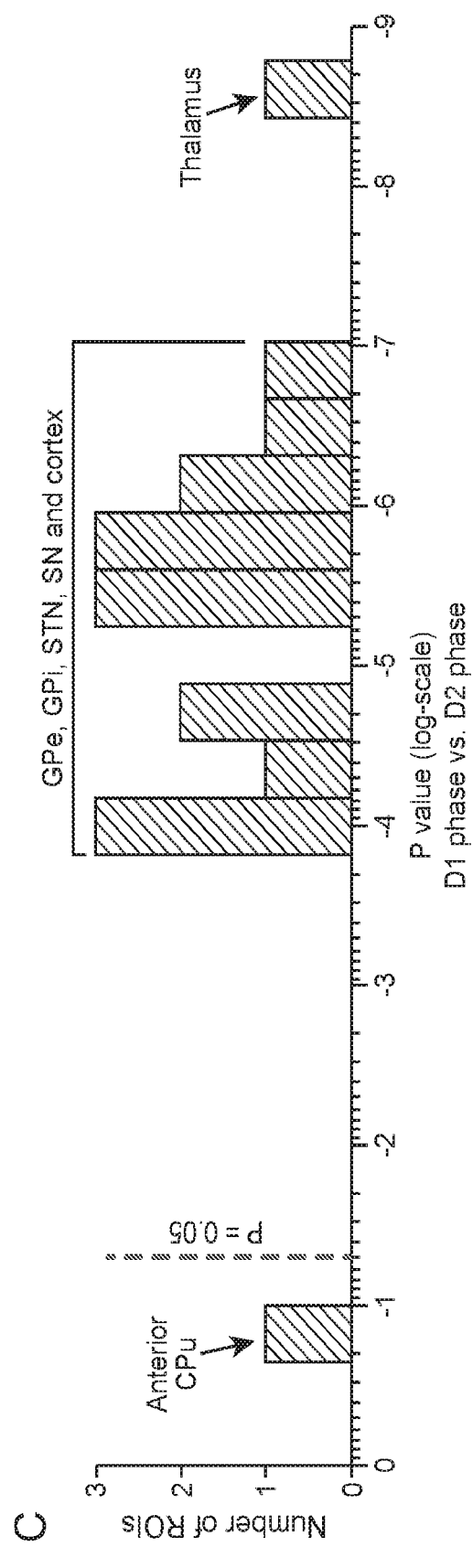
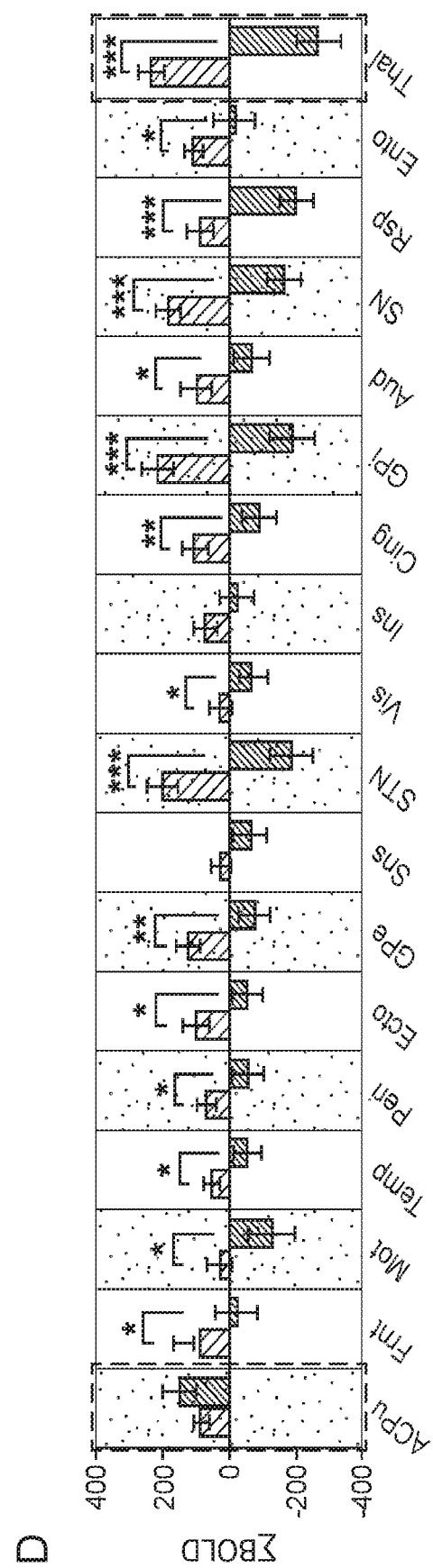
FIG. 4 (Cont.)

FIG. 5
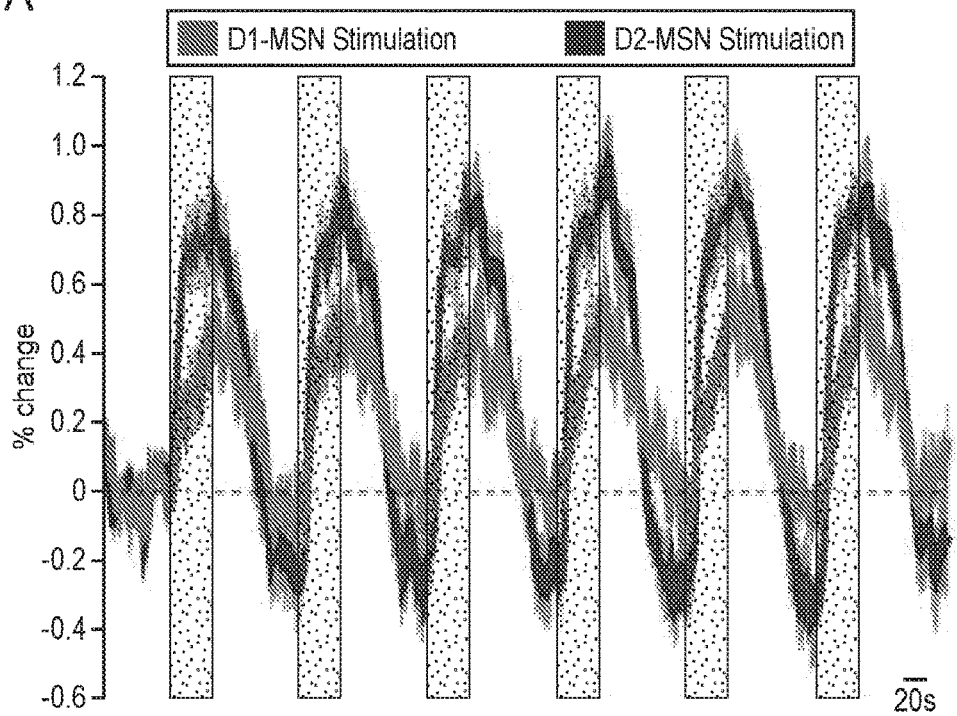
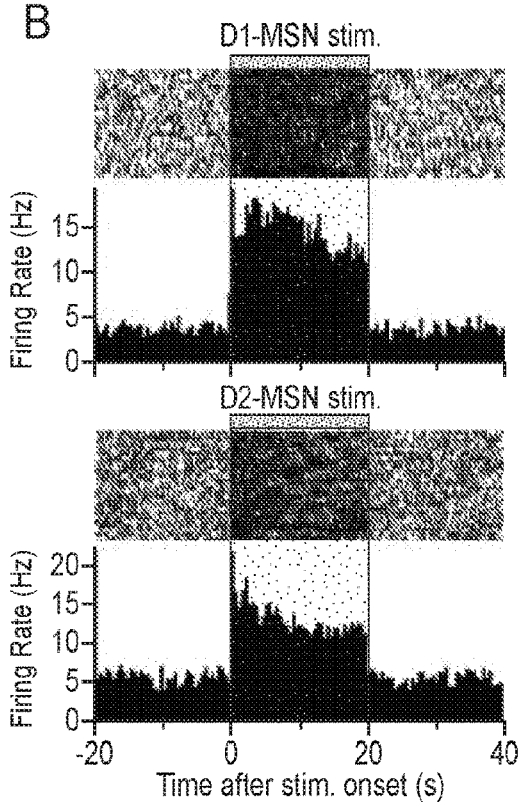
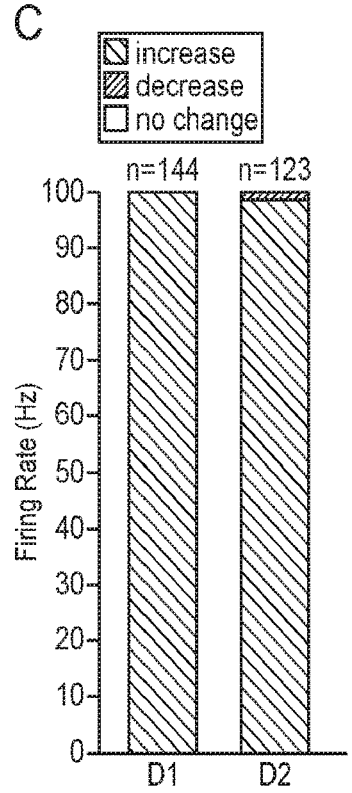

FIG. 5 (Cont.)
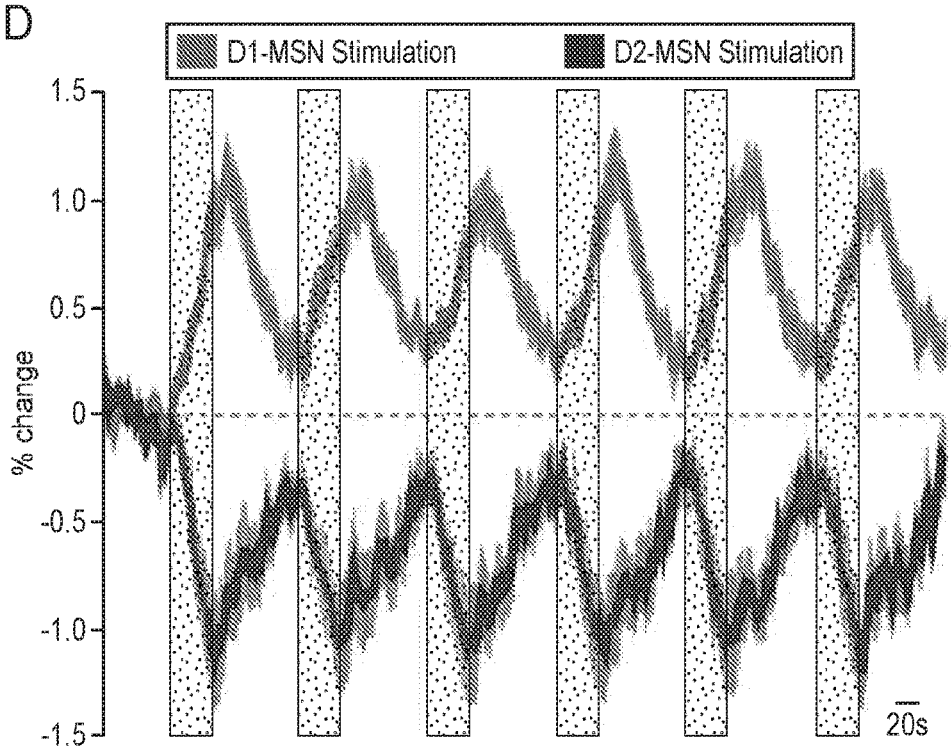
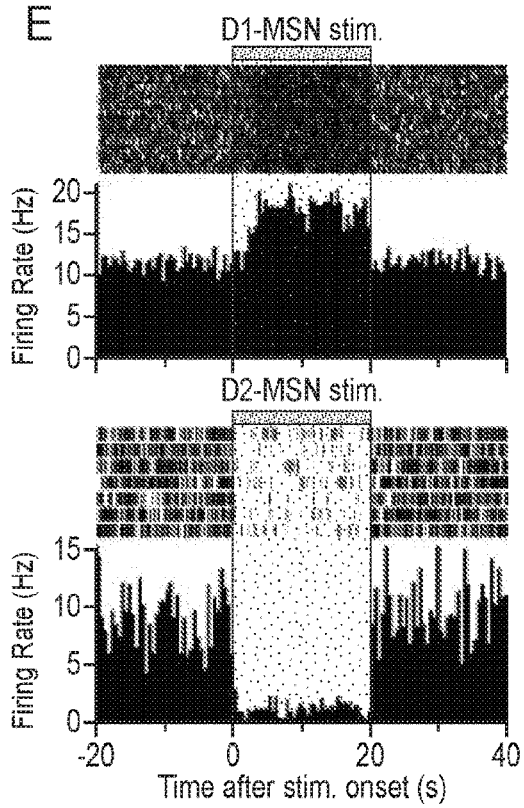
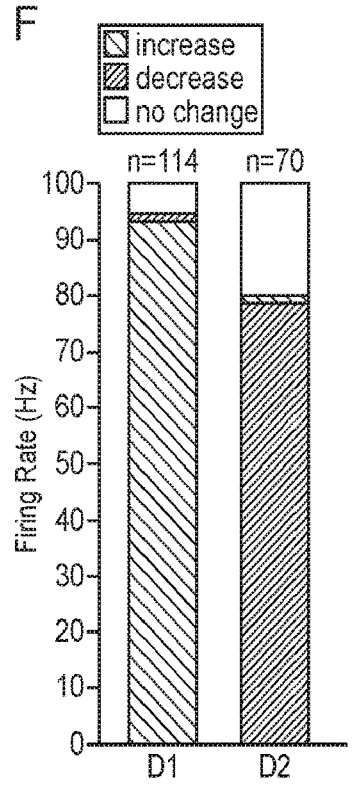

FIG. 9
A
Motor Network Regions of Interest
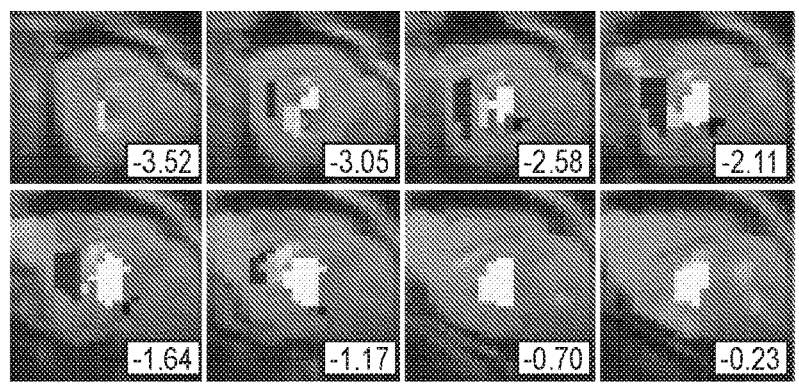
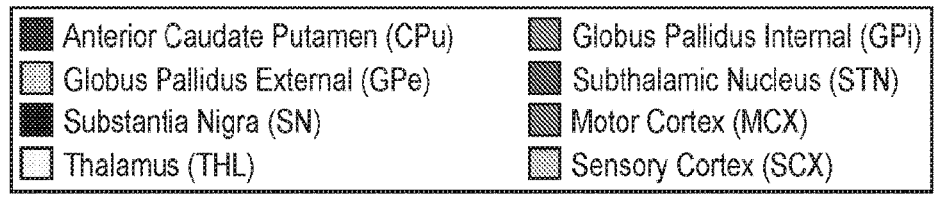
B
Sensory Network Regions of Interest
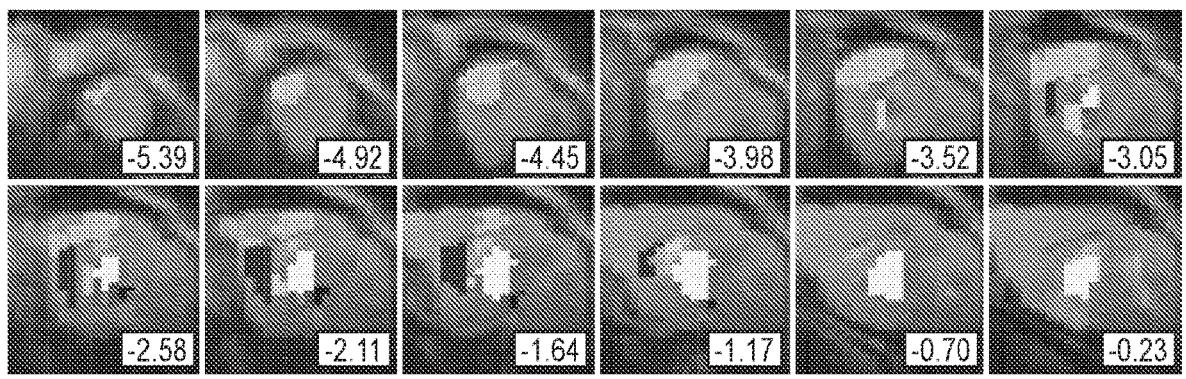
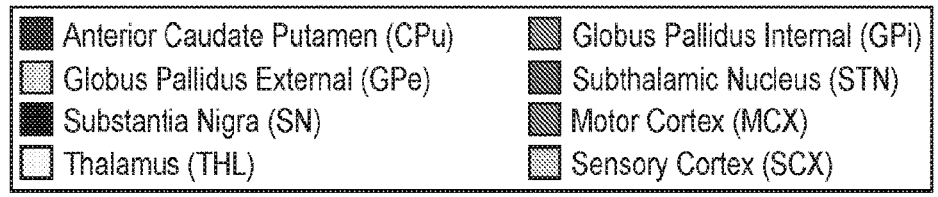

C (Cont.)

D (Cont.)

FIG. 10
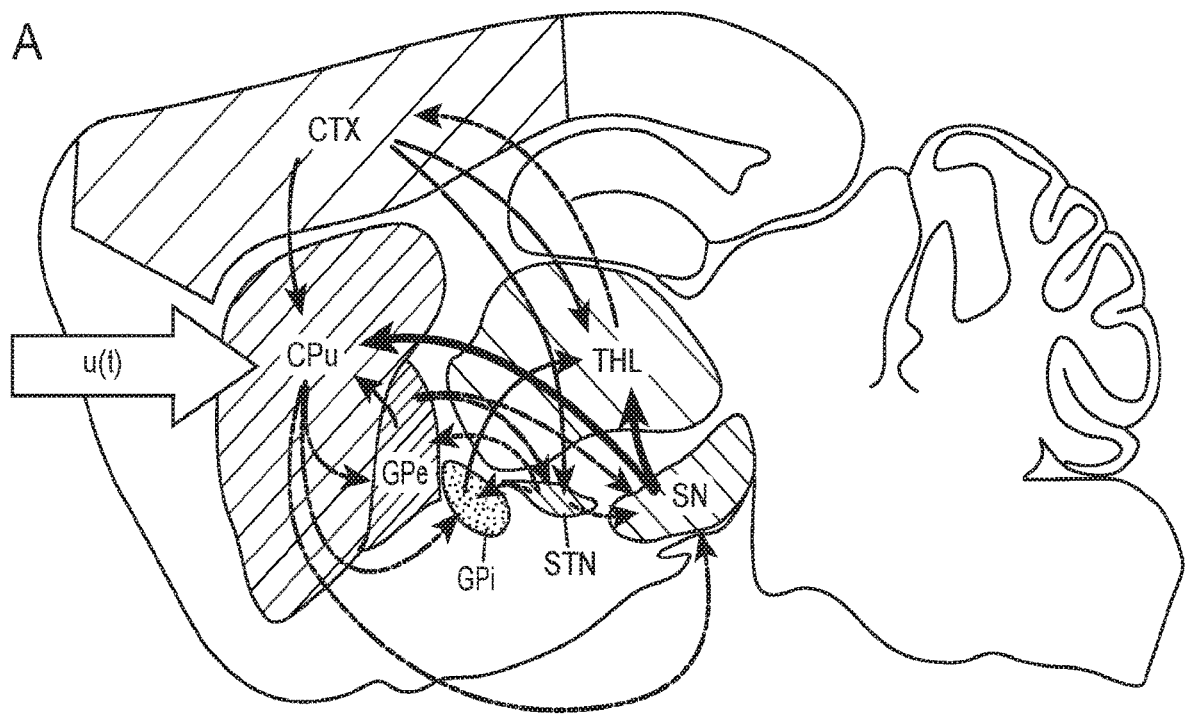
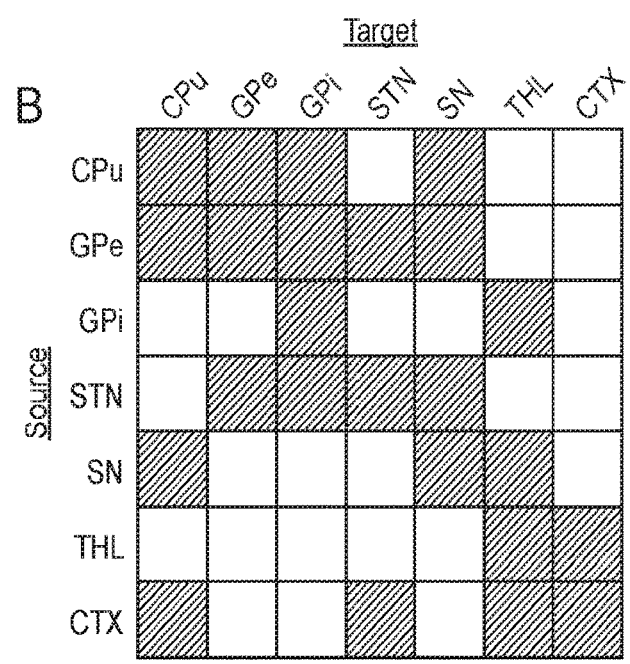

FIG. 11
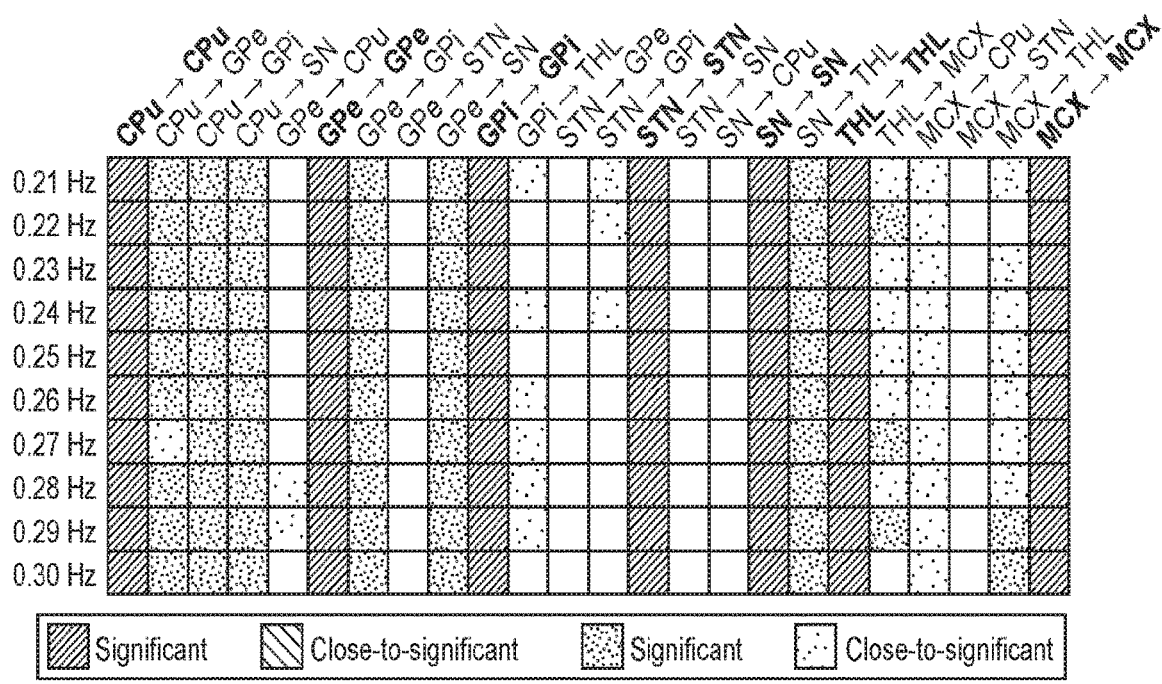
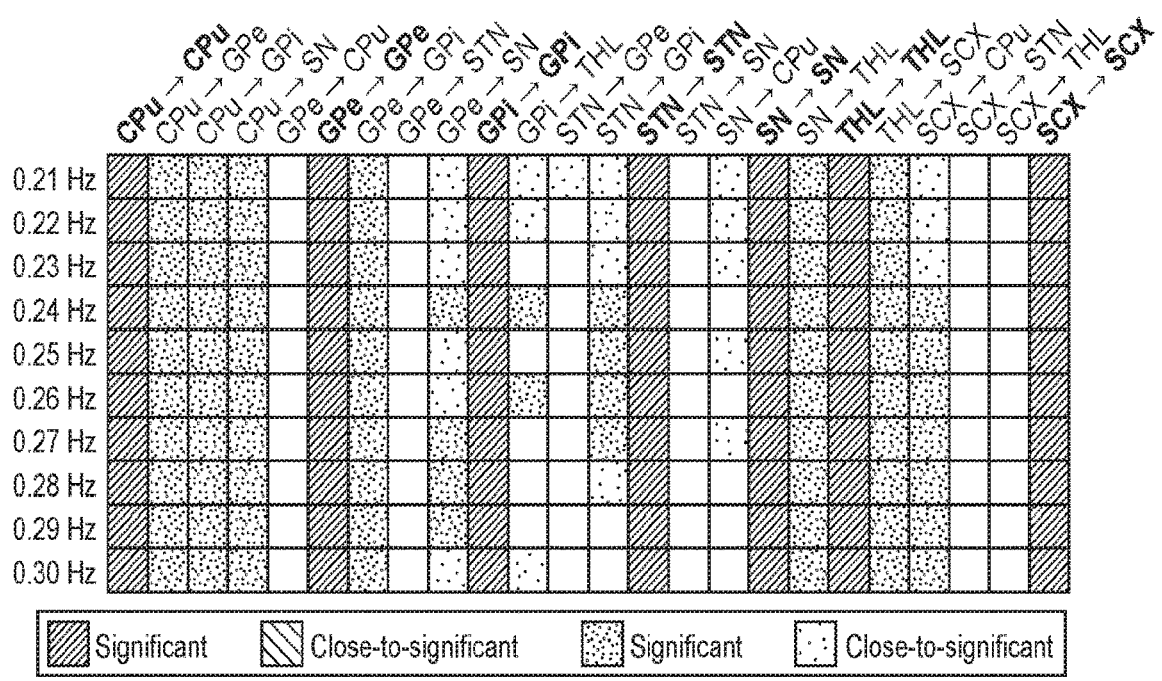

FIG. 11 (Cont.)
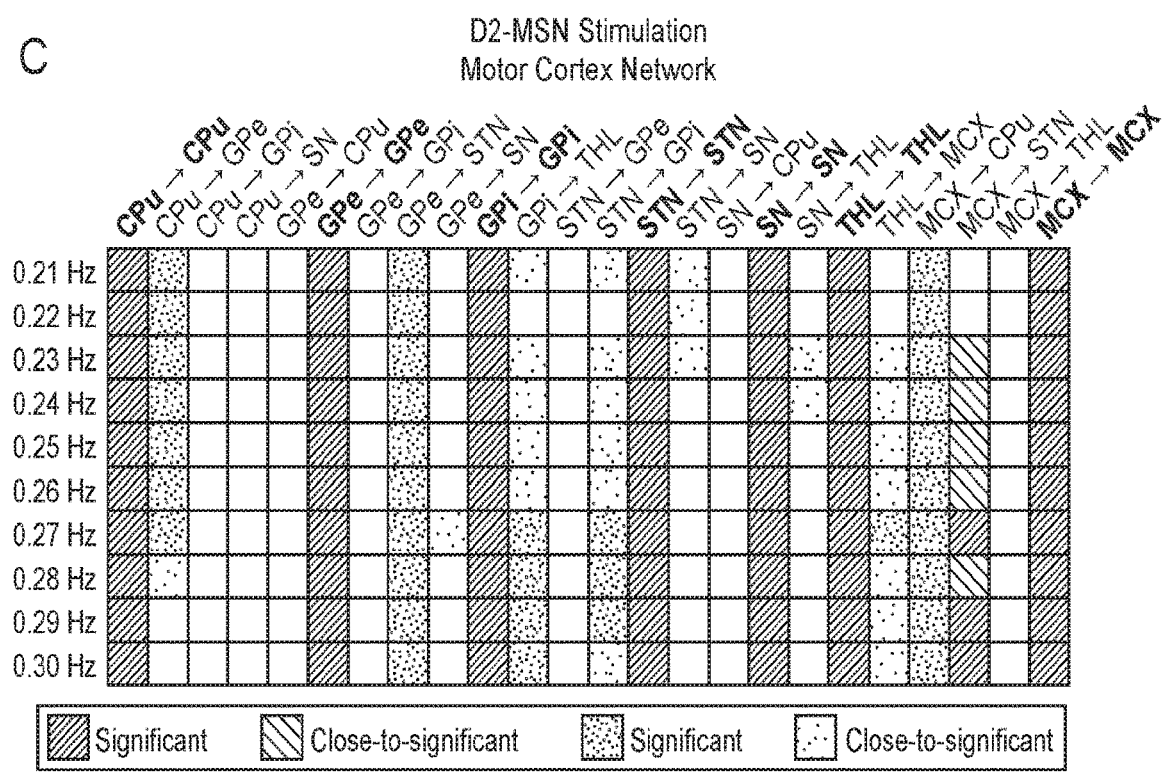
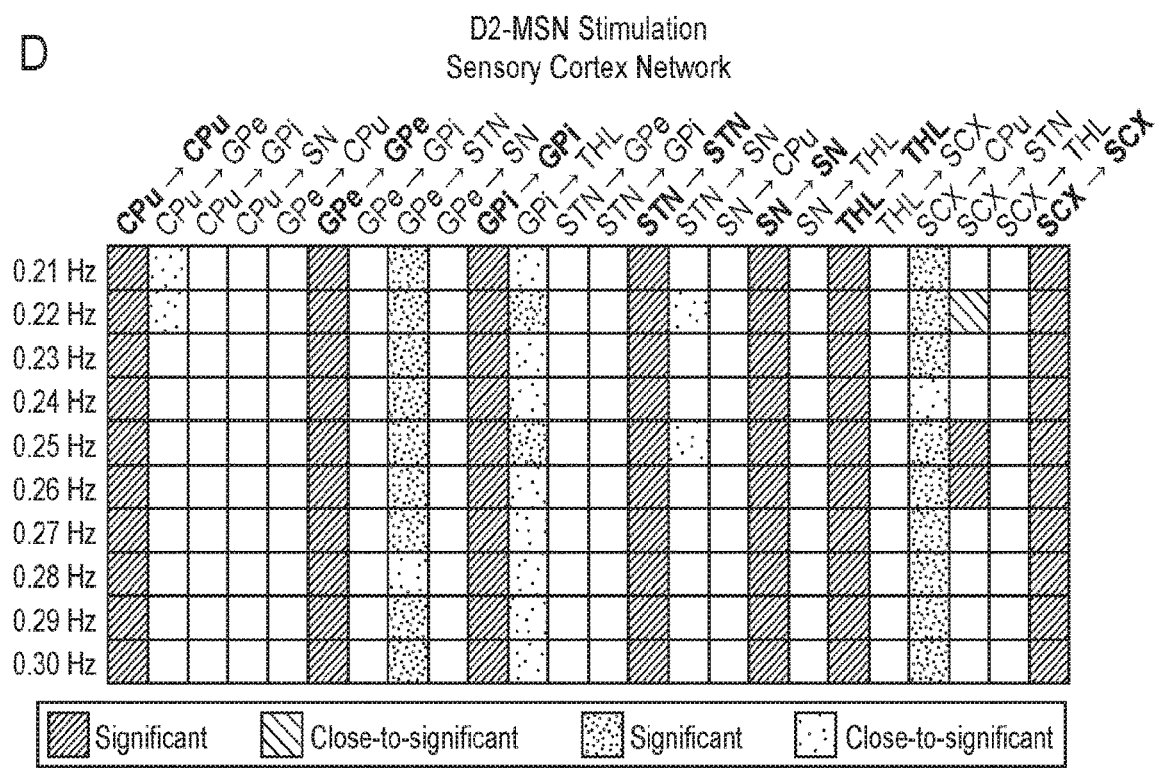

FIG. 12
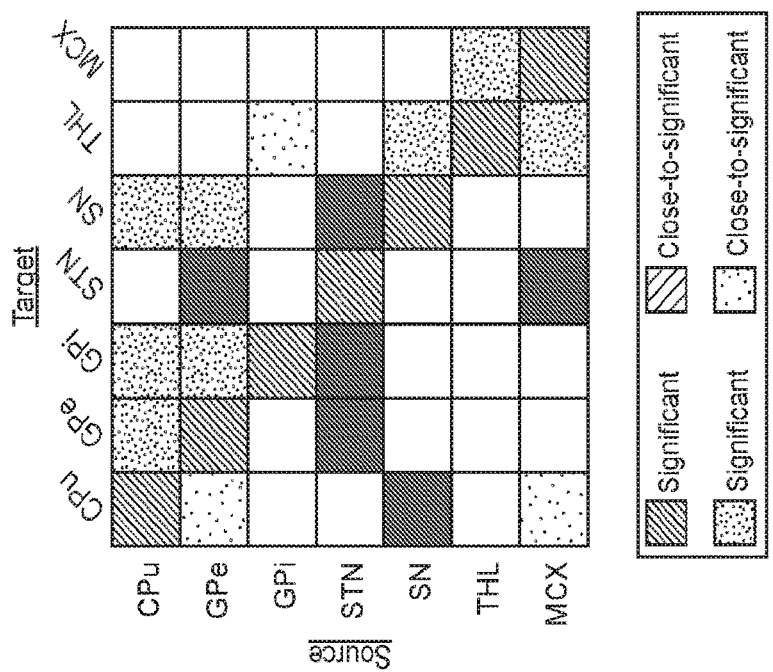
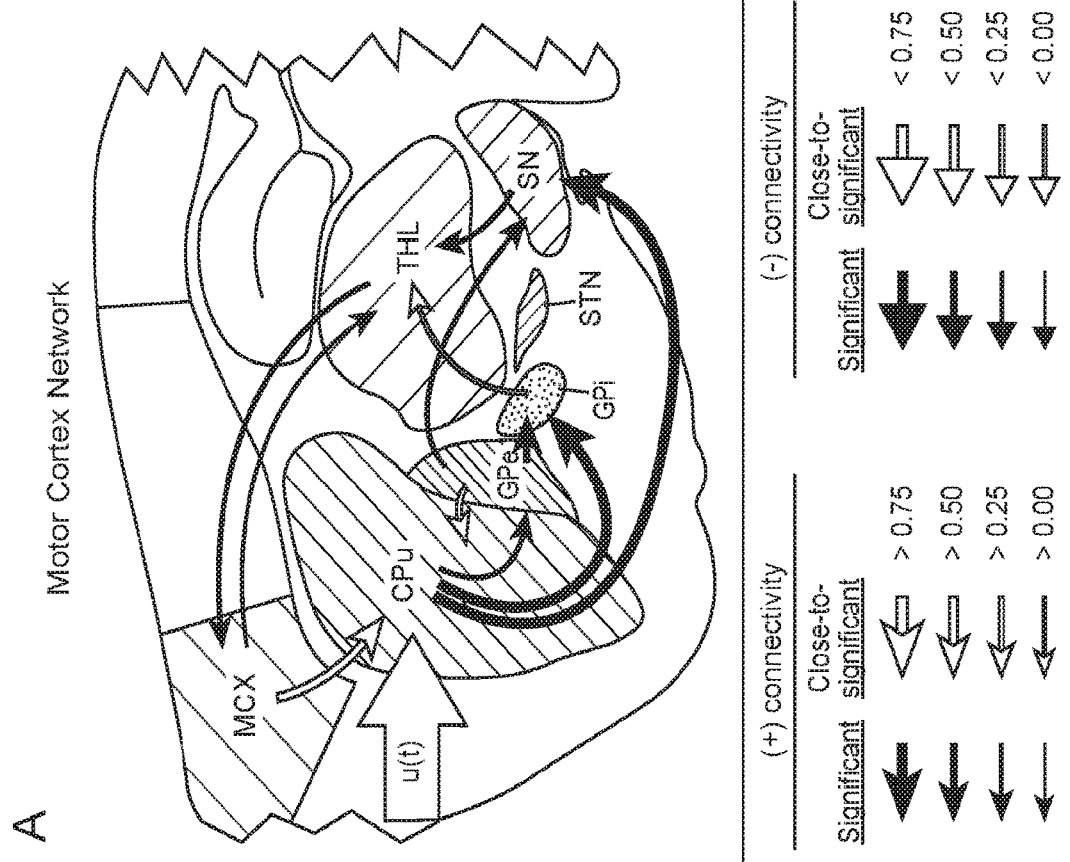

FIG. 12 (Cont.)
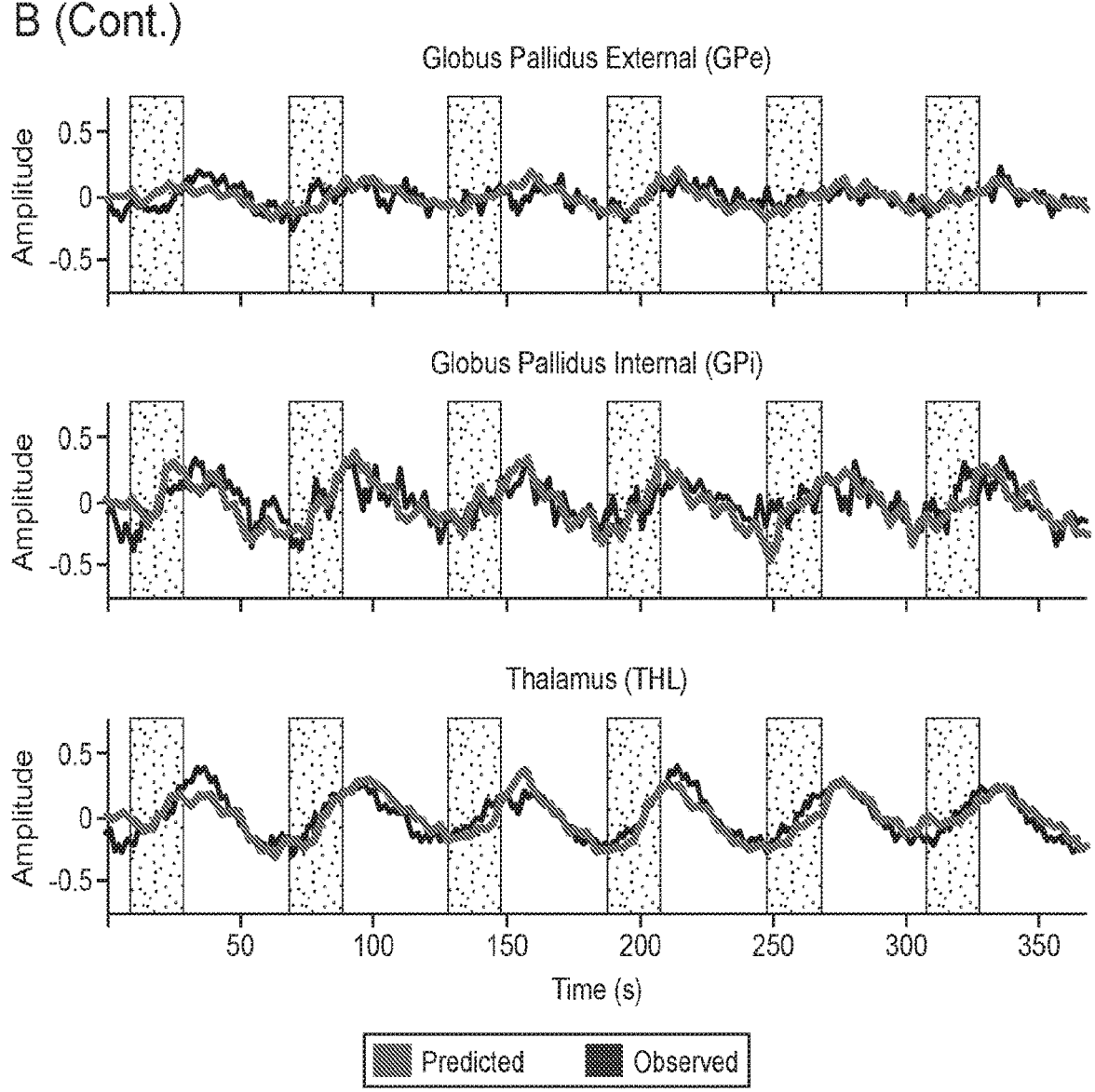
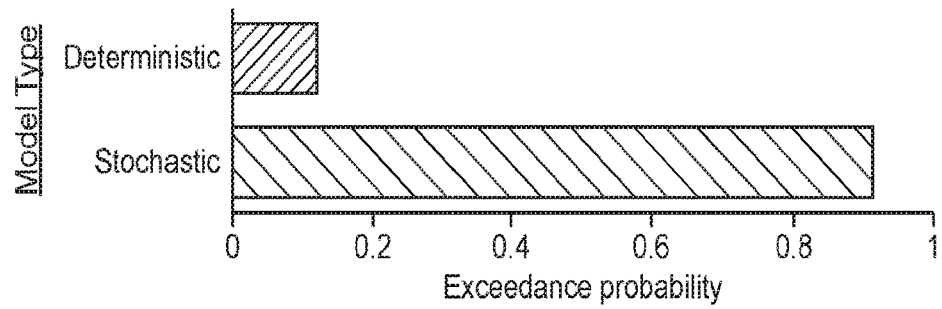

FIG. 12 (Cont.)
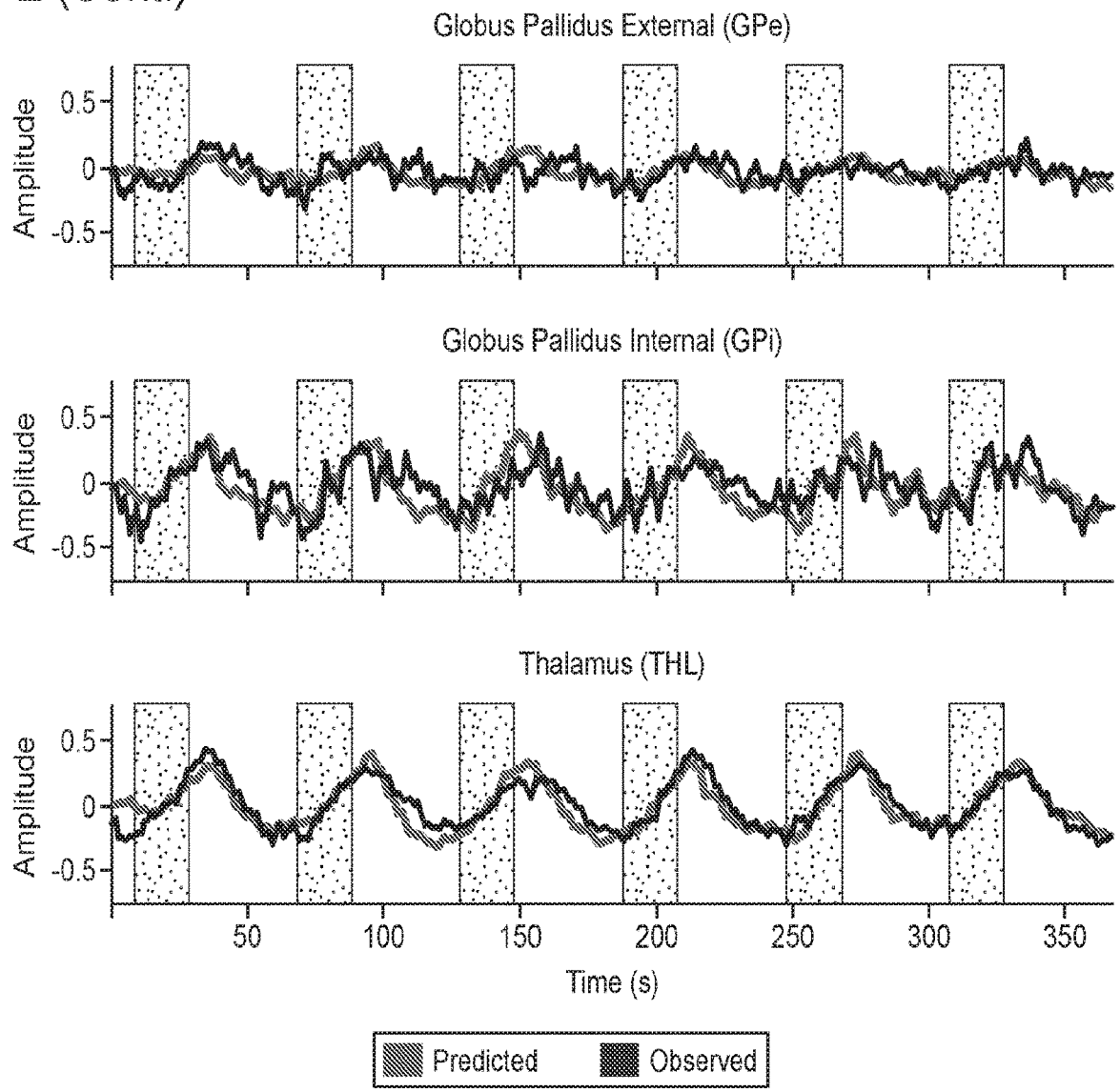
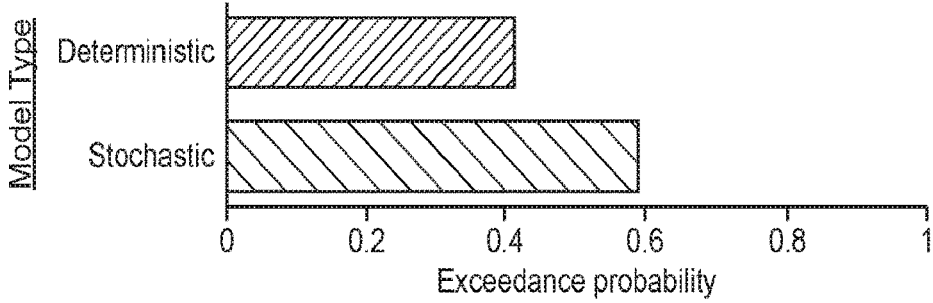

FIG. 13

Table 3

| | | MCX network case<br>Mean connectivity estimate; 95% CI<br>p-value (uncorrected); p-value (corrected) | | SCX network case<br>Mean connectivity estimate; 95% CI<br>p-value (uncorrected); p-value (corrected) | |
|---|---|---|---|---|---|
| CPu → | CPu | -1.8311; (-2.2770, -1.3852)<br>$6.1654 \times 10^{-6}$; $3.6572 \times 10^{-5}$ | *** | -2.0250; (-2.4503, -1.5996)<br>$1.4687 \times 10^{-6}$; $1.1749 \times 10^{-5}$ | *** |
| | GPe | 0.4452; (0.1938, 0.6967)<br>0.0052; 0.0105 | * | 0.4427; (0.2116, 0.6738)<br>0.0032; 0.0064 | * |
| | GPi | 0.9177; (0.4582, 1.3772)<br>0.0024; 0.0072 | ** | 0.8454; (0.4587, 1.2320)<br>0.0013; 0.0031 | ** |
| | SN | 0.9155; (0.6875, 1.1434)<br>$7.6191 \times 10^{-6}$; $3.6572 \times 10^{-5}$ | *** | 0.9399; (0.6829, 1.1969)<br>$1.8248 \times 10^{-5}$; $8.7588 \times 10^{-5}$ | *** |
| GPe → | CPu | -0.1600; (-0.3136, -0.0063)<br>0.0661; 0.0881 | cts | -0.0373; (-0.2004, 0.1259)<br>0.6629; 0.6917 | |
| | GPe | -0.4998; (-0.7680, -0.2316)<br>0.0038; 0.0091 | ** | -0.6057; (-0.8513, -0.3601)<br>$5.2449 \times 10^{-5}$; 0.0014 | ** |
| | GPi | 0.6377; (0.3084, 0.9669)<br>0.0030; 0.0079 | * | 0.5441; (0.2527, 0.8356)<br>0.0038; 0.0069 | * |
| | STN | 0.1856; (-0.8987, 1.2699)<br>0.7436; 0.7759 | | 0.3338; (-0.3962, 1.0637)<br>0.3893; 0.4672 | |
| | SN | 0.4556; (0.1680, 0.7432)<br>0.0100; 0.0185 | * | 0.3718; (0.0980, 0.6455)<br>0.0221; 0.0354 | * |
| GPi → | GPi | -1.0409; (-1.1571, -0.9247)<br>$2.1503 \times 10^{-9}$; $5.1609 \times 10^{-8}$ | *** | -0.9750; (-1.0904, -0.8596)<br>$4.0113 \times 10^{-9}$; $9.6271 \times 10^{-8}$ | *** |
| | THL | 0.1555; (0.0073, 0.3036)<br>0.0643; 0.0881 | cts | 0.1711; (0.0656, 0.2767)<br>0.0088; 0.0151 | * |
| STN → | GPe | 0.0469; (-0.1462, 0.2401)<br>0.6433; 0.7018 | | 0.1388; (-0.1044, 0.3820)<br>0.2870; 0.3827 | |
| | GPi | 0.2240; (-0.0406, 0.4886)<br>0.1253; 0.1583 | * | 0.1891; (0.0438, 0.3344)<br>0.0270; 0.0381 | * |
| | STN | -0.4161; (-0.6129, -0.2193)<br>0.0016; 0.0056 | *** | -0.5330; (-0.7170, -0.3490)<br>$1.4307 \times 10^{-4}$; $4.9052 \times 10^{-4}$ | *** |
| | SN | -0.0732; (-0.2576, 0.1112)<br>0.4528; 0.5434 | | -0.0524; (-0.1891, 0.0843)<br>0.4684; 0.5110 | |
| SN → | CPu | 0.0603; (-0.0096, 0.2201)<br>0.4754; 0.5434 | | 0.0654; (-0.0931, 0.2239)<br>0.4356; 0.4979 | |
| | SN | -0.7379; (-0.8627, -0.6132)<br>$1.6497 \times 10^{-7}$; $1.9796 \times 10^{-6}$ | *** | -0.7935; (-0.9694, -0.6177)<br>$2.4906 \times 10^{-6}$; $1.4944 \times 10^{-5}$ | *** |
| | THL | 0.4234; (0.1895, 0.6574)<br>0.0046; 0.0100 | *** | 0.4704; (0.3250, 0.6157)<br>$5.4974 \times 10^{-5}$; $2.1989 \times 10^{-4}$ | *** |
| THL → | THL | -1.0242; (-1.3371, -0.7113)<br>$4.9756 \times 10^{-5}$; $1.9902 \times 10^{-4}$ | *** | -0.9839; (-1.3499, -0.6180)<br>$2.6444 \times 10^{-4}$; $7.9332 \times 10^{-4}$ | *** |
| | CTX | 0.3166; (0.0718, 0.5615)<br>0.0278; 0.0444 | * | 0.4666; (0.2293, 0.7038)<br>0.0027; 0.0058 | * |
| CTX → | CPu | 0.5521; (0.1054, 0.9987)<br>0.0338; 0.0508 | cts | 0.4752; (0.1183, 0.8320)<br>0.0243; 0.0364 | * |
| | STN | 0.0840; (-0.6121, 0.7801)<br>0.8174; 0.8174 | | 0.3577; (-0.4231, 1.1386)<br>0.3884; 0.4672 | |
| | THL | 0.2790; (0.0740, 0.4841)<br>0.0219; 0.0376 | * | -0.0041; (-0.2459, 0.2378)<br>0.9743; 0.9743 | |
| | CTX | -1.4466; (-1.7381, -1.1551)<br>$6.2848 \times 10^{-8}$; $7.7978 \times 10^{-6}$ | *** | -1.5191; (-1.8306, -1.2077)<br>$1.1564 \times 10^{-6}$; $1.1749 \times 10^{-5}$ | *** |

FIG. 14
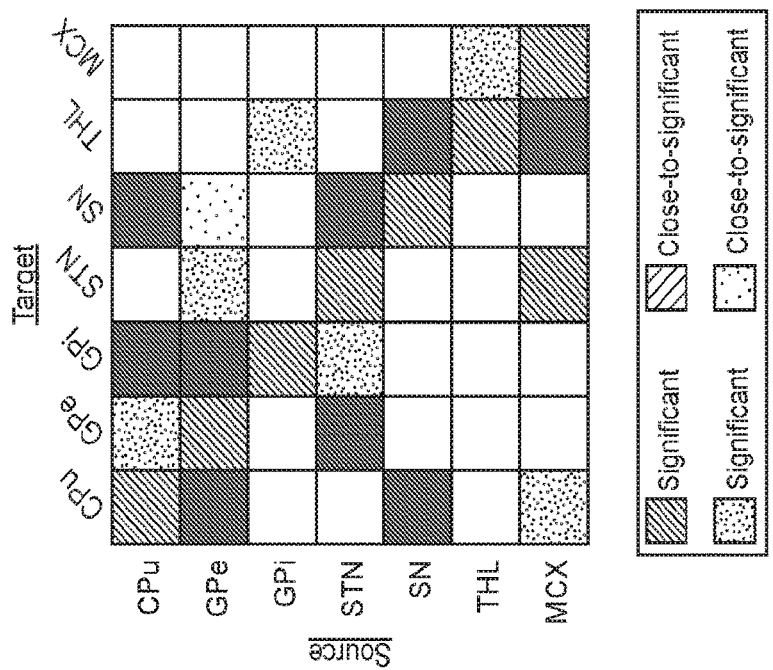
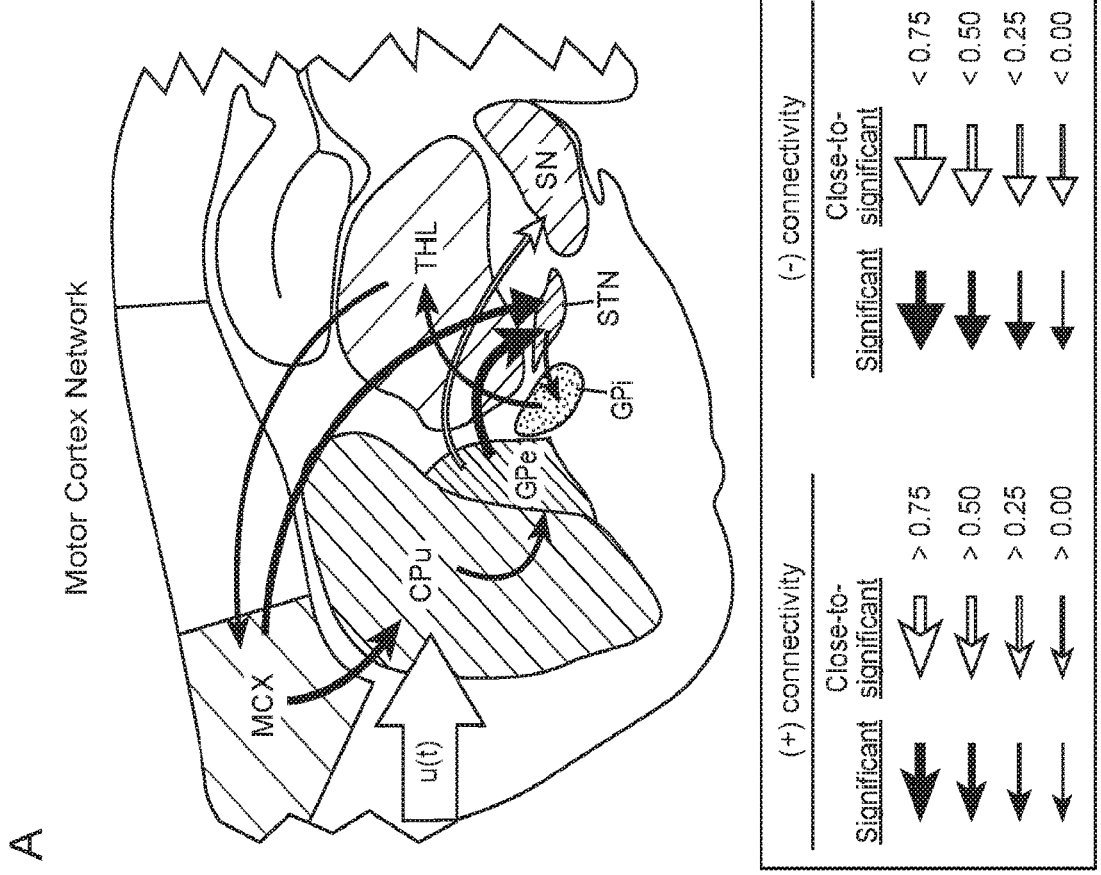

FIG. 14 (Cont.)
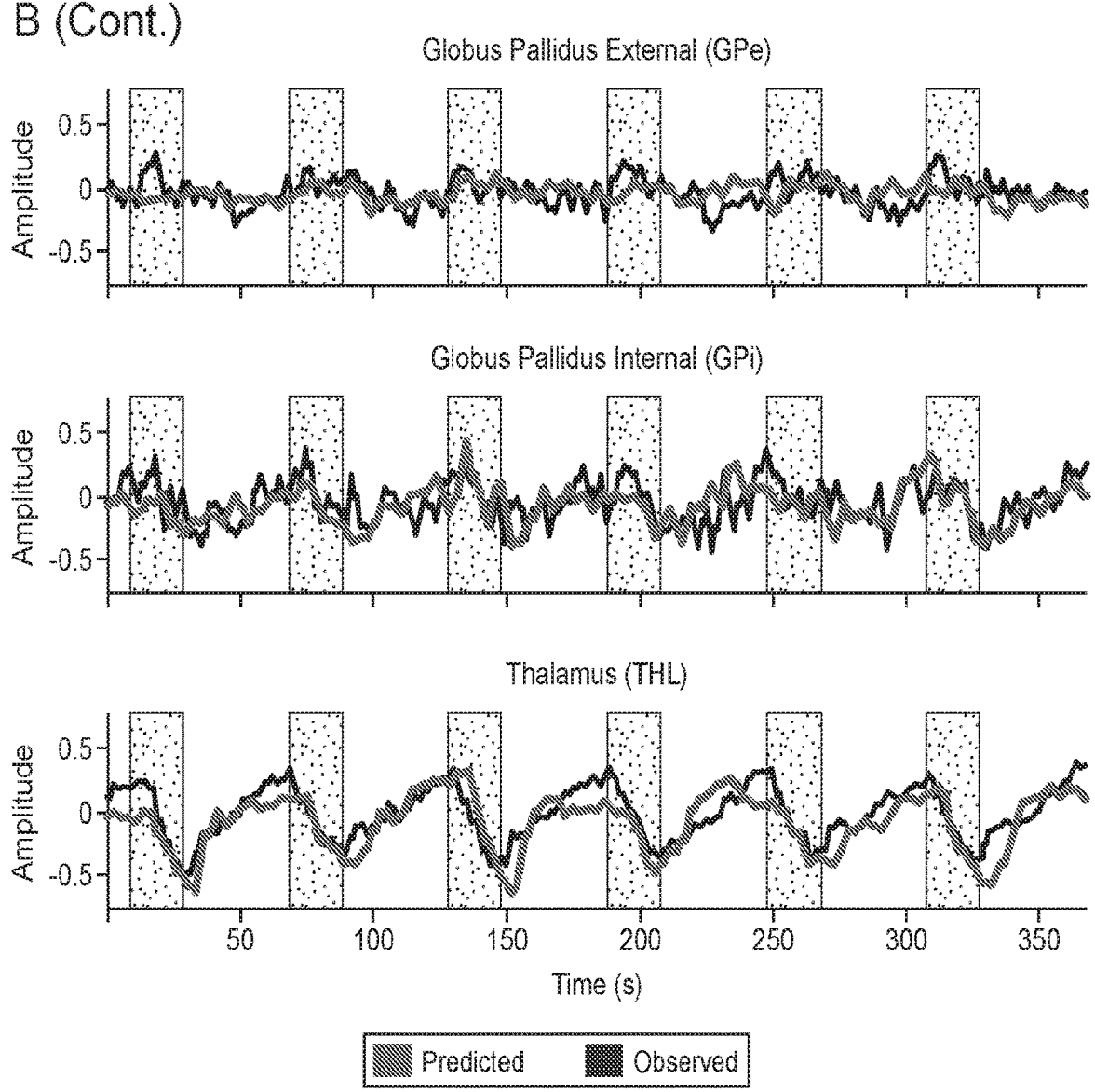
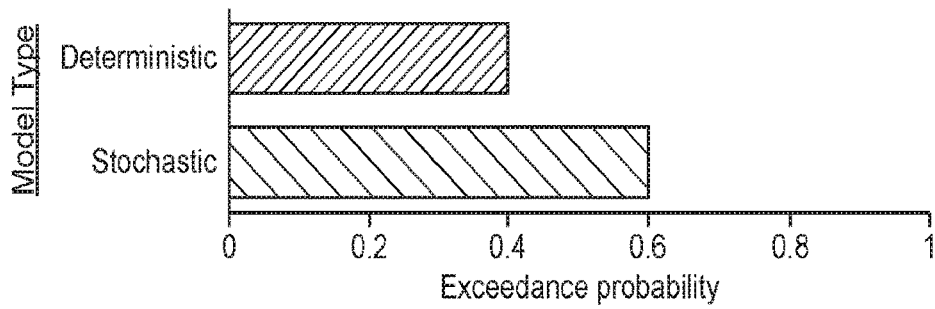

FIG. 14 (Cont.)
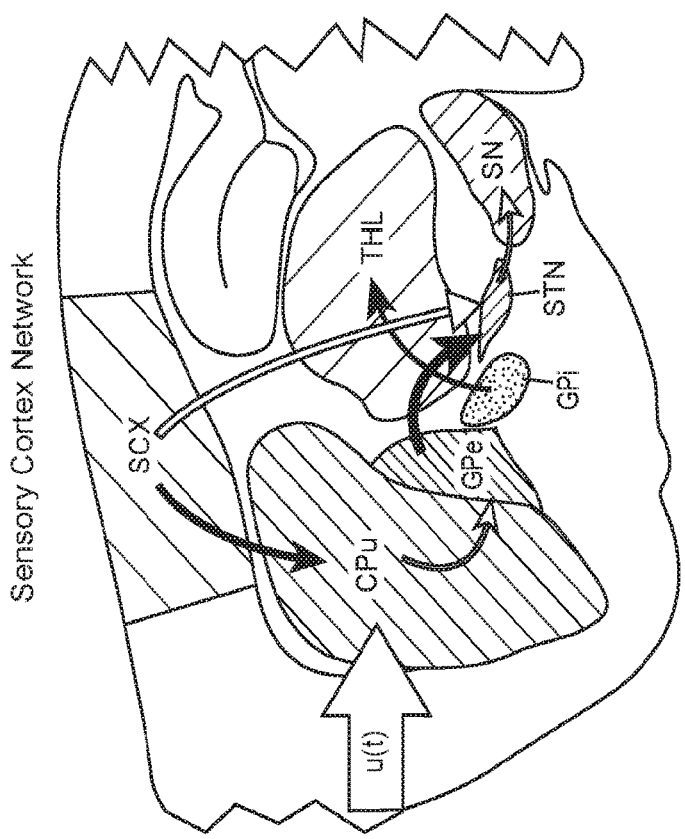
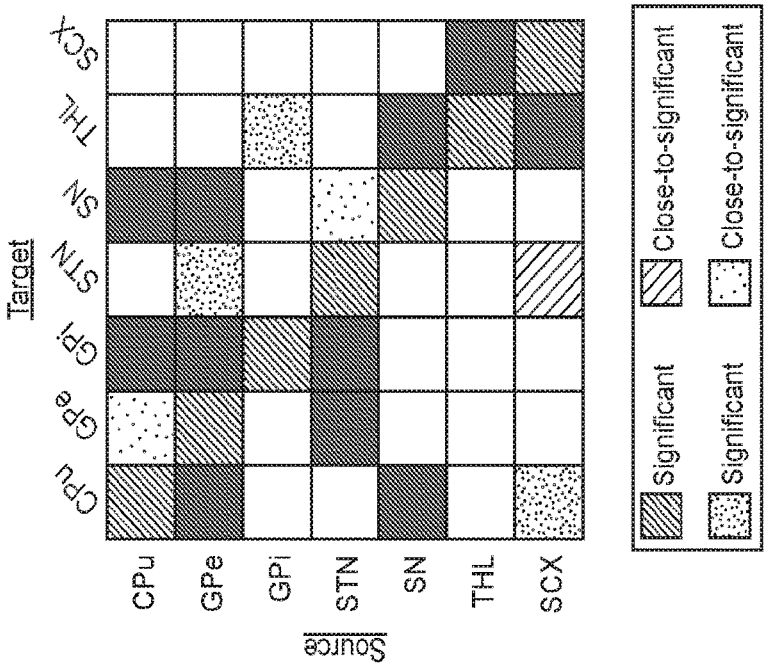
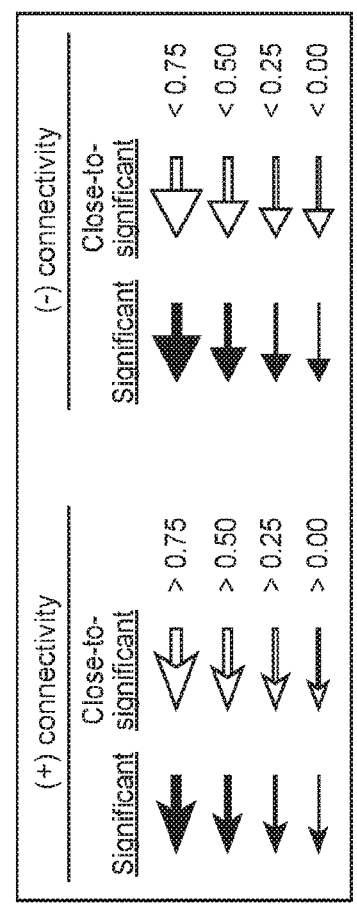

FIG. 14 (Cont.)
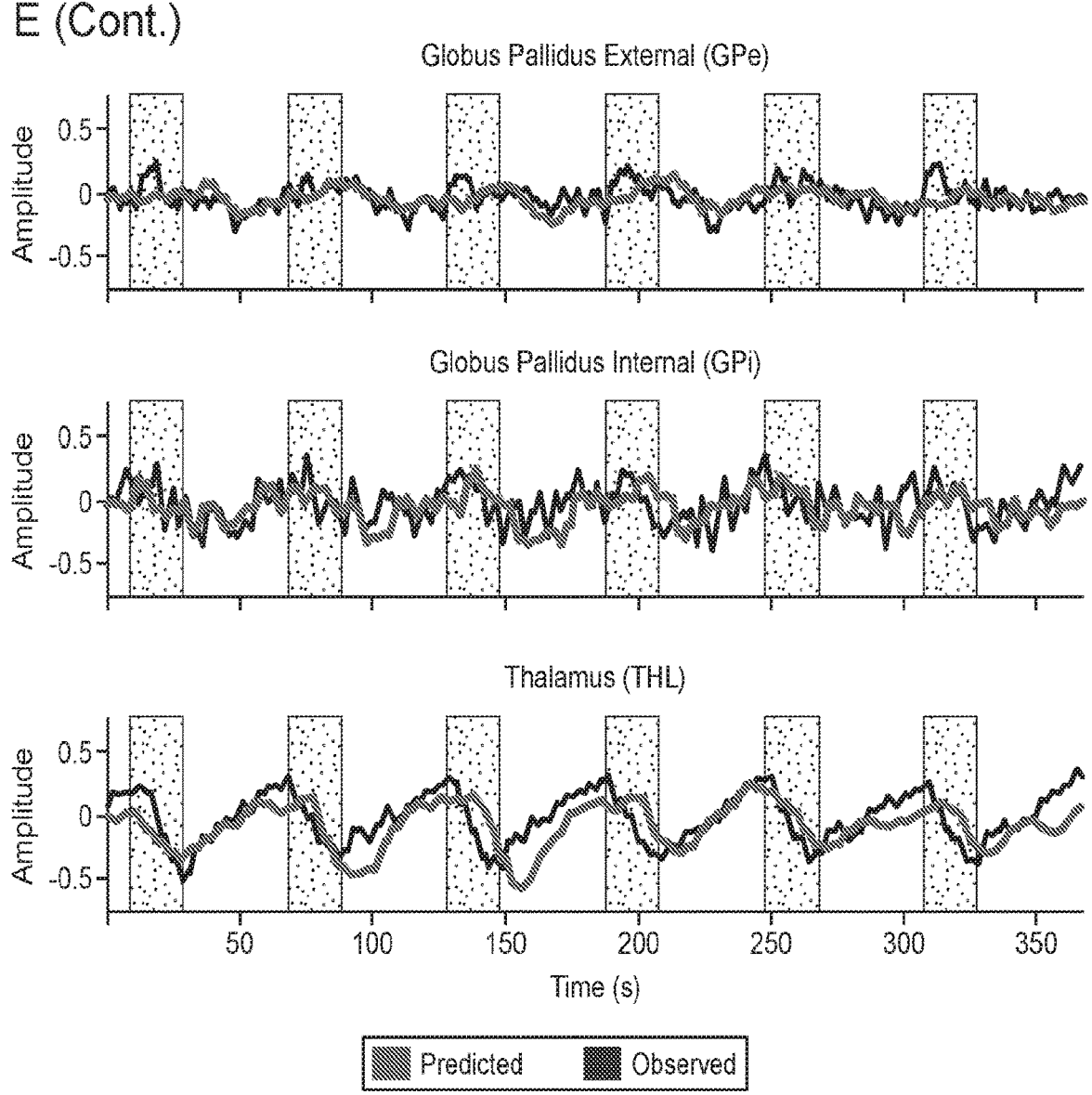
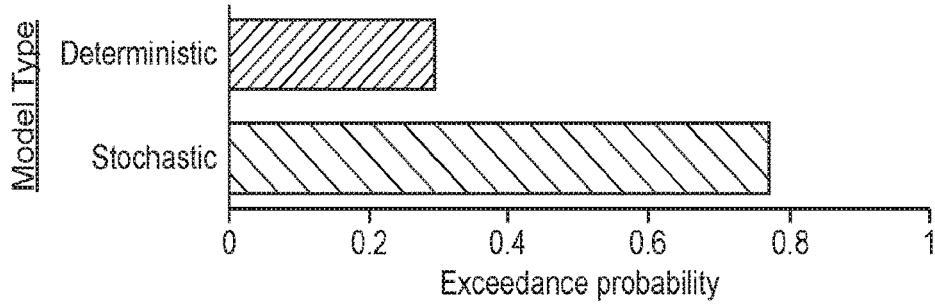

FIG. 15

| Table 4 | | MCX network case | | SCX network case | |
|---|---|---|---|---|---|
| | | Mean connectivity estimate; 95% CI p-value (uncorrected); p-value (corrected) | | Mean connectivity estimate; 95% CI p-value (uncorrected); p-value (corrected) | |
| CPu → | CPu | -0.8046; (-0.9642, -0.6449) $3.9715 \times 10^{-6}$; $3.1772 \times 10^{-5}$ | *** | =1.0184; (-1.2866, -0.7503) $3.9189 \times 10^{-5}$; $3.1351 \times 10^{-4}$ | *** |
| | GPe | 0.3089; (0.0794, 0.5383) 0.0270; 0.0496 | * | 0.2288; (0.0471, 0.4106) 0.0357; 0.0779 | cts |
| | GPi | 0.0025; (-0.2688, 0.2739) 0.9858; 0.9858 | | -0.0480; (-0.2823, 0.1863) 0.6972; 0.7605 | |
| | SN | 0.1026; (-0.0740, 0.2791) 0.2842; 0.3248 | | 0.2217; (-0.0499, 0.4934) 0.1441; 0.2162 | |
| GPe → | CPu | -0.0667; (-0.3817, 0.2482) 0.6876; 0.7175 | | 0.2133; (-0.3528, 0.7793) 0.4791; 0.5717 | |
| | GPe | -1.0799; (-1.3777, -0.7843) $5.30071 \times 10^{-5}$; $2.1203 \times 10^{-4}$ | ** | -1.1032; (-1.5031, -0.7033) $4.2923 \times 10^{-4}$; 0.0021 | ** |
| | GPi | 0.3015; (-0.0431, 0.6462) 0.1206; 0.1702 | | 0.3018; (-0.0959, 0.6995) 0.1711; 0.2416 | |
| | STN | 1.1176; (0.7550, 1.4803) $1.9270 \times 10^{-4}$; $5.7809 \times 10^{-4}$ | *** | 0.9814; (0.6392, 1.3237) $3.2561 \times 10^{-4}$; 0.0020 | ** |
| | SN | 0.3551; (0.0394, 0.6708) 0.0549; 0.0878 | cts | 0.2822; (-0.0241, 0.5885) 0.1044; 0.1671 | |
| GPi → | GPi | -1.1923; (-1.3635, -1.0211) $2.5518 \times 10^{-7}$; $6.1242 \times 10^{-6}$ | *** | -1.2649; (-1.4559, -1.0740) $3.9263 \times 10^{-7}$; $9.4231 \times 10^{-6}$ | *** |
| | THL | 0.4156; (0.1288, 0.7025) 0.0194; 0.0466 | * | 0.4196; (0.1374, 0.7018) 0.0172; 0.0413 | * |
| STN → | GPe | -0.0576; (-0.2922, 0.1776) 0.6439; 0.7024 | | -0.0291; (-0.2946, 0.2363) 0.8346; 0.8346 | |
| | GPi | 0.4254; (0.1257, 0.7251) 0.0213; 0.0466 | * | 0.3710; (0.0116, 0.7303) 0.0737; 0.1263 | |
| | STN | -0.7868; (-0.9784, -0.5952) $2.1061 \times 10^{-5}$; $1.0109 \times 10^{-4}$ | *** | -0.8004; (-1.1243, -0.4766) $9.1604 \times 10^{-4}$; 0.0037 | ** |
| | SN | 0.1889; (-0.0245, 0.4023) 0.1167; 0.1702 | | 0.2563; (0.0459, 0.4667) 0.0407; 0.0815 | cts |
| SN → | CPu | -0.1803; (-0.4899, 1293) 0.2823; 0.3248 | | -0.1148; (-0.3202, 0.0906) 0.3017; 0.3811 | |
| | SN | -1.2963; (-1.5479, -1.0447) $3.2999 \times 10^{-6}$; $3.1772 \times 10^{-5}$ | *** | -2.0027; (-2.8539, -1.1516) 0.0013; 0.0044 | ** |
| | THL | 0.1981; (-0.0347, 0.4310) 0.1297; 0.1730 | | 0.0733; (-0.4318, 0.5783) 0.7826; 0.8166 | |
| THL → | THL | -1.0121; (-1.3126, -0.7116) $9.9123 \times 10^{-5}$; $3.3985 \times 10^{-4}$ | *** | -0.9573; (-1.3914, -0.5232) 0.0019; 0.0058 | * |
| | CTX | 0.4221; (0.1034, 0.7407) 0.0289; 0.0496 | * | 0.2764; (-0.1442, 0.6970) 0.2299; 0.3065 | |
| CTX → | CPu | 0.6985; (0.2363, 1.1607) 0.0159; 0.0424 | * | 0.7798; (0.2949, 1.2647) 0.0117; 0.0312 | * |
| | STN | -0.6773; (-1.1879, -0.1667) 0.0287; 0.0496 | * | -0.6833; (-1.2871, -0.0796) 0.0537; 0.0992 | cts |
| | THL | -0.2594; (-0.5950, 0.0763) 0.1642; 0.2074 | | 0.1017; (-0.1822, 0.3857) 0.5002; 0.5717 | |
| | CTX | -1.2685; (-1.5615, -0.9754) $1.3802 \times 10^{-5}$; $8.2811 \times 10^{-5}$ | *** | -2.4844; (-3.1139, -1.8550) $2.8920 \times 10^{-5}$; $3.1351 \times 10^{-4}$ | *** |

FIG. 17

Table 5

| | | MCX vs. SCX network case (D1-MSN Stim.) p-value (uncorrected); p-value (corrected) | | MCX vs. SCX network case (D2-MSN Stim.) p-value (uncorrected); p-value (corrected) | |
|---|---|---|---|---|---|
| CPu → | CPu | 0.6685; 0.9899 | | 0.1959; 0.9992 | |
| | GPe | 0.8807; 0.9899 | | 0.5985; 0.9992 | |
| | GPi | 0.5870; 0.9899 | | 0.7853; 0.9992 | |
| | SN | 0.7702; 0.9899 | | 0.4802; 0.9992 | |
| GPe → | CPu | 0.5951; 0.9899 | | 0.4080; 0.9992 | |
| | GPe | 0.9268; 0.9899 | | 0.9278; 0.9992 | |
| | GPi | 0.9412; 0.9899 | | 0.9992; 0.9992 | |
| | STN | 0.8991; 0.9899 | | 0.5989; 0.9992 | |
| | SN | 0.9558; 0.9899 | | 0.7490; 0.9992 | |
| GPi → | GPi | 0.6741; 0.9899 | | 0.5856; 0.9992 | |
| | THL | 0.9722; 0.9899 | | 0.9850; 0.9992 | |
| STN → | GPe | 0.7739; 0.9899 | | 0.8778; 0.9992 | |
| | GPi | 0.4432; 0.9899 | | 0.8223; 0.9992 | |
| | STN | 0.6519; 0.9899 | | 0.9441; 0.9992 | |
| | SN | 0.7721; 0.9899 | | 0.6646; 0.9992 | |
| SN → | CPu | 0.6202; 0.9899 | | 0.7338; 0.9992 | |
| | SN | 0.8642; 0.9899 | | 0.1362; 0.9992 | |
| | THL | 0.9899; 0.9899 | | 0.6652; 0.9992 | |
| THL → | THL | 0.7268; 0.9899 | | 0.8411; 0.9992 | |
| | CTX | 0.4178; 0.9899 | | 0.5950; 0.9992 | |
| CTX → | CPu | 0.9805; 0.9899 | | 0.8147; 0.9992 | |
| | STN | 0.5898; 0.9899 | | 0.9883; 0.9992 | |
| | THL | 0.1915; 0.9899 | | 0.1248; 0.9992 | |
| | CTX | 0.9421; 0.9899 | | 0.0030; 0.0713 | cts |

FIG. 19

Table 6

| | | D1- vs. D2-MSN stimulations (MCX) p-value (uncorrected); p-value (corrected) | | D1- vs. D2-MSN stimulations (SCX) p-value (uncorrected); p-value (corrected) | |
|---|---|---|---|---|---|
| CPu → | CPu | $8.2146 \times 10^{-4}$; 0.0066 | * | 0.0013; 0.0118 | * |
| | GPe | 0.4493; 0.5990 | | 0.1819; 0.2911 | |
| | GPi | 0.0046; 0.0276 | * | 0.0015; 0.0118 | * |
| | SN | $3.0474 \times 10^{-5}$; $7.3618 \times 10^{-4}$ | *** | 0.0013; 0.0118 | * |
| GPe → | CPu | 0.5884; 0.6905 | | 0.3779; 0.4535 | |
| | GPe | 0.0099; 0.0460 | * | 0.0436; 0.1308 | |
| | GPi | 0.1839; 0.3153 | | 0.3371; 0.4513 | |
| | STN | 0.1554; 0.3124 | | 0.1560; 0.2910 | |
| | SN | 0.6495; 0.6905 | | 0.6730; 0.7023 | |
| GPi → | GPi | 0.1562; 0.3124 | | 0.0156; 0.0623 | cts |
| | THL | 0.1127; 0.2704 | | 0.0989; 0.2374 | |
| STN → | GPe | 0.5052; 0.6382 | | 0.3716; 0.4535 | |
| | GPi | 0.3338; 0.5007 | | 0.3384; 0.4513 | |
| | STN | 0.0166; 0.0568 | cts | 0.1576; 0.2910 | |
| | SN | 0.0820; 0.2460 | | 0.0218; 0.0747 | cts |
| SN → | CPu | 0.1706; 0.3149 | | 0.1818; 0.2911 | |
| | SN | $5.4954 \times 10^{-4}$; 0.0066 | * | 0.0075; 0.0450 | * |
| | THL | 0.1998; 0.3198 | | 0.1248; 0.2723 | |
| THL → | THL | 0.9575; 0.9575 | | 0.9271; 0.9271 | |
| | CTX | 0.6068; 0.6905 | | 0.4298; 0.4912 | |
| CTX → | CPu | 0.6617; 0.6905 | | 0.3236; 0.4513 | |
| | STN | 0.1111; 0.2704 | | 0.0590; 0.1573 | |
| | THL | 0.0115; 0.0460 | * | 0.5819; 0.6348 | |
| | CTX | 0.4119; 0.5815 | | 0.0102; 0.0487 | * |

FIG. 20
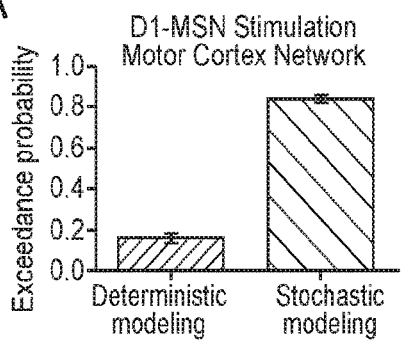
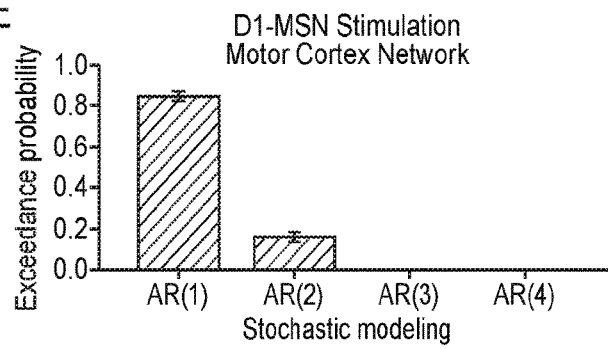
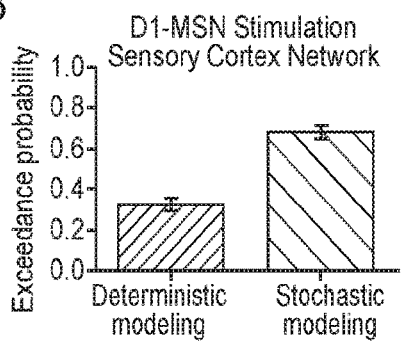
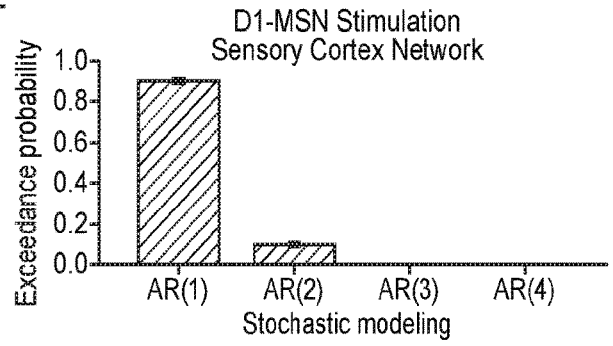
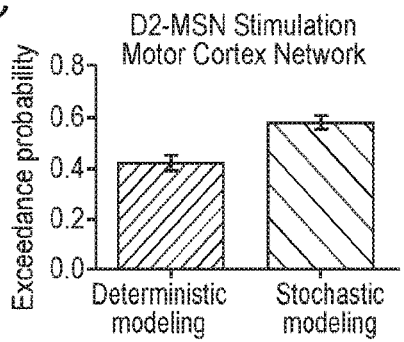
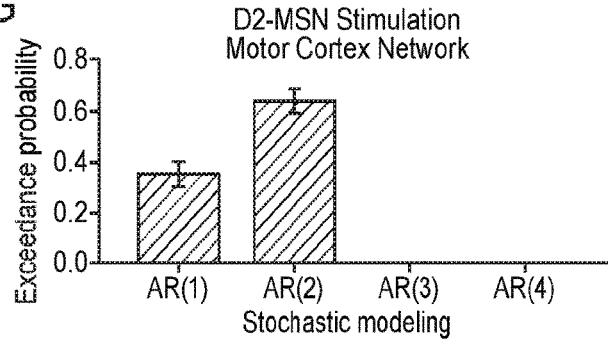
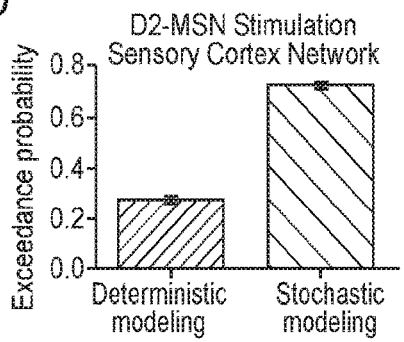
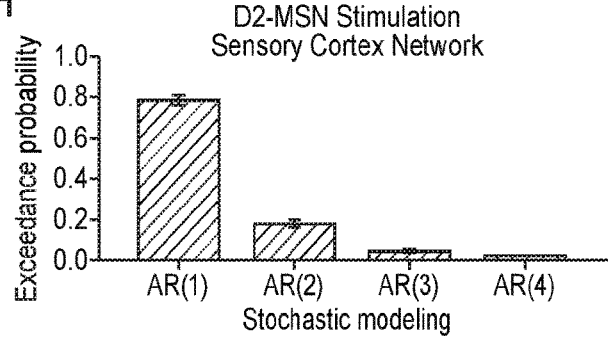

METHOD AND SYSTEMS FOR ANALYZING FUNCTIONAL IMAGING DATA

CROSS-REFERENCE TO RELATED APPLICATIONS

This application is a National Phase entry of International Application No. PCT/US2017/015659, filed Jan. 30, 2017, which claims the benefit of U.S. Provisional Application No. 62/289,741, filed Feb. 1, 2016, the disclosures of which are incorporated herein by reference.

STATEMENT REGARDING FEDERALLY SPONSORED RESEARCH

This invention was made with Government support under contract NS091461 awarded by the National Institutes of Health. The Government has certain rights in the invention.

INTRODUCTION

Neuroscience studies have shown that specific cell types within a brain network have unique contributions to the behavioral output. Distinct cell types within the same regions of the brain have been shown to drive distinct, and sometimes even opposite behaviors.

Neuroanatomical studies have also shown that even a single neuron can make connections to large portions of the brain. Furthermore, there are many circuits in the brain that function through global networks of connected cells, such as in the case of basal ganglia-thalamocortical circuits.

Optogenetic functional magnetic resonance imaging (ofMRI) is a technology that combines optogenetic stimulation with fMRI readout. Optogenetics enables cell type specific, millisecond-scale, activity modulation using light, while high-field fMRI measures resulting responses in live subjects across the whole brain.

SUMMARY

Methods and systems for analyzing brain functional activity data are provided. A method of the present disclosure may include obtaining functional activity data for a region of a brain of an individual, where the functional activity data represent a collective activity of neurons in the region; and estimating relative activities of neural pathways regulated by a plurality of neuronal subtypes by i) generating a connectivity model from the functional activity data based on a network model of functional connections among interconnected nodes representing the region, where the interconnected nodes include a node corresponding to each of the neuronal subtypes; and ii) linear regression between a) the connectivity model and b) neuronal subtype-specific connectivity estimates among the interconnected nodes, where the set of coefficients of the regression represent the contribution to the functional activity data of a neural pathway regulated by each of the distinct neuronal subtypes. Also provided are systems that find use in performing the present methods.

The present disclosure provides a method comprising: a) obtaining functional activity data for a region of a brain of a first individual, wherein the functional activity data represent a collective activity of a plurality of neurons in the region; and b) estimating relative activities of neural pathways regulated by each of a plurality of neuronal subtypes by computationally processing the functional activity data, wherein the computational processing comprises: i) generating a connectivity model from the functional activity data based on a network model of functional connections among interconnected nodes representing the region, wherein the interconnected nodes comprise a node corresponding to each of the plurality of neuronal subtypes; and ii) deriving a set of coefficients from a linear regression between a) the connectivity model; and b) neuronal subtype-specific connectivity estimates among the interconnected nodes, wherein the set of coefficients of the regression represent the contribution to the functional activity data of a neural pathway regulated by each of the plurality of distinct neuronal subtypes. In some cases, the functional activity data is resting-state functional activity data. In some cases, each of the neuronal subtypes comprises neurons categorized by neuronal identity. In some cases, the neuronal identity comprises expression of neuronal subtype-specific marker and/or neuronal subtype-specific spatial location. In some cases, each of the neuronal subtypes comprises neurons categorized by activity pattern. In some cases, the activity pattern comprises neuronal subtype-specific frequency, duration, and/or magnitude of activity. In some cases, the generating step comprises using dynamic causal modeling (DCM) to generate a DCM connectivity model. In some cases, the DCM is spectral DCM (spDCM). In some cases, the spDCM comprises stochastic modeling. In some cases, the generating comprises using neural mass modeling (NMM). In some cases, the functional activity data is obtained by functional magnetic resonance imaging (fMRI), magentoencephalography (MEG), and/or electroencephalography (EEG). In some cases, the obtaining comprises measuring functional activity of the region using fMRI, MEG, and/or EEG, to obtain the functional activity data. In some cases, the deriving step comprises using a general linear model, linear least squares regression, robust linear regression, support vector machine, quadratic programming, or ridge regression. In some cases, the region of the brain comprises the thalamus, cortex, ventral tegmental area (VTA), prefontal cortex (PFC), nucleus accumbens (NAc), amygdala (BLA), substantia nigra (SN), ventral pallidum, globus pallidus, dorsal striatum, ventral striatum, subthalamic nucleus (STN), anterior caudate putamen (CPu), globus pallidus external (GPe), globus pallidus internal (GPi), hippocampus, dentate gyrus, cingulate gyrus, entorhinal cortex, olfactory cortex, motor cortex, cerebellum, or combinations thereof. In some cases, the neuronal subtypes comprise neurons of the thalamus, cortex, ventral tegmental area (VTA), prefontal cortex (PFC), nucleus accumbens (NAc), amygdala (BLA), substantia nigra (SN), ventral pallidum, globus pallidus, striatum, dorsal striatum, ventral striatum, subthalamic nucleus (STN), anterior caudate putamen (CPu), globus pallidus external (GPe), globus pallidus internal (GPi), hippocampus, dentate gyrus, cingulate gyms, entorhinal cortex, olfactory cortex, motor cortex, or cerebellum. In some cases, the neuronal subtypes comprise medium spiny neurons. In some cases, the neuronal subtypes comprise dopaminergic, cholinergic, gamma-aminobutyric acid- (GABA)ergic, glutamatergic, or peptidergic neurons. In some cases, the neuronal subtypes comprise neurons expressing dopamine receptor subtypes, metabotropic glutamate receptor subtypes, ionotropic glutamate receptor subtypes, metabotropic acetylcholine receptor subtypes, ionotropic acetylcholine receptor subtypes, $GABA_A$ receptor subtypes, and $GABA_B$ receptor subtypes. In some cases, the neuronal subtype-specific connectivity estimate is derived from a different species of organism than the species of organism to which the first individual belongs. In some cases, the first individual is a human individual. In some cases, the first individual is a healthy individual. In some cases, the first individual has a neurological disorder. In some cases, the neurological disorder is a neurological disease, or an age-related neurological disorder. In some cases, the neurological disease is Parkinson's disease, Alzheimer's disease, dementia, epilepsy, autism, bipolar disorder, schizophrenia, Tourette's syndrome, obsessive compulsive disorder, attention deficit hyperactivity disorder, Huntington's disease, multiple sclerosis, or migraine. In some cases, the estimating step further comprises: iii) generating the neuronal subtype-specific connectivity estimates before the deriving (ii). In some cases, generating the neuronal subtype-specific connectivity estimates comprises, for each neuronal subtype: obtaining neuronal subtype functional activity data for the region of a brain of one or more second individuals, wherein the region of the brain of the one or more second individuals corresponds to the region of the brain of the first individual, and wherein the functional activity data represent a collective activity of a plurality of neurons in the region of the brain of the one or more second individuals caused by selective activity modulation of neurons of the neuronal subtype in the brain of the one or more second individuals; generating, for each of the plurality of neuronal subtypes, a neuronal subtype-specific connectivity model from the neuronal subtype functional activity data based on the network model; and estimating the connectivity among the interconnected nodes of the network model for each of the plurality of neuronal subtypes based on an average across the one or more second individuals of the neuronal subtype-specific connectivity model. In some cases, the neuronal subtype functional activity data is obtained by functional magnetic resonance imaging (fMRI), magentoencephalography (MEG), and/or electroencephalography (EEG). In some cases, obtaining the neuronal subtype functional activity data comprises measuring functional activity of the region using fMRI, MEG, and/or EEG, to obtaining the neuronal subtype functional activity data. In some cases, neurons of the neuronal subtype in the one or more second individuals selectively express a light-activated polypeptide configured to modulate the activity of the neurons when the neurons are illuminated by an activating light stimulus. In some cases, the obtaining comprises, for each of the plurality of neuronal subtypes in the one or more second individuals: illuminating neurons of the neuronal subtype with an activating light stimulus; and measuring functional activity of the region, thereby generating the neuronal subtype functional activity data. In some cases, generating the neuronal subtype-specific connectivity model comprises using dynamic causal modeling (DCM) to generate a neuronal subtype-specific DCM connectivity model. In some cases, the DCM is spectral DCM (spDCM). In some cases, the spDCM comprises stochastic modeling.

The present disclosure provides a method of identifying a neural circuit-level biomarker associated with a neurological disorder, the comprising: i) estimating relative activities of neural pathways regulated by each of a plurality of neuronal subtypes by performing the method, as described above or elsewhere herein, in each first individual of a plurality of groups of first individuals, the plurality of groups comprising: a case group of first individuals having the neurological disorder; and a control group of first individuals, thereby generating a plurality of sets of regression coefficients comprising: a case set of regression coefficients representing the contribution to a case functional activity data of the neural pathway regulated by each of the plurality of distinct neuronal subtypes in the case group; and a control set of regression coefficients representing the contribution to a control functional activity data of the neural pathway regulated by each of the plurality of distinct neuronal subtypes in the control group; ii) calculating a difference measurement between the case set and the control set of regression coefficients; and iii) determining that the case set of regression coefficients is a neural circuit-level biomarker associated with the neurological disorder when the difference measurement for one or more regression coefficients meets a threshold criterion, or determining that the case set of regression coefficients is not a neural circuit-level biomarker associated with the neurological disorder when the difference measurement for one or more regression coefficients does not meet the threshold criterion. In some cases, the control group comprises individuals not having the neurological disorder. In some cases, the case group comprises individuals having a neurological disorder and to whom a treatment for the neurological disorder has been administered, and the control group comprises individuals having a neurological disorder and to whom a treatment for the neurological disorder has not been administered.

The present disclosure provides a method of treating an individual for a neurological disease, the method comprising: i) estimating relative activities of neural pathways regulated by each of a plurality of neuronal subtypes in a brain of a first individual by performing the method as described above or elsewhere herein, wherein the first individual has a neurological disorder; ii) stimulating a region of the brain in a manner sufficient to modulate the activity of neurons of one or more of the plurality of neuronal subtypes based on the estimated relative activities. In some cases, the neurological disorder is a neurological disease, or an age-related neurological disorder. In some cases, the neurological disease is Parkinson's disease, Alzheimer's disease, dementia, epilepsy, autism, bipolar disorder, schizophrenia, Tourette's syndrome, obsessive compulsive disorder, attention deficit hyperactivity disorder, Huntington's disease, multiple sclerosis, or migraine.

The present disclosure provides a system, comprising: a magnetic resonance imaging (MRI) device, a processor; and a non-transient computer-readable medium comprising instructions that, when executed by the processor, cause: the MRI device to record a functional activity of a brain of an individual, thereby generating functional activity data for a region of the brain; and the processor to perform the method as described above, or elsewhere herein, using the generated functional activity data. In some cases, the system further comprises a deep brain stimulation device, or a transcranial magnetic stimulation device. In some cases, the system further comprises a user interface and a data connector that transmits data from the processor to the user interface.

BRIEF DESCRIPTION OF THE DRAWINGS

FIG. 5, panels A-F are a collection of graphs showing that neuronal activity mirrors the polarity of fMRI responses evoked in striatum and thalamus during D1- and D2-MSN stimulations, according to embodiments of the present disclosure.

FIG. 9, panels A and B, show anatomical masks for time series extraction and model estimation of the MCX (panel A) and SCX (panel B) network models, respectively. FIG. 9, panels C and D, show time series extracted from regions of interest (ROIs) of the left (ipsi-stimulation) hemisphere during D1- and D2-MSN stimulations, respectively. The time series were zero-mean and represented the average signal changes across all voxels and subjects (panel C; D1-MSN stimulation: n=12 and panel D; D2-MSN stimulation: n=11). The error bars represent the SEM activation values across subjects. The blue rectangles overlying time series represent the 20 second periods of optogenetic activation, delivered every minute for 6 min.

FIG. 10, panels A and B, show a schematic representation and a graphical representation of a basal ganglia-thalamocortical network model, according to embodiments of the present disclosure. FIG. 10, panel A, shows a schematic representation of the a priori generative network model. u(t) denotes input to the CPu network node modeling optogenetic stimulation. FIG. 10, panel B, shows a graphical representation of the matrix A that described extrinsic (between region) anatomical connections.

FIG. 11, panels A and B, show graphs of significant and close-to-significant effective connections during D1-MSN stimulations for MCX and SCX network models, respectively. FIG. 11, panels C and D, show graphs of significant and close-to-significant effective connections during D2-MSN stimulations for MCX and SCX network models, respectively. Substantial variability in the p-values of some connectivity estimates across cutoff frequencies was observed. In all panels, statistical significance was determined by testing effective connectivity strengths across subjects. Significant, $P<0.05$; Close-to-significant, $P<0.10$. FIG. 11, panels E and F, show graphs of weighted sum number of significant and close-to-significant connections during D1-MSN stimulations for MCX and SCX network models, respectively. The optimal cutoff frequencies, marked with a vertical dashed line, were 0.29 and 0.24 Hz, respectively. FIG. 11, panels G and H, show graphs of weighted sum number of significant and close-to-significant connections during D2-MSN stimulations for MCX and SCX network models, respectively. The optimal cutoff frequencies, marked with a vertical dashed line, were 0.27 and 0.22 Hz, respectively.

FIG. 12, panels A and D are schematics showing significant connections during D1-MSN stimulations for MCX (FIG. 12, panel A) and SCX (FIG. 12, panel D) network models, respectively. The greatest connections for either model were from CPu to GPi and SN, which defined the direct pathway. The matrices to the right of each network schematic show a graphical representation of significant connections. For simplicity, self-connections were not included. The significance levels were corrected for multiple comparisons by FDR. FIG. 12, panels B and E are graphs showing observed and predicted BOLD responses for MCX (FIG. 12, panel B) and SCX (FIG. 12, panel E) network models, respectively. The predicted responses closely fit the observed time series. FIG. 12, panels C and F show that, according to Bayesian model selection, the stochastic modeling fits the observed BOLD responses better than the deterministic modeling for both MCX (FIG. 12, panel C) and SCX (FIG. 12, panel F) networks.

FIG. 13 shows Table 3, which is related to FIG. 12. FIG. 13 shows a table of connectivity estimates, 95% confidence intervals across subjects, and statistical significance levels for the D1-MSN simulation network model, according to embodiments of the present disclosure. Significant connections reflected the direct pathway. Asterisks indicate significant connectivity estimate after multiple comparison correction (* $P<0.05$,  $P<0.005$, * $P<0.001$); "cts" indicates close-to-significant connectivity estimate after multiple comparison correction.

FIG. 14, panels A and D, are schematics showing significant connections during D2-MSN stimulations for MCX (FIG. 14, panel A) and SCX (FIG. 14, panel D) network models, respectively. The connection from GPe to STN, which in part defines the indirect pathway, was the greatest connection within either model. The matrices to the right of each network schematic provide a graphical representation of connection strengths. For simplicity, self-connections were not included. The significance levels were corrected for multiple comparisons by FDR. FIG. 14, panels B and E, show graphs of observed and predicted BOLD responses for MCX (FIG. 14, panel B) and SCX (FIG. 14, panel E) network models, respectively. The predicted responses closely fit the observed time series. FIG. 14, panels C and F, show that, according to Bayesian model selection, the stochastic modeling fit the observed BOLD responses better than the deterministic modeling in a majority of animals for both MCX (FIG. 14, panel C) and SCX (FIG. 14, panel F) network models.

FIG. 15 shows Table 4, which is related to FIG. 14. FIG. 15 shows a table of connectivity estimates, 95% confidence intervals across subjects, and statistical significance levels for the D2-MSN simulation network model, according to embodiments of the present disclosure. Significant connections reflected the indirect pathway. Asterisks indicate significant connectivity estimate after multiple comparison correction (* $P<0.05$,  $P<0.005$, * $P<0.001$). "cts"

indicates close-to-significant connectivity estimate after multiple comparison correction.

Figure 16:
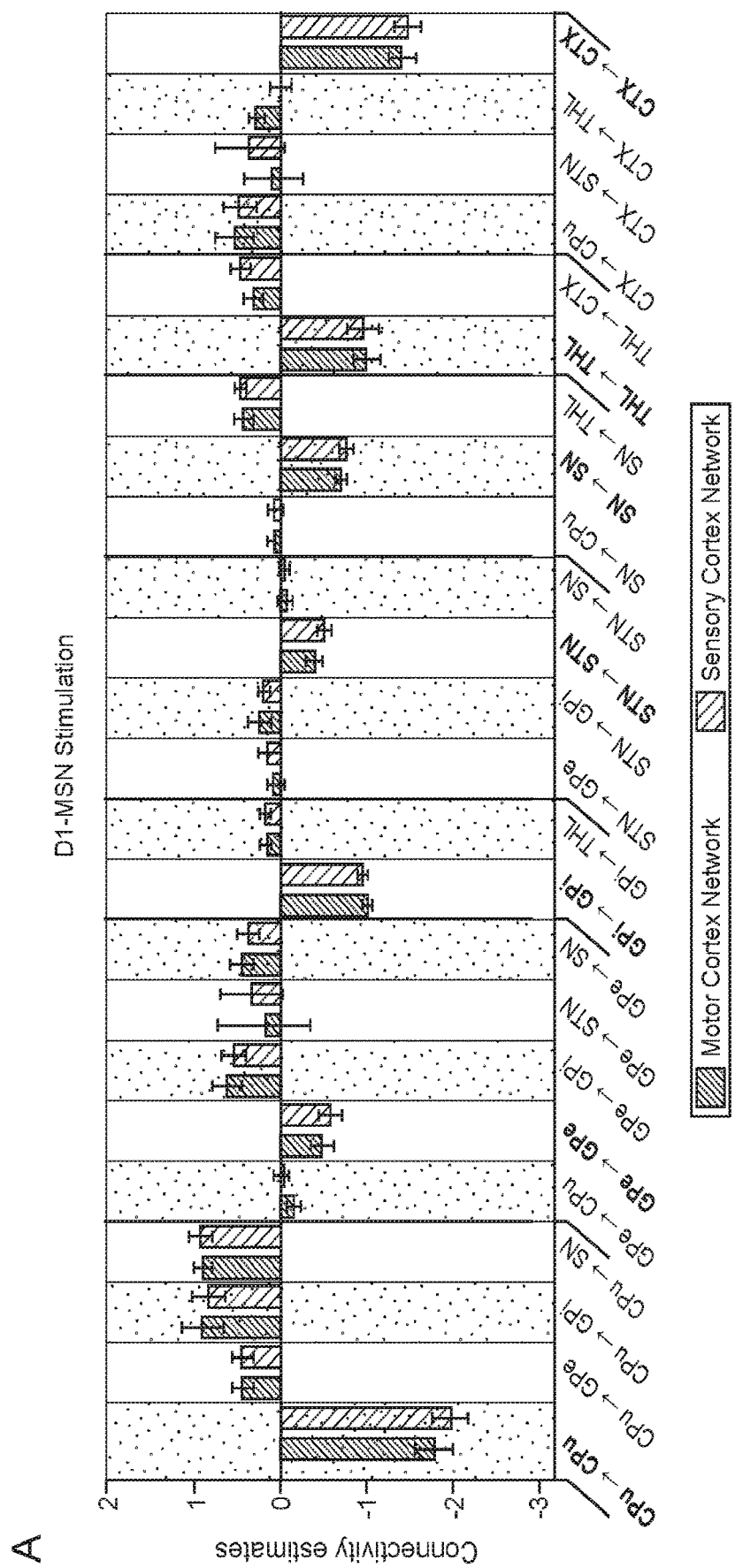
Figure 16:
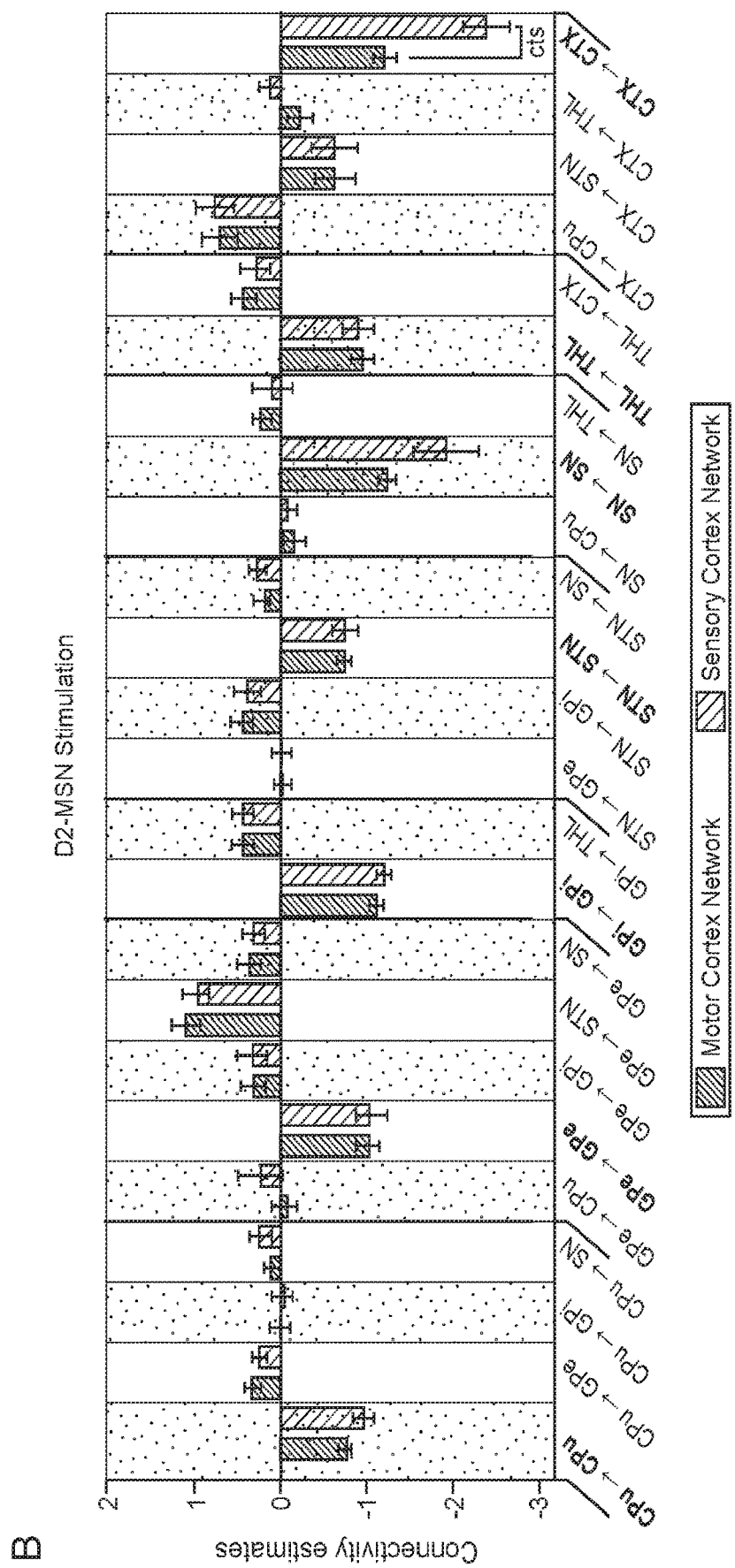

FIG. 16, panels A and B, show graphs of a comparison of connectivity estimates between MCX and SCX network models, according to embodiments of the present disclosure. FIG. 16, panel A, shows a graph of a comparison of connectivity estimates during D1-MSN stimulations between MCX and SCX network models. No significant differences were observed in the connectivity estimates during D1-MSN stimulations between MCX and SCX network models. FIG. 16, panel B, shows a graph of a comparison of connectivity estimates during D2-MSN stimulations between MCX and SCX network models. No differences were observed in the connectivity estimates during D2-MSN stimulations with the exception of the self-connection within CTX. The error bars represent the SE of the connectivity estimates over subjects. "cts" indicates a close-to-significant difference across subjects after applying a multiple comparison correction across a priori connections with FDR (p<0.10).

FIG. 17 shows Table 5, which is related to FIG. 16. FIG. 17 shows a table of statistical comparisons of connectivity estimates between MCX and SCX network models, according to embodiments of the present disclosure. No significant differences were observed. "cts" indicates close-to-significant difference after multiple comparison correction.

Figure 18:
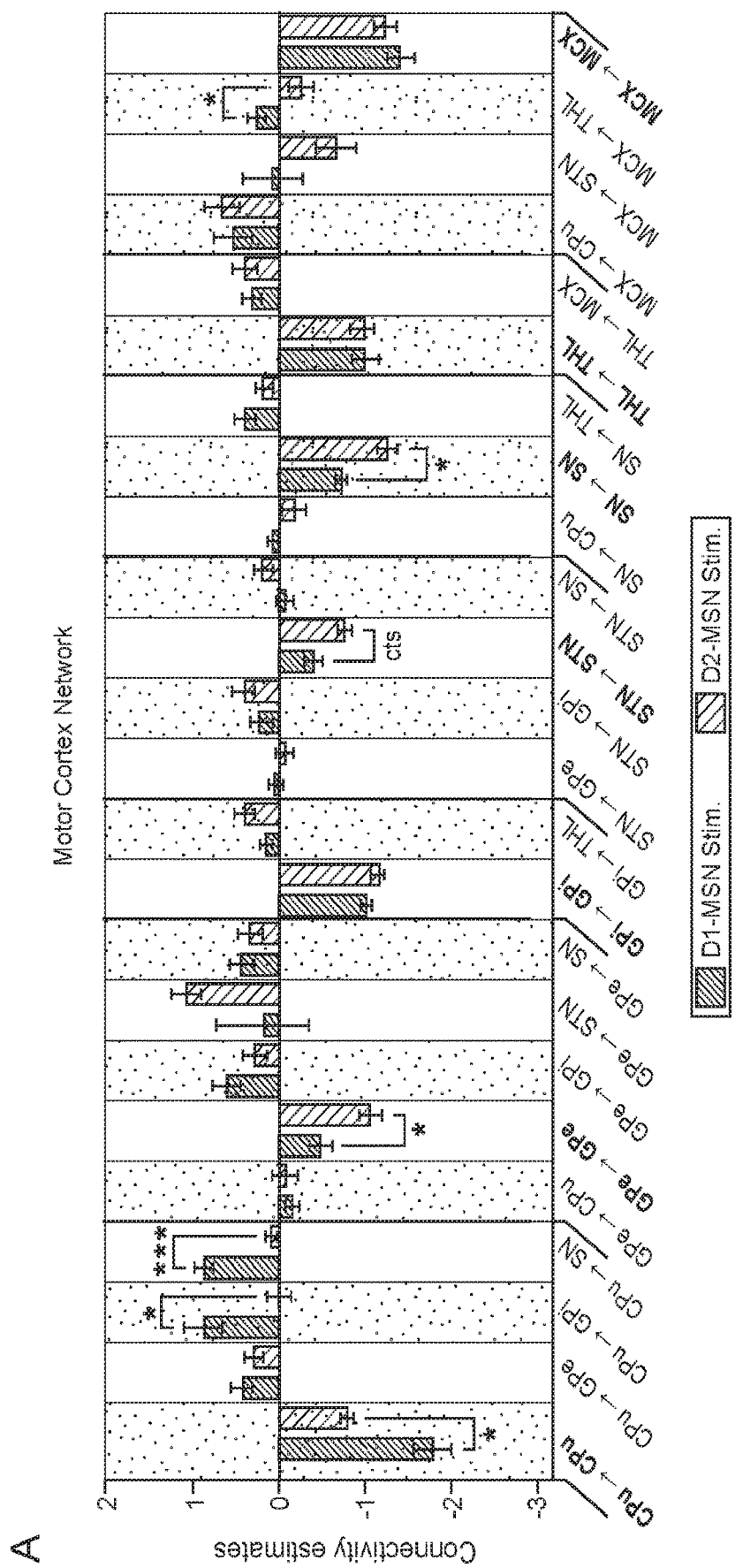
Figure 18:
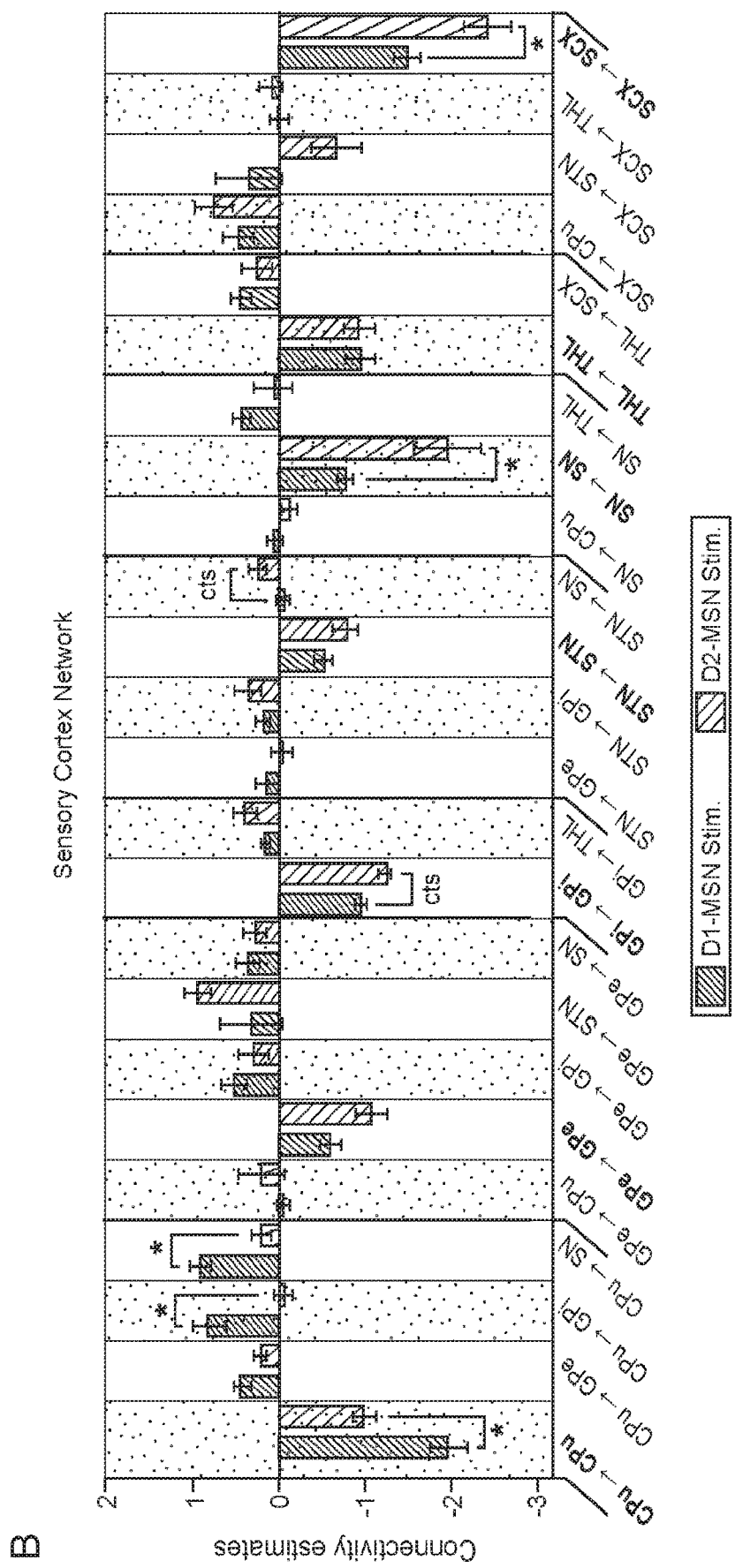

FIG. 18 shows graphs of a comparison of connectivity estimates between D1- and D2-MSN stimulation network models, according to embodiments of the present disclosure. FIG. 18, panel A, shows a graph of a comparison of connectivity estimates between D1- and D2-MSN stimulations for the MCX network model. The statistical differences were observed in the connectivity estimates between D1- and D2-MSN stimulations. FIG. 18, panel B, shows a graph of a comparison of connectivity estimates between D1- and D2-MSN stimulations for the SCX network model. The statistical differences were observed in the connectivity estimates between D1- and D2-MSN stimulations. The error bars represent the SE of the connectivity estimates over subjects. * indicates p<0.05 and *** indicates p<0.001 across subjects after applying a multiple comparison correction across a priori connections with FDR and "cts" indicates a close-to-significant difference (p<0.10).

FIG. 19 shows Table 6, which is related to FIG. 18. FIG. 19 shows a table of statistical comparisons of connectivity estimates between D1- and D2-MSN stimulation network models, according to embodiments of the present disclosure. Asterisks indicate significant connectivity estimate after multiple comparison correction (* P<0.05, *** P<0.001). "cts" indicates close-to-significant difference after multiple comparison correction.

Figure 12:
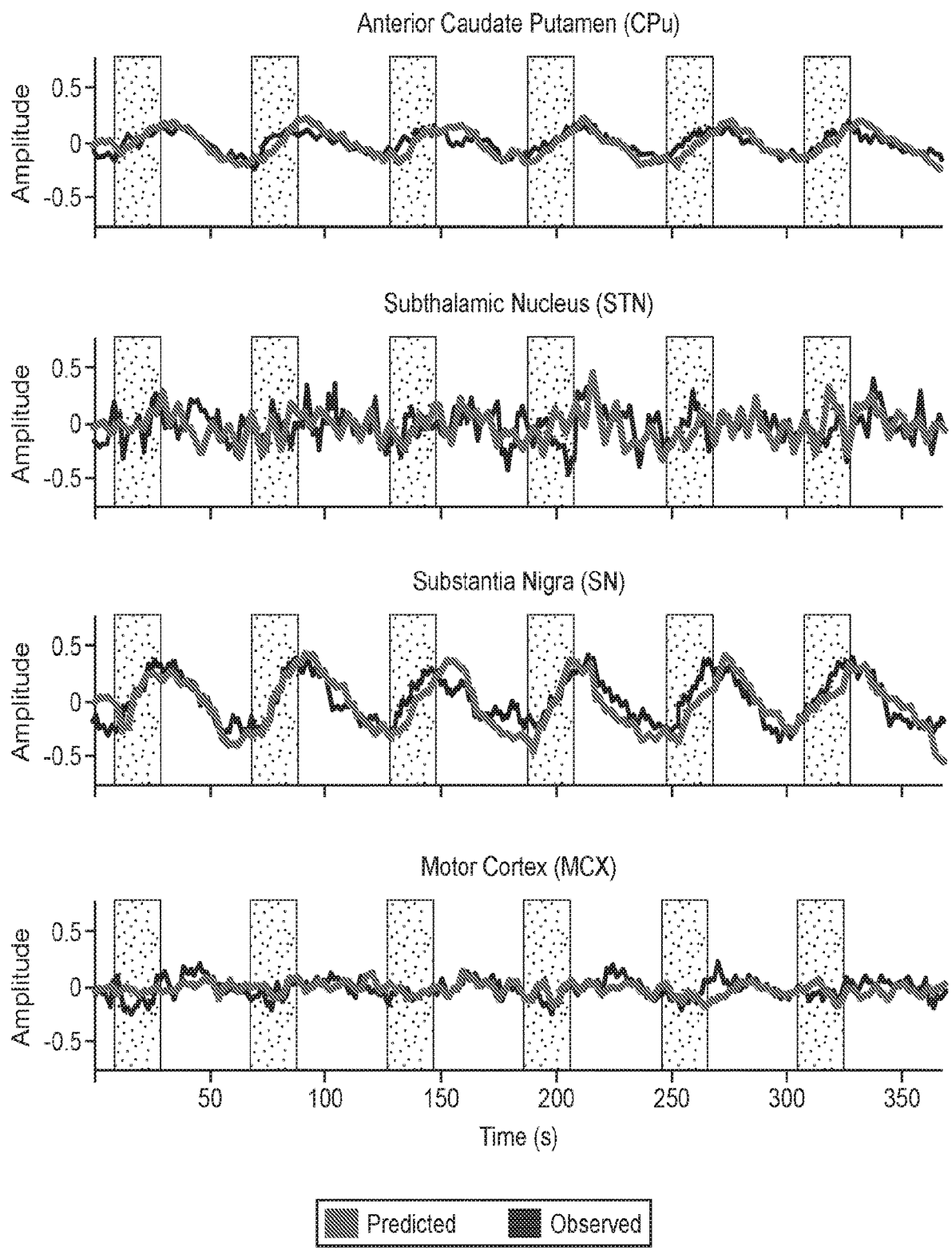
FIG. 12, panels A-F, are a collection of schematics and graphs demonstrating that the D1-MSN stimulation network shows connectivity estimates consistent with the direct pathway, according to embodiments of the present disclosure.
Figure 12:
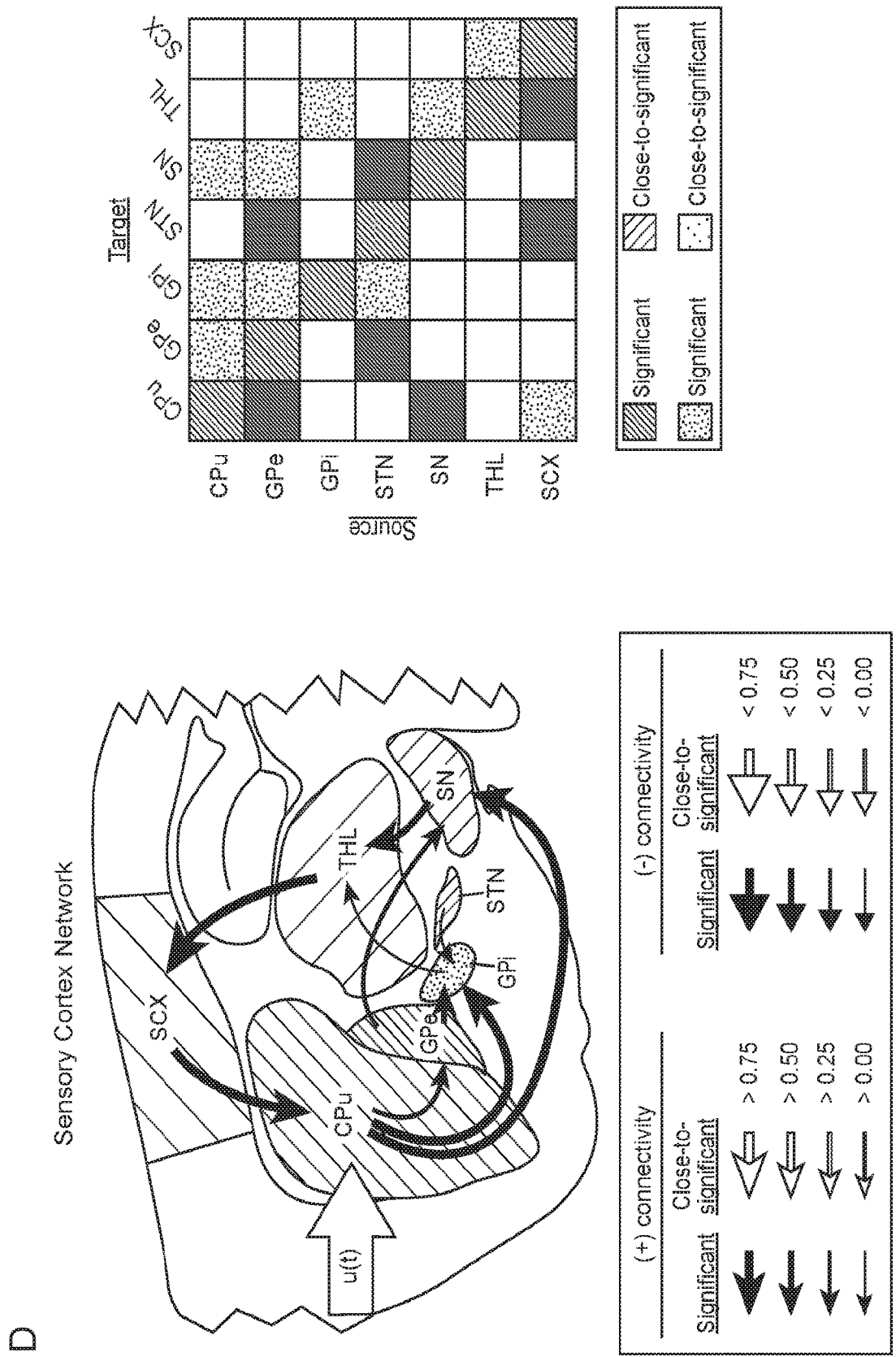
Figure 12:
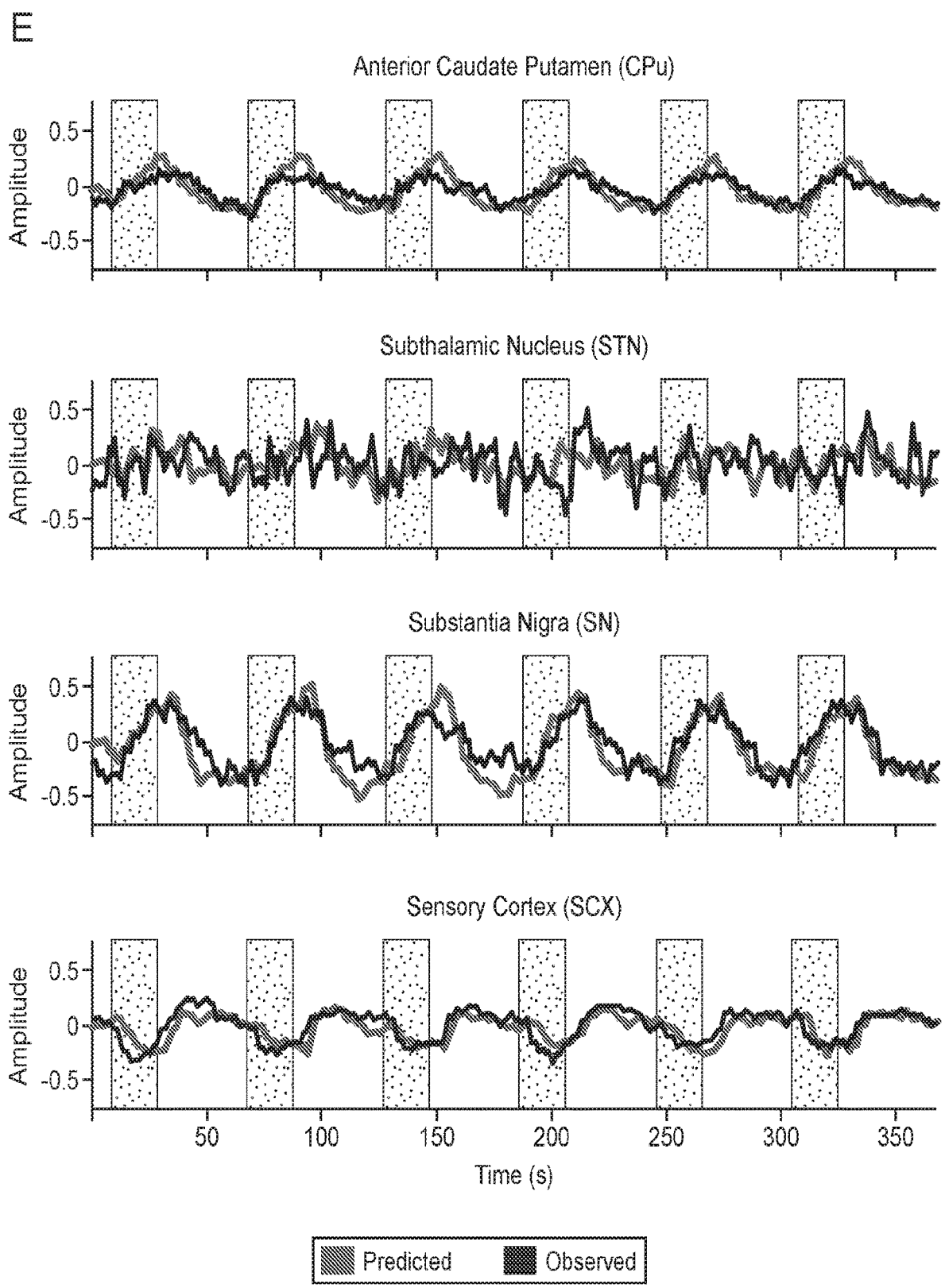
Figure 14:
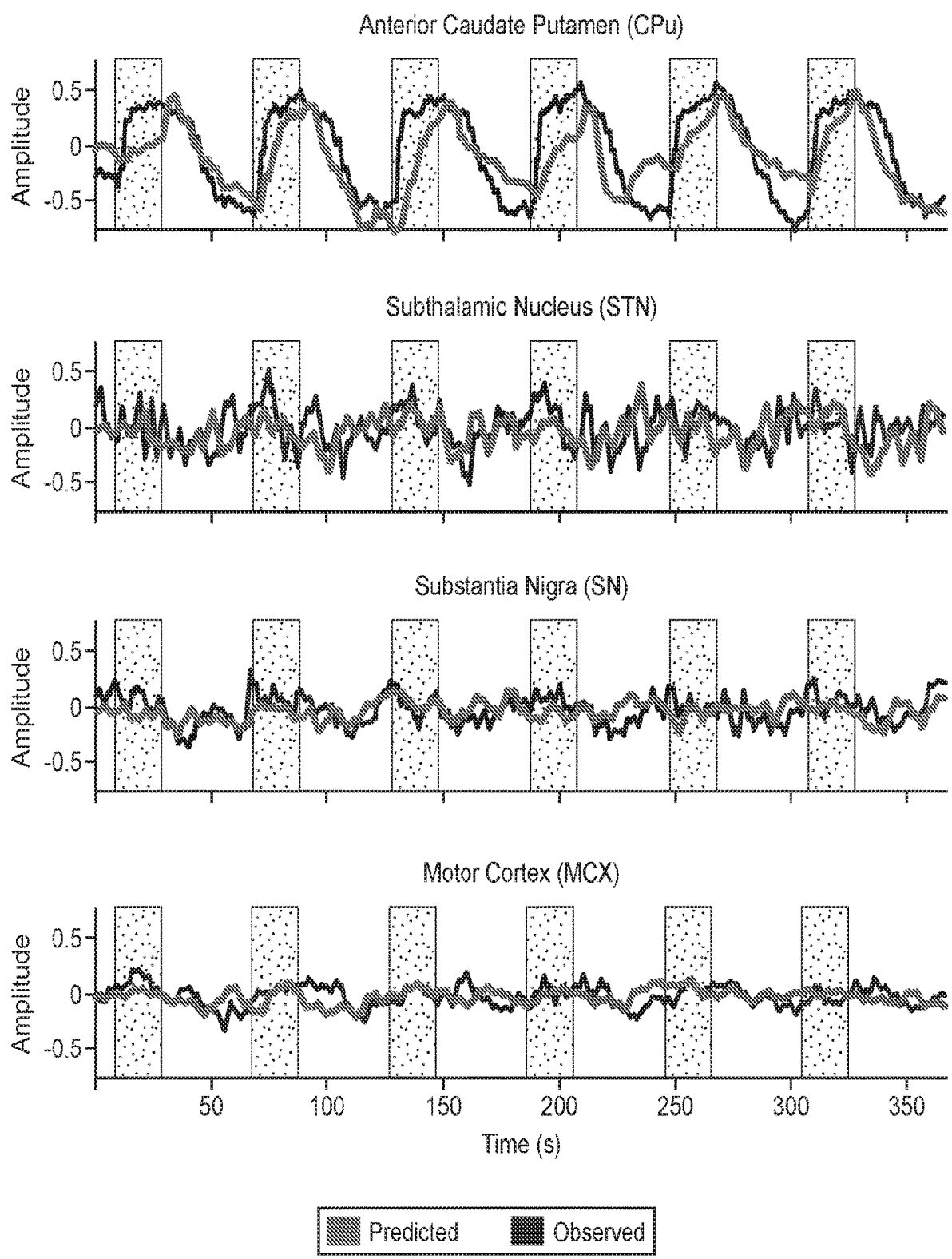
FIG. 14, panels A-F, are a collection of schematics and graphs demonstrating that the D2-MSN stimulation network shows connectivity estimates consistent with the indirect pathway, according to embodiments of the present disclosure.
Figure 14:
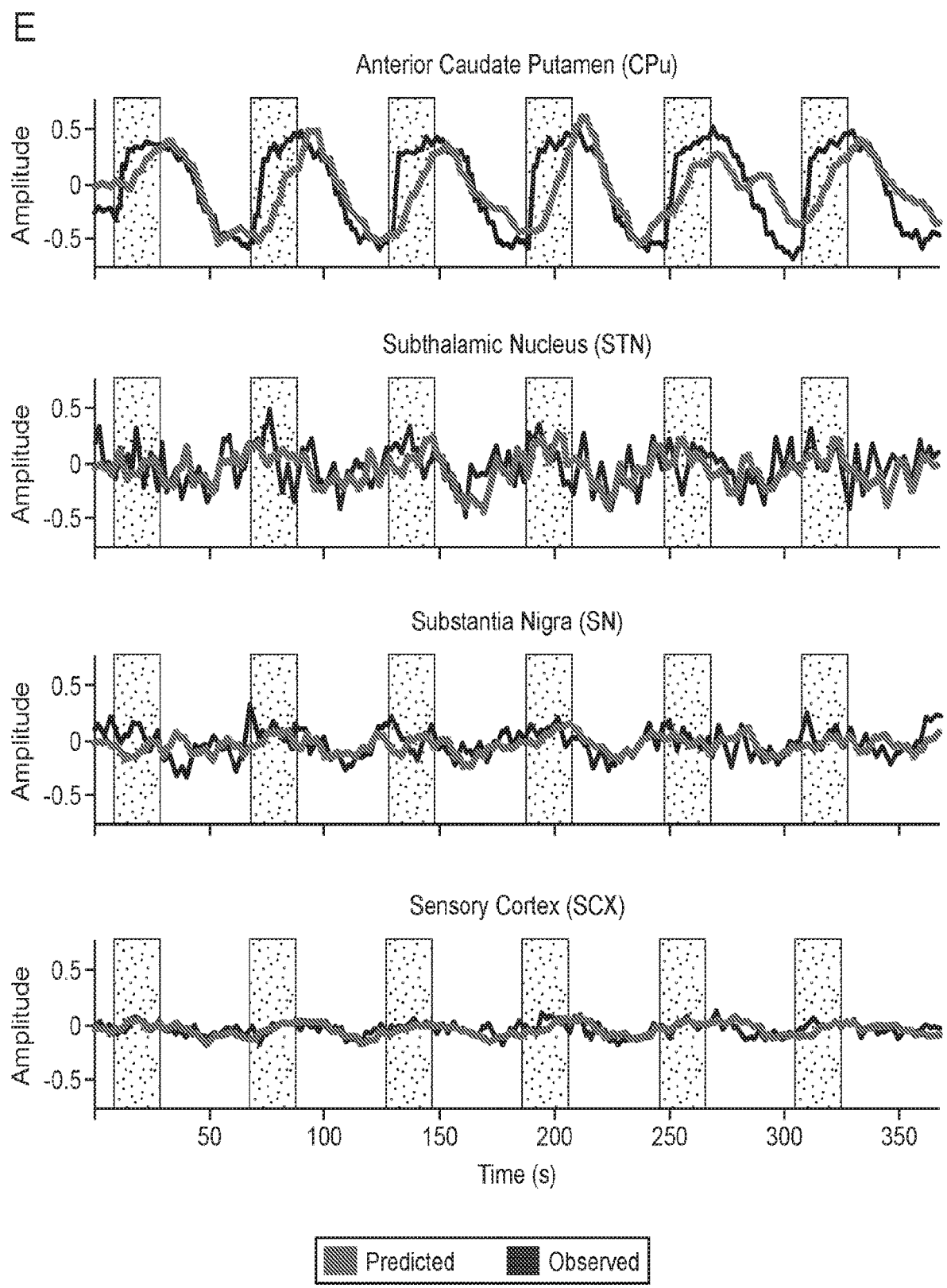

FIG. 20, panels A-H, is related to FIGS. 12 and 14. FIG. 20 shows a comparison between deterministic and stochastic modeling and evaluation of autoregressive models under stochastic assumptions across cutoff frequencies, according to embodiments of the present disclosure. FIG. 20, panels A-D, show graphs of a comparison of model exceedance probabilities between deterministic and stochastic modeling. FIG. 20, panels E-H, shows graphs of a comparison of model exceedance probabilities of autoregressive processes under stochastic assumptions. Error bars represent the standard error of the mean exceedance probabilities across cutoff frequencies.

DEFINITIONS

The terms "polypeptide", "peptide" and "protein" are used interchangeably herein to refer to polymers of amino acids of any length. The polymer may be linear, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" refers to either natural and/or unnatural or synthetic amino acids, including glycine and both the D or L optical isomers, and amino acid analogs and peptidomimetics.

The term "genetic modification" refers to a permanent or transient genetic change induced in a cell following introduction into the cell of a heterologous nucleic acid (e.g., a nucleic acid exogenous to the cell). Genetic change ("modification") can be accomplished by incorporation of the heterologous nucleic acid into the genome of the host cell, or by transient or stable maintenance of the heterologous nucleic acid as an extrachromosomal element. Where the cell is a eukaryotic cell, a permanent genetic change can be achieved by introduction of the nucleic acid into the genome of the cell. Suitable methods of genetic modification include viral infection, transfection, conjugation, protoplast fusion, electroporation, particle gun technology, calcium phosphate precipitation, direct microinjection, and the like.

A "plurality" contains at least 2 members. In certain cases, a plurality may have at least 10, at least 100, at least 1000, at least 10,000, at least 100,000, at least $10^6$, at least $10^7$, at least $10^8$ or at least $10^9$ or more members.

An "individual" as used herein, may be any suitable animal amenable to the methods and techniques described herein, where in some cases, the individual may be a vertebrate animal, including a mammal, bird, reptile, amphibian, etc. The individual may be any suitable mammal, e.g., human, mouse, rat, cat, dog, pig, horse, cow, monkey, non-human primate, etc.

"Dynamic" as used herein, may be used to describe a time varying property of a system.

"Static" as used herein, may be used to describe a property of a system without regard to any time dependence of the property.

"Functional activity", as used herein, may refer to a time-varying measure of a change in a first component of a system, where the change has a specific effect on a second component of the system.

"Neuronal subtype" as used herein, may refer to a classification of neurons based on a static identity of a neuron, and/or a dynamic property of a neuron. A static identity of a neuron may include marker expression (e.g., mRNA transcript or protein expression), anatomical location and/or connection, etc. A dynamic property of a neuron may include the pattern (e.g., frequency, duration, timing, etc.) of depolarization/action potential firing). In some cases, a single neuron may belong to multiple subtypes, e.g., when a neuron exhibits distinct responses to different depolarizing stimulation patterns.

A "network" as used herein, may refer to a collection of nodes that are connected, directly, or indirectly, with one another through edges. "Direct" as used herein, may refer to a connection between two nodes with a single edge. "Indirect" as used herein, may refer to a connection between two nodes that requires at least two edges and at least a third intervening node. A single node within a network may be connected directly to one other node, some nodes, or all nodes of the network. A single node may be connected to one or more other nodes at certain times, and may not be connected to any nodes at other time. "Node" as used herein, may include a substantially functionally equivalent collection of elements, e.g., neurons. A subtype of neurons may define a node of a neural network. "Interconnected" as used herein, may be used to describe a collection of nodes where each node is directly connected to at least one other node.

"Connectivity" as used herein, may refer to a measure of the strength of a functional connection between two nodes of a network. The measure may reflect a structural aspect (e.g., the number of neuronal processes, the number of synaptic connections across one or more neurons), and/or may reflect a functional aspect (e.g., the strength of a synapse) of the connection.

A "neural pathway" as used herein, may refer to a functional state of a network of neurons defined by a specific distribution of connectivity among the nodes of the network. The functional state may be promoted or induced by specific activity of one or more subtypes of neurons in the network.

A "model" as used herein, may refer to a representation of a system (e.g., a collection of neurons forming a network) using a defined set of parameters, which in some cases may be generated based on empirical information having dimensionality that is lower than the number of the parameters. The representation may be an approximation of the real-life anatomical and/or functional properties of the system. A "connectivity model" may refer to a dynamic model representing the strength of the functional connection among nodes of a network. A "network model" may refer to a static representation of physical and functional connections among nodes of a network without regard to the strength of the connection (i.e., a representation of the topology of the network).

"Identity" as used herein, may refer to a static property of an object, e.g., a neuron. The static property may be expression of a marker, e.g., a receptor, by a cell or neuron.

"Neural activity" as used herein, may refer to electrical activity of a neuron (e.g., changes in membrane potential of the neuron), as well as indirect measures of the electrical activity of one or more neurons, e.g., neurons in a neural pathway. Thus, neural activity may refer to changes in field potential, changes in intracellular ion concentration (e.g., intracellular calcium concentration), and changes in magnetic resonance induced by electrical activity of neurons, as measured by, e.g., blood oxygenation level dependent (BOLD) signals in functional magnetic resonance imaging.

"Resting" or "resting-state", as used herein, may refer to an individual who is not performing an explicit, or an externally prompted task. Resting-state functional activity data, such as resting-state fMRI data, may refer to functional activity data collected from an individual who has not been instructed to perform an explicit task while the functional activity data was being collected.

As used herein, the term "difference measurement" refers to any measurement of the relationship (e.g., subtraction, division, correlation, deviation, etc.) between two values or vectors.

Before the present disclosure is further described, it is to be understood that the disclosed subject matter is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosed subject matter. The upper and lower limits of these smaller ranges may independently be included in the smaller ranges, and are also encompassed within the disclosed subject matter, subject to any specifically excluded limit in the stated range. Where the stated range includes one or both of the limits, ranges excluding either or both of those included limits are also included in the disclosed subject matter.

Unless defined otherwise, all technical and scientific terms used herein have the same meaning as commonly understood by one of ordinary skill in the art to which the disclosed subject matter belongs. Although any methods and materials similar or equivalent to those described herein can also be used in the practice or testing of the disclosed subject matter, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a neuron" includes a plurality of such neurons and reference to "the processor" includes reference to one or more processors and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the disclosed subject matter, which are, for clarity, described in the context of separate embodiments, may also be provided in combination in a single embodiment. Conversely, various features of the disclosed subject matter, which are, for brevity, described in the context of a single embodiment, may also be provided separately or in any suitable sub-combination. All combinations of the embodiments pertaining to the disclosure are specifically embraced by the disclosed subject matter and are disclosed herein just as if each and every combination was individually and explicitly disclosed. In addition, all sub-combinations of the various embodiments and elements thereof are also specifically embraced by the present disclosure and are disclosed herein just as if each and every such sub-combination was individually and explicitly disclosed herein.

The publications discussed herein are provided solely for their disclosure prior to the filing date of the present application. Nothing herein is to be construed as an admission that the disclosed subject matter is not entitled to antedate such publication by virtue of prior invention. Further, the dates of publication provided may be different from the actual publication dates which may need to be independently confirmed.

DETAILED DESCRIPTION

As summarized above, methods and systems for analyzing brain functional activity data are provided. In general terms, the present disclosure includes methods and systems for analyzing the response of a neuronal circuit to cell type- and/or frequency-specific activation of distinct neural pathways within the neuronal circuit, to construct models that describe the relationship between non-invasively monitored brain functional activity and the neuronal mechanisms underlying the same. The neuronal circuit response may be measured by a variety of methods, ranging from local field potential (LFP) or multiunit activity (MUA) recordings of regional neural circuit responses, to functional magnetic imaging (fMRI) of whole brain responses. In particular, the connectivity of the neuronal circuit that gives rise to cell type- and/or frequency-specific neural pathways may be estimated by the present method.

The present disclosure also includes methods and systems for estimating the cell type- and/or frequency-specific neural pathways underlying non-invasively measured brain functional activity of an individual, e.g., an individual in a resting state, by modeling a connectivity model derived from the measured brain functional activity as a linear combination of cell type- and/or frequency-specific neural pathways, such as those estimated from empirical measurement of neural circuit-level responses to cell type- and/or frequency-specific neuronal activity, as described above.

Thus, the present methods and systems may enable the quantitative characterization of neuronal mechanisms in the healthy and diseased human brain based on resting state brain functional activity data using validated neurobiophysical models in animals.

Methods

Figure 2A:
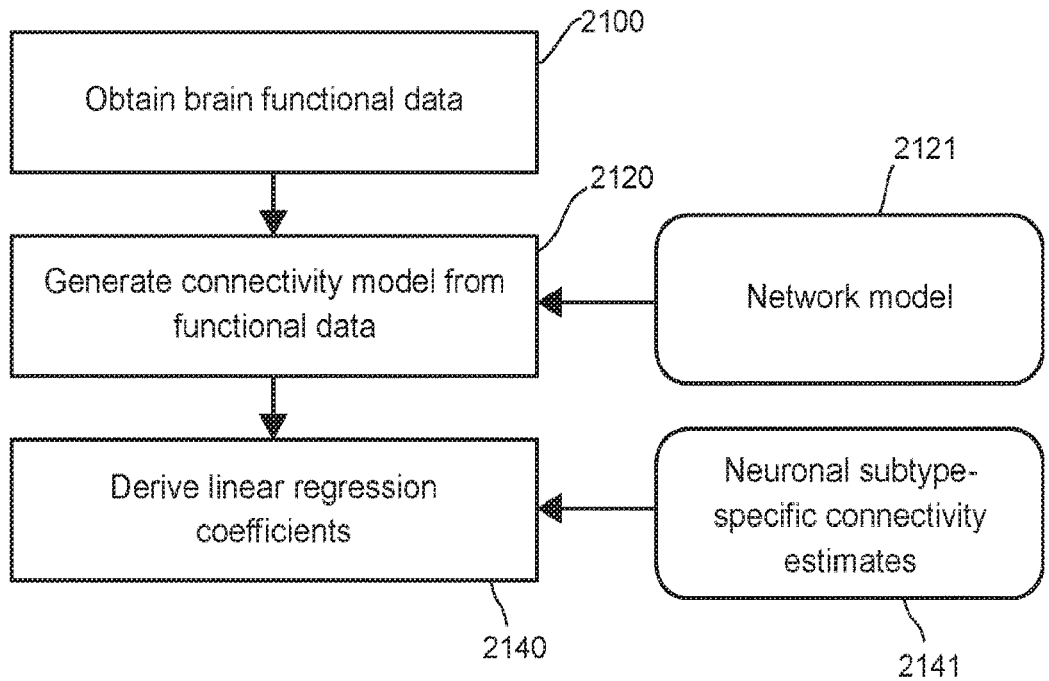
FIGS. 2A-2C are a collection of schematic diagrams depicting embodiments of methods and systems of the present disclosure.
Figure 6:
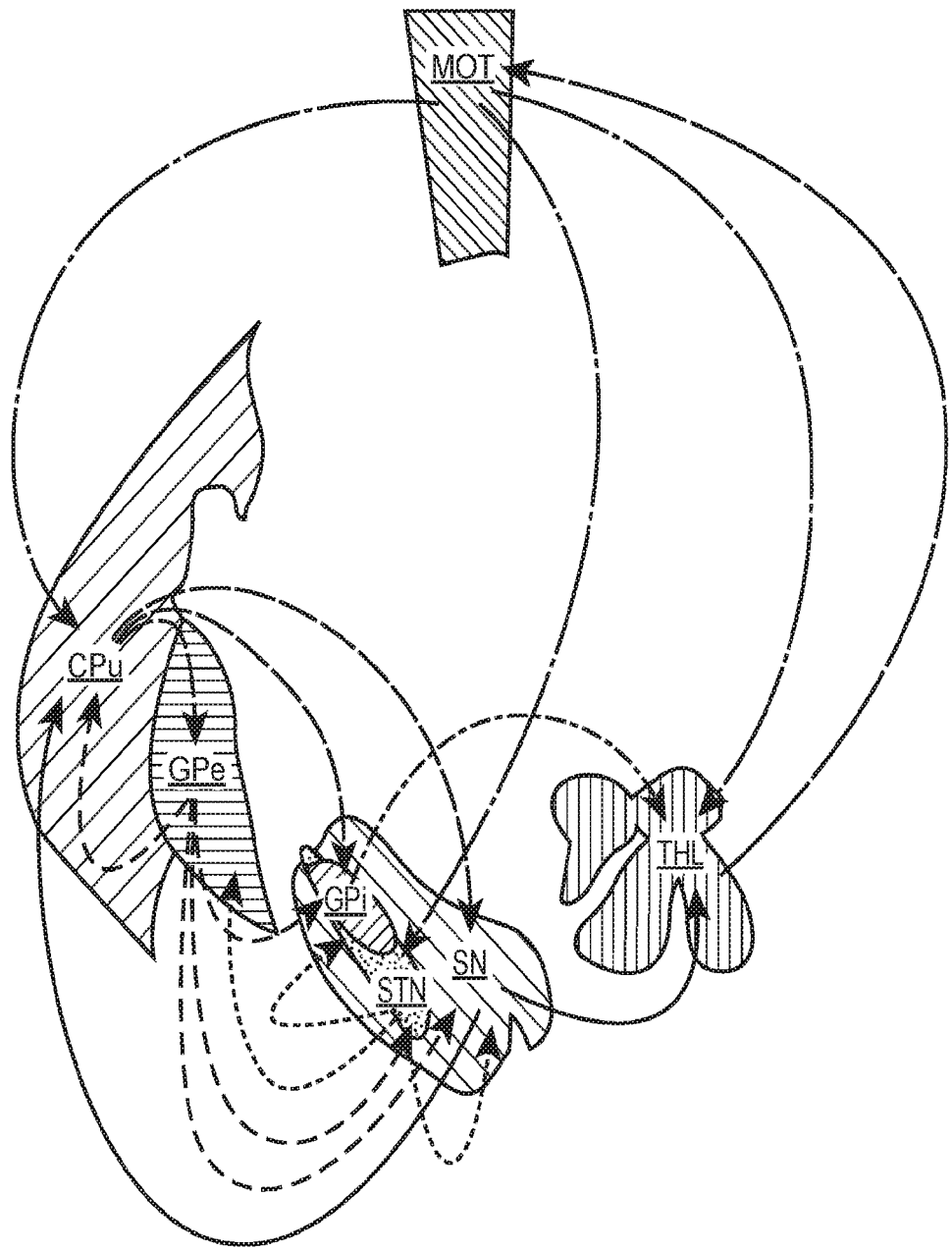
FIG. 6 is a schematic diagram showing a network model of the basal ganglia-thalamocortical complex, according to embodiments of the present disclosure.

An embodiment of the present disclosure may be described with reference to FIGS. 2A and 2B. FIG. 2A depicts an embodiment of a method of analyzing brain functional activity data. The method may include obtaining 2100 a set of data for brain functional activity, e.g., fMRI data, for an individual, e.g., a human individual. The fMRI data may be, in some cases, resting-state fMRI data. The functional activity data may be processed, e.g., computationally processed, to generate 2120 a connectivity model, constrained by a network model 2121 of functional connections among nodes representing a region of interest. An example of a network model of the basal ganglia-thalamo-cortical system is shown in FIG. 6. The connectivity model may be generated using any suitable algorithm, e.g., a dynamic causal modeling (DCM).

The connectivity model is then used to perform a linear regression against connectivity estimates 2141 for different neuronal subtypes, to derive 2140 the regression coefficients. The regression coefficients provide an estimate of the relative activity of different neural pathways, each of which is regulated by a different neuronal subtype.

Figure 2B:
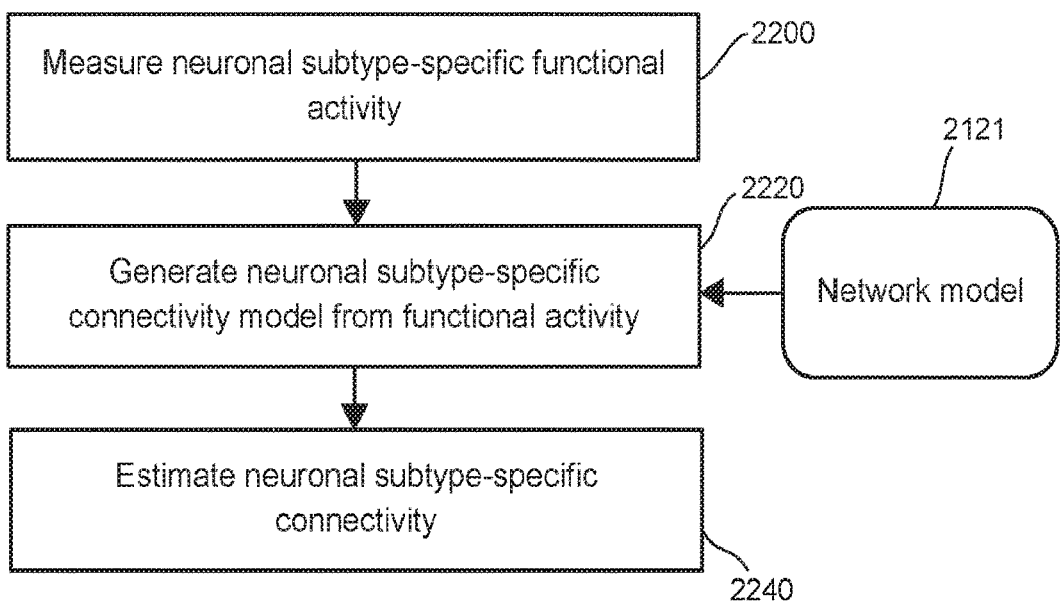

The present disclosure also provides a method of estimating the neuronal subtype-specific connectivity estimates (FIG. 2B). Such a method may include measuring 2200 the functional activity of a neuronal circuit caused by selective activation of neurons in a subtype-specific manner. Selective modulation, e.g., depolarization or hyperpolarization, of neurons in a subtype-specific manner may include, e.g., optogenetic or electrophysiological stimulation, and the functional activity in response to the selective stimulation may be measured, e.g., by fMRI, such as optogenetic fMRI (ofMRI). "Selective" as used herein, may be used to describe an action that is applied to, or a property that is present in, a larger proportion of members within a first group compared to the proportion of members of a second group to which the action is applied, or in which the property is present, where the relative proportions are such that a functional consequence of the action or property can largely be attributed to its effect on members of the first group.

The measured neuronal subtype-specific functional activity data may be processed, e.g., computationally processed, to generate 2220 a subtype-specific connectivity model, constrained by a network model 2121 of functional connections among nodes representing a region of interest. For each neuronal subtype, the connectivity of a neural pathway regulated by activity of the neuronal subtype may be estimated 2240 from the subtype-specific connectivity model.

The data acquisition 2100, 2200, connectivity model-generating 2120, 2220, linear regression analysis 2140, and estimating neuronal subtype-specific connectivity may be performed using a system, as described below, that includes one or more processors and a neural pathway analysis program that, when executed by the processor(s) causes the processor(s) to perform a method of the present disclosure.

The neuronal subtype-specific connectivity estimates may be obtained from any suitable individual. In some cases, the neuronal subtype-specific connectivity estimates are obtained from an individual who is the same as the individual whose brain functional activity data is being analyzed. In some embodiments, the neuronal subtype-specific connectivity estimates are obtained from a second individual who is different from a first individual whose brain functional activity data is being analyzed. The second individual may be an individual of the same or different species as the species to which the first individual belongs. In some cases, the second individual and first individual are both mammals, but belong to different species of mammals. In some cases, the first individual and second individual are each selected from a rodent, feline, canine, monkey, non-human primate, and human.

The functional activity data, including the neuronal subtype functional activity data, may be any suitable form of functional activity data. The functional activity data may include measurements of the collective activity of neurons in a region of the brain where the neuronal activity is not spatially resolved at the level of individual neurons. In other words, the components of the measured functional activity data cannot be readily attributed to any specific neuron subtype (e.g., the components are not attributable to any specific neuron subtype without applying an algorithm to estimate the components). In some cases, the functional activity data are data obtained from functional magnetic resonance imaging (fMRI), magentoencephalography (MEG), electroencephalography (EEG), or a combination thereof.

In some cases, the functional activity data are obtained from an individual who is in a resting state, e.g., wakeful resting state. Thus, in some cases, the individual from whom the functional activity data are obtained may not have been given an explicit task to perform while the individual was monitored to obtain the data.

The connectivity models, including the neuronal subtype-specific connectivity model, may be generated using any suitable method that models the biophysical properties of the brain based on large-scale functional activity data, such as fMRI, MEG or EEG. In some cases, the connectivity models are generated using an algorithm that relies on convolution principles, such as dynamic causal modeling (DCM). In some cases, the DCM may be spectral DCM or time domain DCM. In some cases, the spDCM is stochastic spDCM or deterministic spDCM. A suitable DCM method is described in, e.g., Friston, Karl J., et al. "A DCM for resting state fMRI." *Neuroimage*, 94 (2014): 396-407, the disclosure of which is incorporated herein by reference. In some cases, the connectivity models are generated using an algorithm that is based on mesoscopic properties of the neurons, such as neural mass modeling (NMM).

The process of generating the connectivity models, including the neuronal subtype-specific connectivity model, may be constrained by a network model of functional connections among interconnected nodes in a brain region of interest. In some cases, the network model used to generate the connectivity model for the individual whose brain functional activity data is being analyzed, according to embodiments of the present disclosure, is the same connectivity model used to generate the neuronal subtype-specific connectivity models.

The nodes of the network model may represent one or more anatomical and/or functional brain regions. Suitable anatomical and/or functional brain regions include, without limitation, thalamus, cortex, ventral tegmental area (VTA), prefontal cortex (PFC), nucleus accumbens (NAc), amygdala (BLA), substantia nigra (SN), ventral pallidum, globus pallidus, dorsal striatum, ventral striatum, subthalamic nucleus (STN), anterior caudate putamen (CPu), globus pallidus external (GPe), globus pallidus internal (GPi), hippocampus, dentate gyms, cingulate gyrus, entorhinal cortex, olfactory cortex, motor cortex, cerebellum. A node may also represent, in some cases, any subregion of anatomical and/or functional brain regions, such as those listed above, where a subregion includes at least a portion of an anatomical and/or functional brain region as described above. A node may also represent, in some cases, any superregion of anatomical and/or functional brain regions, where a superregion includes two or more anatomical and/or functional brain regions (or portions thereof), such as those listed above.

Figure 1:
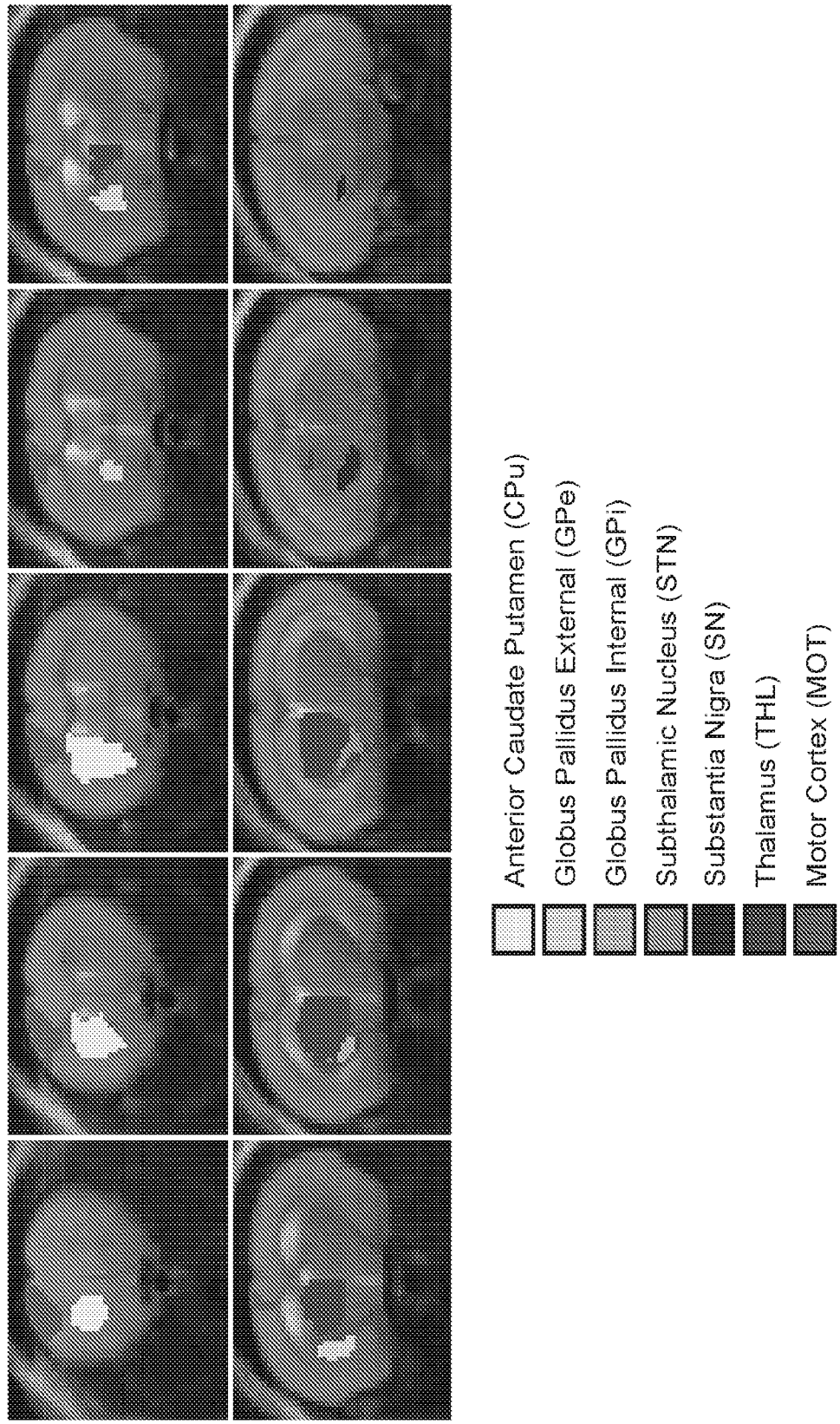
FIG. 1 is a collection of functional magnetic resonance imaging (fMRI) images showing evolutionary conservation of nuclei and regions in the basal ganglia-thalamocortical complex involved in voluntary movement.
Figure 1:
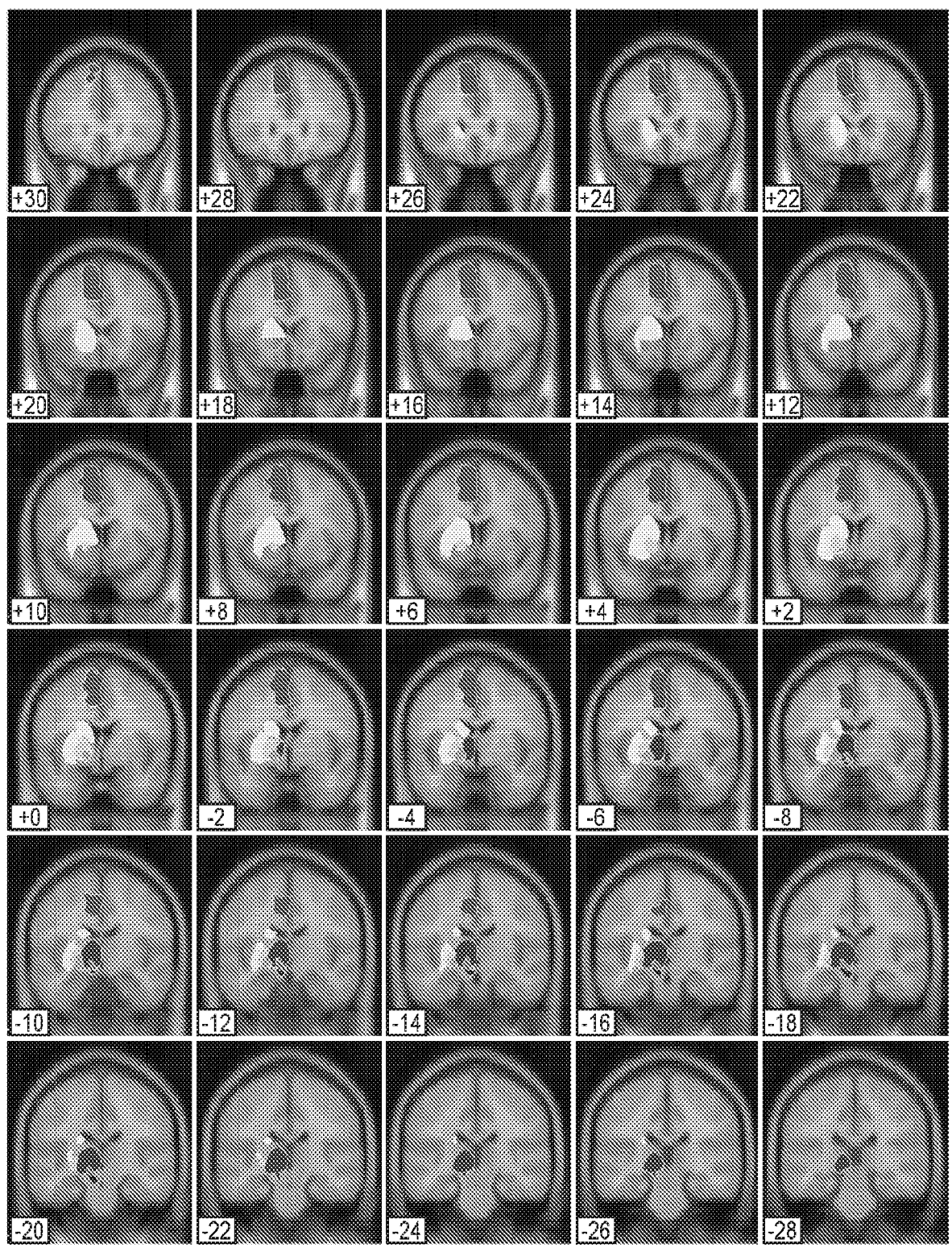

In some embodiments, the region of the brain and/or the network model represent neural systems that are conserved across different species of mammals. A conserved neural system may exhibit a functional activity of similar anatomically and/or functionally defined brain structures in a similar temporal order between two different species of individuals. In some cases, the conserved neural system is the basal ganglia-thalamocortical circuit, as shown in FIG. 1.

The network model may include any suitable number of nodes. In some cases, the network model includes 2 or more, 3 or more, e.g., 4 or more, 5 or more, 6 or more, 7 or more, 8 or more, 9 or more, 10 or more, 15 or more, 20 or more, 50 or more, 100 or more, including 1,000 or more interconnected nodes, and in some embodiments, includes 100,000 or fewer, e.g., 10,000 or fewer, 5,000 or fewer, 1,000 or fewer, 500 or fewer, 200 or fewer, 100 or fewer, 80 or fewer, 60 or fewer, 40 or fewer, 20 or fewer, 15 or fewer, including 10 or fewer nodes. In some embodiments, the network model includes a number of nodes in the range of 2 to 100,000, such as 3 to 100,000, e.g., 4 to 10,000, 4 to 5,000, 4 to 1,000, 4 to 500, 4 to 200, 4 to 100, 4 to 80, 5 to 60, 5 to 40, 5 to 20, including 6 to 15.

The network model may be derived from any suitable source. In some cases, the network model is based on a survey of published literature on the anatomical and/or functional connections among brain regions that correspond to nodes of the network. In some cases, the network model is based on empirical data, e.g., diffusion tensor fMRI data, immunohistochemistry data, tracer data, etc. In some cases, the network model is based on diffusion tensor fMRI data. In some cases, the network model is based on immunohistochemistry data. In some cases, the network model is based on tracer data.

The regression coefficients may be derived from the connectivity model using any suitable regression method. In some cases, the regression is general linear model, linear least squares regression, robust linear regression, support vector machine, quadratic programming, or ridge regression. In some cases, the regression is a general linear model. In some cases, the regression is a linear least squares regression. In some cases, the regression is a robust linear regression. In some cases, the regression is a support vector machine. In some cases, the regression is a quadratic programming. In some cases, the regression is a ridge regression.

The neuronal subtype may be defined using any suitable property of neurons in a brain. Properties by which a neuronal subtype is defined may include, without limitation, physical form, location, marker expression, activity pattern (e.g., frequency, duration or magnitude of activity, etc.), and combinations thereof.

A neuronal subtype may include neurons from any suitable brain region. Suitable brain regions include, without limitation, thalamus, cortex, ventral tegmental area (VTA), prefontal cortex (PFC), nucleus accumbens (NAc), amygdala (BLA), substantia nigra (SN), ventral pallidum, globus pallidus, dorsal striatum, ventral striatum, subthalamic nucleus (STN), anterior caudate putamen (CPu), globus pallidus external (GPe), globus pallidus internal (GPi), hippocampus, dentate gyrus, cingulate gyms, entorhinal cortex, olfactory cortex, motor cortex, cerebellum.

A neuronal subtype may be classified based on any suitable physical form of the neuron. Suitable neuron types include, without limitation, medium spiny neurons (MSN), pyramidal cell, small gelatinosa cell, spindle-shaped cell, granule cell, ovoid cell, globus pallidus cell, small reticular formation, large reticular formation, and Purkinje cells.

A neuronal subtype may be defined by one or more neurotransmitters produced by neurons of the subtype. In some cases, neurons of a neuronal subtype are, without limitation, dopaminergic, cholinergic, gamma-aminobutyric acid-(GABA)ergic, glutamatergic, or peptidergic neurons, and the like.

A neuronal subtype may be defined by any suitable receptor expression. Suitable receptors expressed by neurons of a subtype include, without limitation, dopamine receptor subtypes ($D_1$, $D_2$, $D_3$, $D_4$, and/or $D_5$); metabotropic glutamate receptor subtypes ($mGluR_1$, $mGluR_2$, $mGluR_3$, $mGluR_4$, $mGluR_5$, $mGluR_6$, $mGluR_7$, and/or $mGluR_8$); ionotropic glutamate receptor subtypes ($\alpha$-amino-3-hydroxy-5-methyl-4-isoxazolepropionic acid (AMPA), Kainate, and/or N-methyl-D-aspartate (NMDA)); metabotropic acetylcholine receptor subtypes ($M_1$, $M_2$, $M_3$, $M_4$, and/or $M_5$); ionotropic acetylcholine receptor subtypes; $GABA_A$ receptor subtypes ($\alpha$, $\beta$, $\gamma$, $\delta$, $\epsilon$, $\pi$, $\theta$, and/or $\rho$); and/or $GABA_B$ receptor subtypes ($GABA_{B1}$, and/or $GABA_{B2}$).

A neuronal subtype may be defined by expression of any other suitable marker by neurons of the subtype.

The plurality of neuronal subtypes may include any suitable number of subtypes. In some cases, the number of neuronal subtypes is 2 or more, e.g., 3 or more, 4 or more, 5 or more, 6 or more, 7 or more, 8 or more, 9 or more, 10 or more, 15 or more, 20 or more, 50 or more, including 100 or more interconnected nodes, and in some embodiments, is 10,000 or fewer, e.g., 5,000 or fewer, 1,000 or fewer, 500 or fewer, 200 or fewer, 100 or fewer, 80 or fewer, 60 or fewer, 40 or fewer, 20 or fewer, 15 or fewer, including 10 or fewer nodes. In some embodiments, the neuronal subtypes include a number of subtypes in the range of 2 to 10,000, e.g., 2 to 5,000, 2 to 1,000, 2 to 500, 2 to 200, 2 to 100, 2 to 80, 2 to 60, 2 to 40, 2 to 20, including 2 to 10.

In some embodiments, the neuronal subtype-specific connectivity estimates between two neuronal subtypes are substantially orthogonal to each other. In some cases, the neuronal subtype-specific connectivity estimates between two neuronal subtypes may have a correlation coefficient, e.g., Pearson's correlation coefficient, of 0.5 or less, e.g., 0.4 or less, 0.3 or less, 0.2 or less, 0.1 or less, 0.05 or less, 0.03 or less, including 0.01 or less, and may have a correlation coefficient of −0.5 or more, e.g., −0.4 or more, −0.3 or more, −0.2 or more, −0.1 or more, −0.05 or more, −0.03 or more, including 0.01 or more. In some embodiments, the neuronal subtype-specific connectivity estimates between two neuronal subtypes may have a correlation coefficient, e.g., Pearson's correlation coefficient, in the range of −0.5 to 0.5, e.g., −0.4 to 0.4, −0.3 to 0.3, −0.2 to 0.2, −0.1 to 0.1, −0.05 to 0.05, including −0.03 to 0.03.

The individual may be any suitable individual for analyzing the individual's brain functional activity data. In some cases, the individual is a human individual. In some cases the human is a healthy human, or a human having a neurological disorder. The neurological disorder may be any neurological disorder. In some cases, the neurological disorder is caused by a disease, e.g., a neurological disease. The neurological disease may be any disease associated with pathological activity of a network of neurons. Suitable neurological diseases include, without limitation, Parkinson's disease, Alzheimer's disease, dementia, epilepsy, autism, bipolar disorder, schizophrenia, Tourette's syndrome, obsessive compulsive disorder, attention deficit hyperactivity disorder, Huntington's disease, multiple sclerosis, or migraine. In some embodiments, the neurological disorder is an age-related disorder of brain function.

Selective activation of neurons in order to measure subtype-specific functional activity may be done using any suitable method. Suitable methods of selective neuron activation include, without limitation, optogenetic stimulation, single unit electrophysiology, etc. Examples of some methods and systems suitable for optogenetic stimulation are described in additional detail in U.S. Pat. Nos. 8,696,722; 8,834,546; and 9,271,674; U.S. Application Publication No. 2016/0270723; and PCT Application Nos. PCT/US2016/043179; PCT/US2016/064250; and PCT/US2016/049508, the disclosures of each of which are incorporated herein by reference.

Where the neurons are selectively activated by optogenetic stimulation, the neurons may express one or more light-activated polypeptides configured to hyperpolarize or depolarize the neurons. Suitable light-activated polypeptides and methods used thereof are described further below.

Light-Activated Polypeptides

A light-activated polypeptide of the present disclosure may be any suitable light-activated polypeptide for selectively activating neurons of a subtype by illuminating the neurons with an activating light stimulus. In some instances, the light-activated polypeptide is a light-activated ion channel polypeptide. The light-activated ion channel polypeptides are adapted to allow one or more ions to pass through the plasma membrane of a target cell when the polypeptide is illuminated with light of an activating wavelength. Light-activated proteins may be characterized as ion pump proteins, which facilitate the passage of a small number of ions through the plasma membrane per photon of light, or as ion channel proteins, which allow a stream of ions to freely flow through the plasma membrane when the channel is open. In some embodiments, the light-activated polypeptide depolarizes the cell when activated by light of an activating wavelength. In some embodiments, the light-activated polypeptide hyperpolarizes the cell when activated by light of an activating wavelength. Suitable hyperpolarizing and depolarizing polypeptides are known in the art and include, e.g., a channelrhodopsin (e.g., ChR2), variants of ChR2 (e.g., C128S, D156A, C128S+D156A, E123A, E123T), iC1C2, C1C2, GtACR2, NpHR, eNpHR3.0, C1V1, VChR1, VChR2, SwiChR, Arch, ArchT, KR2, ReaChR, ChIEF, Chronos, ChRGR, CsChrimson, and the like. In some cases, the light-activated polypeptide includes bReaCh-ES, as described herein and described further in, e.g., Rajasethupathy et al., Nature, 2015 Oct. 29, 526(7575):653, which is incorporated herein by reference. Hyperpolarizing and depolarizing opsins have been described in various publications; see, e.g., Berndt and Deisseroth (2015) Science 349:590; Berndt et al. (2014) Science 344:420; and Guru et al. (Jul. 25, 2015) Intl. J. Neuropsychopharmacol. pp. 1-8 (PMID 26209858).

The light-activated polypeptide may be introduced into the neurons using any suitable method. In some cases, the neurons of a subtype of interest are genetically modified to express a light-activated polypeptide. In some cases, the neurons may be genetically modified using a viral vector, e.g., an adeno-associated viral vector, containing a nucleic acid having a nucleotide sequence that encodes the light-activated polypeptide. The viral vector may include any suitable control elements (e.g., promoters, enhancers, recombination sites, etc.) to control expression of the light-activated polypeptide according to neuronal subtype, timing, presence of an inducer, etc.

Neuron-specific promoters and other control elements (e.g., enhancers) are known in the art. Suitable neuron-specific control sequences include, but are not limited to, a neuron-specific enolase (NSE) promoter (see, e.g., EMBL HSENO2, X51956; see also, e.g., U.S. Pat. Nos. 6,649,811, 5,387,742); an aromatic amino acid decarboxylase (AADC) promoter; a neurofilament promoter (see, e.g., GenBank HUMNFL, L04147); a synapsin promoter (see, e.g., GenBank HUMSYNIB, M55301); a thy-1 promoter (see, e.g., Chen et al. (1987) Cell 51:7-19; and Llewellyn et al. (2010) Nat. Med. 16:1161); a serotonin receptor promoter (see, e.g., GenBank S62283); a tyrosine hydroxylase promoter (TH) (see, e.g., Nucl. Acids. Res. 15:2363-2384 (1987) and Neuron 6:583-594 (1991)); a GnRH promoter (see, e.g., Radovick et al., Proc. Natl. Acad. Sci. USA 88:3402-3406 (1991)); an L7 promoter (see, e.g., Oberdick et al., Science 248:223-226 (1990)); a DNMT promoter (see, e.g., Bartge et al., Proc. Natl. Acad. Sci. USA 85:3648-3652 (1988)); an enkephalin promoter (see, e.g., Comb et al., EMBO J. 17:3793-3805 (1988)); a myelin basic protein (MBP) promoter; a CMV enhancer/platelet-derived growth factor-β promoter (see, e.g., Liu et al. (2620) Gene Therapy 11:52-60); a motor neuron-specific gene Hb9 promoter (see, e.g., U.S. Pat. No. 7,632,679; and Lee et al. (2620) Development 131:3295-3306); and an alpha subunit of Ca($^{2+}$)-calmodulin-dependent protein kinase II (CaMKIIα) promoter (see, e.g., Mayford et al. (1996) Proc. Natl. Acad. Sci. USA 93:13250). Other suitable promoters include elongation factor (EF) 1α and dopamine transporter (DAT) promoters.

In some cases, neuronal subtype-specific expression of the light-activated polypeptide may be achieved by using recombination systems, e.g., Cre-Lox recombination, Flp-FRT recombination, etc. Cell type-specific expression of genes using recombination has been described in, e.g., Fenno et al., Nat Methods. 2014 July; 11(7):763; and Gompf et al., Front Behav Neurosci. 2015 Jul. 2; 9:152, which are incorporated by reference herein.

Systems

Figure 2C:
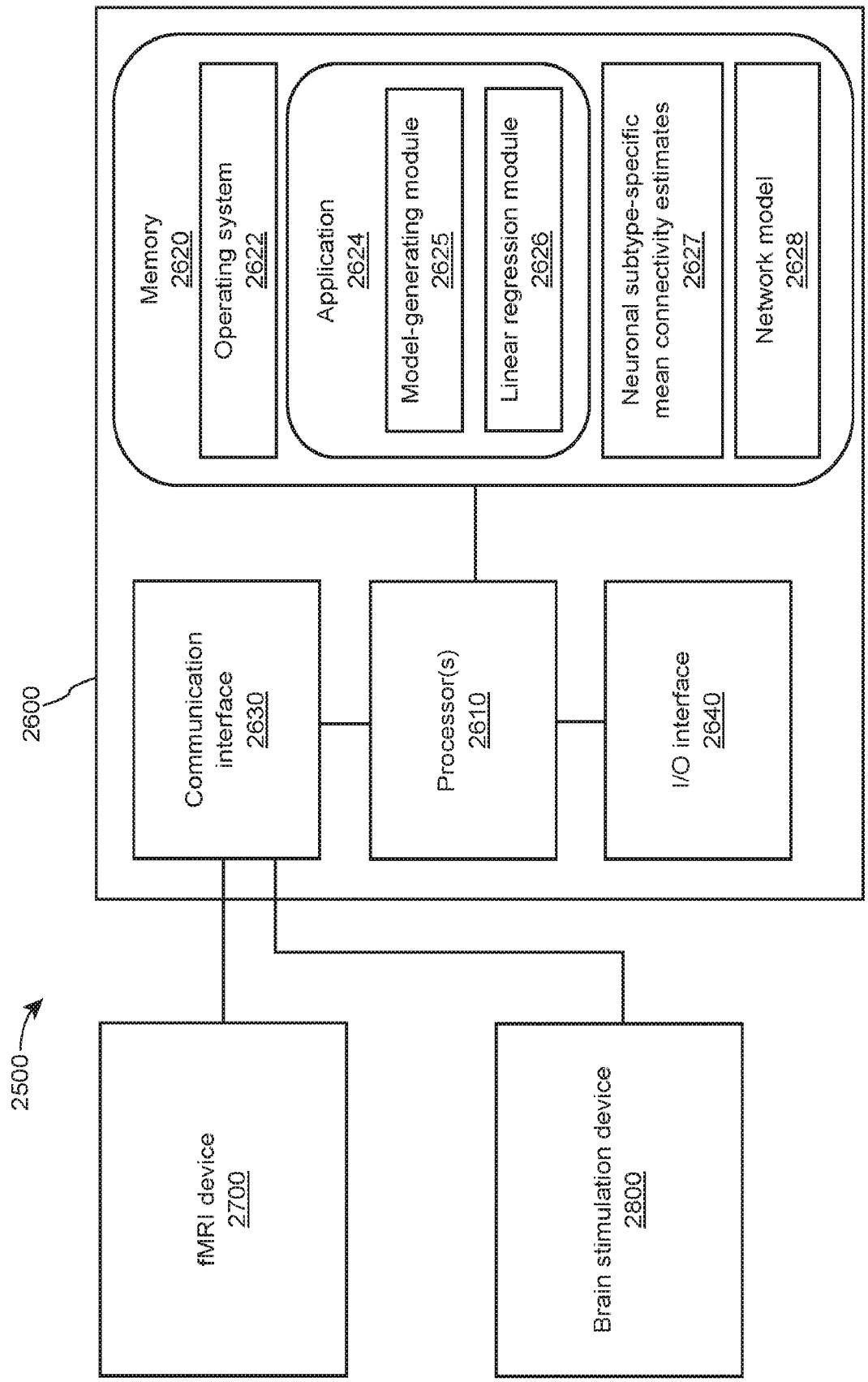

Also provided herein is a system for performing a method of the present disclosure, as described above. With reference to FIG. 2C, the present system 2500 may include an fMRI device 2700, a processor 2610, and a memory 2620 (e.g., a non-transient memory on a computer-readable medium). The memory 2620 may contain an application 2624 or program that, when executed by the processor 2610, causes the fMRI device 2700 to record functional activity of an individual's brain to generate functional activity data for the individual, and further perform a method of analyzing functional activity data, as described herein.

The fMRI device 2700 may be any suitable device. Suitable devices are described in, e.g., U.S. Pat. No. 8,834,546; U.S. Application Publication No. 2016/0270723; and PCT Application Nos. PCT/US2016/043179; PCT/US2016/064250; and PCT/US2016/049508, the disclosures of which are incorporated herein by reference.

The system 2500 includes one or more processing units (also called herein "processors") 2610, memory 2620 (i.e., a computer readable storage medium), an input/output (I/O) interface 2640, and a communications interface 2630. These components communicate with one another over one or more communication buses or signal lines. In some embodiments, the memory 2620, or the computer readable storage media or memory, stores an operating system 2622, programs 2624, modules, instructions, and stored data. The one or more processors are coupled to the memory and operable to execute these programs, modules, and instructions, and read/write from/to the stored data.

In some embodiments, the processing units 2610 include one or more microprocessors, such as a single core or multi-core microprocessor. In some embodiments, the processing units include one or more general purpose processors. In some embodiments, the processing units include one or more special purpose processors (e.g., programmed to execute the methods described herein).

In some embodiments, the memory 2620 includes high-speed random access memory, such as DRAM, SRAM, DDR RAM or other random access solid state memory devices. In some embodiments the memory includes non-volatile memory, such as one or more magnetic disk storage devices, optical disk storage devices, flash memory devices, or other non-volatile solid state storage devices. In some embodiments, the memory includes one or more storage devices remotely located from the processing units 2610. The memory, or alternately the non-volatile memory device(s) within the memory, includes a computer readable storage medium. In some embodiments, the memory includes a non-transitory computer readable storage medium.

In some embodiments, the I/O interface 2640 is coupled to one or more input/output devices, such as one or more displays, keyboards, touch-sensitive surfaces (such as a track pad or a touch-sensitive surface of a touch-sensitive display), speakers, and microphones. The I/O interface may be configured to receive user inputs (e.g., voice input, keyboard inputs, touch inputs, etc.) from a user and process them accordingly. The I/O interface may also be configured to present outputs (e.g., sounds, images, text, etc.) to the user according to various program instructions implemented on the system 2500.

In some embodiments, the communications interface 2630 includes wired communication port(s) and/or wireless transmission and reception circuitry. The wired communication port(s) receive and send communication signals via one or more wired interfaces, e.g., Ethernet, Universal Serial Bus (USB), FIREWIRE, etc. The wireless circuitry receives and sends RF signals, infrared signals, and/or optical signals from/to communications networks and other communications devices. The wireless communications may use any of a plurality of communications standards, protocols and technologies, such as GSM, EDGE, CDMA, TDMA, Bluetooth, Wi-Fi, VoIP, Wi-MAX, or any other suitable wireless communication protocol. The network communications interface enables communication between the system 2500 with networks, such as the Internet, an intranet and/or a wireless network, such as a cellular telephone network, a local area network (LAN) a wireless local area network (WLAN) and/or a metropolitan area network (MAN), and other devices. Network communications interface is configured to facilitate communications between the system and other devices over a network.

In some aspects, the system may include a computer 2600, which may be a personal device (e.g., laptop, desktop, workplace computer, portable device, etc.). A computer that is a personal device may not need to be connected to a network. In other instances, a computer that is a personal device is connected to a network (e.g., a wired or wireless connection as described above).

In some aspects, the computer 2600 is a server or a collection of servers, and may not need an I/O interface. For example, the computer 2600 may be a server, and a neural pathway analysis program of the present disclosure 2124 may be accessed by a user through a website.

In some embodiments, the operating system 2622 (e.g., LINUX®, UNIX®, OS X®, WINDOWS®, or an embedded operating system) includes various software components and/or drivers for controlling and managing general system tasks (e.g., memory management, storage device control, power management, etc.) and facilitates communications between various hardware, firmware, and software components.

It should be noted that the system 2500 is only one example, and that the system 2500 may have more or fewer components than shown, may combine two or more components, or may have a different configuration or arrangement of the components. The various components shown in FIG. 2C may be implemented in hardware, software, firmware, including one or more signal processing and/or application specific integrated circuits, or a combination of thereof.

In FIG. 2C, the neural pathway analysis program 2624 includes one or more programs stored in the memory 2620, and may include instructions to perform methods according to one or more embodiments of the methods described herein. The neural pathway analysis program 2624 may include any of the following examples of modules or a subset or a superset thereof.

In some cases, a neural pathway analysis program 2624 may be configured to computationally process functional activity data for a region of a brain of an individual, as described above, to generate an estimate of the relative activities of neural pathways regulated by each of a plurality of neuronal subtypes, by generating a connectivity model from the functional activity data based on a network model 2627 of functional connections among interconnected nodes representing the region, as described herein; and deriving a set of coefficients from a linear regression between a) the connectivity model; and b) neuronal subtype-specific connectivity estimates 2628 among the interconnected nodes, as described herein.

The present system 2500 may include an fMRI device 2700, configured to measure functional brain activity of an individual. The computer system 2600 may be in communication with the fMRI device, through the communication interface 2630, such that the computer system can control operation of the fMRI device and/or retrieve functional imaging data from the fMRI device.

The neural pathway analysis program 2624 may include a model-generating module, e.g., a spDCM module, 2625 configured to generate the connectivity model from the functional activity data based on a network model 2627 of functional connections among interconnected nodes representing the region.

The neural pathway analysis program 2624 may include a linear regression module 2626 configured to perform a linear regression between a) the connectivity model; and b) neuronal subtype-specific connectivity estimates 2628, to derive a set of coefficients that represent the contribution to the functional activity data of a neural pathway regulated by different neuronal subtypes.

The methods described herein may be performed by the computer system 2600. In some embodiments, the computer system 2600 is a distributed computer system. For example, the computer system 2600 may include a first set of one or more processors located remotely from a second set of one or more processors. In some embodiments, the computer system 2600 includes a web server configured to provide a web interface. In some embodiments, the web interface is configured to receive data. In some embodiments, the web interface is configured to display results.

In certain aspects, the neural pathway analysis program, 2624 may be configurable by a user. For example, a the neural pathway analysis program may include a user interface module (not shown) configured to enable a user to determine one or more settings, such as the network model 2628, neuronal subtype-specific connectivity estimates 2627, whether to include neural fluctuations, etc., to apply to the model generating and/or linear regression algorithms, or any other settings that would allow performance of one or more embodiments of the methods described herein.

In some embodiments, the system 2500 includes a brain stimulation device 2800, such as a deep brain stimulation device or a transcranial magnetic stimulation device, configured to stimulate a brain region of the individual being monitored by the fMRI device 2700. In some embodiments, the computer system 2600 may be configured to control the brain stimulation device based on the analysis of neural pathways contributing to the functional brain activity data, according to methods of the present disclosure. For example, if the neural pathway analysis indicates that an individual has insufficient activity in a neural pathway associated with a neurological disorder from which the individual suffers, the computer system may provide an appropriate stimulation to the relevant brain region that regulates the neural pathway via the brain stimulation device, thereby rebalancing the level of the neural pathway activity in the individual's brain.

Utility

The methods and systems of the present disclosure find use in a variety of applications, where an understanding of the neural pathway mechanisms underlying a non-invasively acquired functional brain activity data in an individual is desired. The present methods and systems may find use in obtaining a mechanistic understanding of the neural pathways underlying a neurological disorder, e.g., Parkinson's disease; providing a diagnostic/prognostic/predictive tool for neurological disorders; contributing to development of new treatments, e.g., cell-specific and/or frequency-dependent therapeutic trials (e.g., for drug development and/or deep brain stimulation); aiding in monitoring the progression of core symptoms of a neurological disorder, e.g., dyskinesia and/or bradykinesia in PD; monitoring the efficacy of a treatment for a neurological disorder, etc.

Thus, aspects of the present disclosure include a method of identifying a neural circuit-level biomarker associated with a neurological disorder, using the methods and systems as described above. "Associate" as used herein, may refer to any specific relationship between a neural pathway and a neurological disorder, including a relationship with a treatment for the disorder. The relationship may be causal or correlative.

Thus a method of estimating relative activities of neural pathways regulated by different neuronal subtypes based on an analyses of brain functional activity data, as described herein, may be used to identify a neural circuit-level biomarker associated with a neurological disorder, by comparing the results of the analyses from two groups of individuals that are different from each other with respect to one or more aspects related to a neurological disorder. The analyses may provide a set of regression coefficients that relate neuronal subtype-specific connectivity estimates to a connectivity model for brain functional activity data for each group of individuals. A difference measurement between the different sets of regression coefficients may then be calculated to determine whether the distribution of regression coefficients in one group is different from the distribution in another group. Where the two groups are a case group of individuals having a neurological disorder, and a control group of individuals not having the neurological disorder, the difference measurement may indicate that the case set of regression coefficients is a neural circuit-level biomarker associated with the neurological disorder. Where the two groups are a case group of individuals who have a neurological disorder and have received a treatment for the neurological disorder, and a control group of individuals who have the neurological disorder and have not received a treatment for the neurological disorder, the difference measurement may indicate that the case set of regression coefficients is a neural circuit-level biomarker associated with the treatment for the neurological disorder.

The difference measurement may be any suitable measure of the relationship between different sets of regression coefficients. Suitable difference measurements include, without limitation, subtraction, division, correlation, deviation. In some cases the difference measurement is the Pearson product-moment correlation coefficient, Spearman rank correlation, root mean squared error (RMSE), Euclidean distance, or mean absolute deviation (MAD).

The difference measurement may be compared relative to a threshold criterion. If the difference measurement meets the threshold criterion, it may be concluded that an association between the neural circuit-level biomarker and the neurological disorder exists. In some cases, the threshold criterion includes a threshold value, where a difference measurement above (or below) the threshold value supports the association between the neural circuit-level biomarker and the neurological disorder. In some cases, the difference measurement is a statistical significance values, e.g., a p-value, where a difference measurement below the p-value supports the association between the neural circuit-level biomarker and the neurological disorder.

In another aspect, a method of estimating relative activities of neural pathways regulated by different neuronal subtypes based on an analyses of brain functional activity data, as described herein, may be used to evaluate the predictive value of a neural circuit-level biomarker to progression, prognosis, and/or response to treatment of a neurological disorder in an individual.

In some embodiments, a method of estimating relative activities of neural pathways regulated by different neuronal subtypes based on analyses of brain functional activity data, as described herein, may be used to determine or adjust a parameter for a therapy for a neurological disorder. In some cases, a stimulus protocol for brain stimulation therapy (e.g., deep brain stimulation, transcranial magnetic stimulation, etc., with stimulation parameters, such as the frequency of stimulation, the target of stimulation, the duration of stimulation, etc.) may be adjusted based on the analyses of brain functional activity, The neurological disorder may be any suitable neurological disorder. In some cases, the neurological disorder is a neurological disease, or an age-related neurological disorder. In some embodiments, the neurological disease is Parkinson's disease, Alzheimer's disease, dementia, epilepsy, autism, bipolar disorder, schizophrenia, Tourette's syndrome, obsessive compulsive disorder, attention deficit hyperactivity disorder, Huntington's disease, multiple sclerosis, or migraine.

Additional Embodiments

Further embodiments of the present disclosure are described below.

Figure 8:
FIG. 8 is a schematic diagram showing an organization of different aspects of the present method, according to embodiments of the present disclosure.

An embodiment of the present disclosure includes three modules: a) animal data; b) computational modeling, and c) human data. FIG. 8 illustrates the three modules and workflow of the embodiment of the present disclosure:

The first module includes experimental design, instrumentation, acquisition, and processing of animal brain data. This module provides the technology to map brain function using invasive and/or non-invasive recordings while manipulating specific neuron types with optogenetics and/or other neuromodulation tools. The second module refers to the computational modeling of animal data. The second module estimates brain networks implicated in neurological and/or psychiatric disorders driven by optogenetic (de) activations of specific neuron types. Finally, the third module constitutes the acquisition, processing, and network analyses of human brain data. The third module examines and quantifies the contribution of specific cell types and stimulation frequencies to disease-specific human brain networks during resting-state conditions.

M1: Animal Data

The first module may include the procedures employed to collect cell type and frequency specific neuroimaging data in animals. Optogenetics in conjunction with invasive/non-invasive neural recordings will be used to allow modulation of specific cells using light pulses at different frequencies while mapping brain function. Optogenetic fMRI (ofMRI) provides a tool to explore in vivo the neuronal connectivity among brain regions.

Within this module, optogenetic experiments are performed, where the experiments target specific neuron-types (e.g., excitatory pyramidal neurons and/or inhibitory interneurons), which in turn drive specific brain circuits (e.g., basal ganglia pathways). These brain circuits driven by specific cell types may contribute to the total variance observed in human brain data and potentially we may be able to quantify such specific contributions to human brain networks (see third module for further details).

For example, the functional significance of two neuron types on basal ganglia circuitry may be investigated. The basal ganglia are a phylogenetically old and evolutionarily conserved group of nuclei crucial for goal-oriented motor action. In some cases, evolutionary conserved brain regions may be taken into account when translating circuit models into humans and when developing and/or testing therapeutic interventions. FIG. 2 shows anatomical masks for the basal ganglia-thalamocortical complex in mice and humans.

The basal ganglia include several interconnected subcortical nuclei controlling voluntary movement. The two output nuclei of the basal ganglia, the internal pallidal aspect and the substantia nigra (pars reticulata), tonically inhibit the thalamus, which in turn, send projections to the cortex to initiate or terminate movement. This inhibitory output is thought to be modulated by the direct and indirect pathways that run from the striatum. Within the striatum, medium spiny neurons (MSN) that project directly to the two output nuclei have D1 dopamine receptors that facilitate transmission, while those that project in the indirect pathway have D2 dopamine receptors that reduce transmission. These pathways may provide a system to dissociate the contribution of different neurons, since they are relatively well-characterized, topographically segregated, and functionally opposing.

With these optogenetic experiments, the influence of each neuron type within the dorsomedial caudate-putamen aspect on the workings of the basal ganglia-thalamocortical complex may be established. The two optogenetic manipulations may provide an explanation for the cell-type and frequency-dependent response of brain activity in resting-state data. Table 1 illustrates an example experimental design:

TABLE 1

| Initial experimental design | | | |
|---|---|---|---|
| | | Cell type | |
| | | D1-MSN | D2-MSN |
| Stimulation frequency | 20 Hz | D1 @ 20 Hz | D2 @ 20 Hz |

In some embodiments, more ofMRI data may be collected and the initial design may be updated with a second factor. Table 2 depicts a 2×2 factorial design that will enable to assess the separate effects of D1- and D2-MSN cell types at high and low stimulation frequencies on the workings of the basal ganglia circuitry, for example:

TABLE 2

| A proposed 2 × 2 factorial design | | | |
|---|---|---|---|
| | | Cell type | |
| | | D1-MSN | D2-MSN |
| Stimulation frequency | Low (20 Hz) | D1 @ Low | D2 @ Low |
| | High (130 Hz) | D1 @ High | D2 @ High |

In some embodiments, three different areas (subfields) within the striatal aspect may be illuminated. Subfields of interest include, e.g., the ventral striatum, dorsal caudate nucleus, and dorsal-anterior putamen. Thus, the definition and implementation of a third factor may include the location of the illumination source. With this factor, a new set of regressors (independent variables) that will reveal the spatial effects of optical stimulation on remote brain areas may be generated.

M2: Computational Modeling

The computational modeling toolbox may model and characterize brain systems from data collected in the previous module, i.e. using optogenetics and multimodal recording techniques. The computational modeling toolbox includes imaging/recording techniques—optogenetic fMRI, LFP, MUA, SUA, and optical imaging responses—and biophysical modeling initiatives—dynamic causal modeling (DCM) which is based on convolution principles and/or neural mass modeling (NMM) based on mesoscopic properties. The combination of optogenetics and imaging methods together with computational modelling may provide for the understanding of the biological underpinnings of brain networks.

As introduced above, ofMRI may be used to investigate the contribution of two cell-types on basal ganglia pathways. Within this modelling unit, spectral DCM (spDCM) may be used to estimate the effective connectivity among brain regions. A 7-node brain network consisting of: caudate-putamen aspect (CPu), globus pallidus external segment (GPe), globus pallidus internal segment (GPi), subthalamic nucleus (STN), substantia nigra (SN), thalamus (THL), and motor cortex (MOT) aspects ipsilateral to the stimulation site may be modeled.

In general, connectivity algorithms may rely on identifying the most appropriate generative model for the data among neurobiologically plausible candidates. To constrain the models, anatomical connectivity information obtained through diffusion tensor MRI immunohistochemistry data, and/or literature search are commonly used. In this particular case, we searched the literature to select the most likely generative model. FIG. 6 depicts an example of a connection scheme that may be used in this example.

In some embodiments, other experiments (factors) described above, i.e. D1- and D2-MSN stimulations at high frequency, may be performed and proceed with the estimation of brain networks in the same way. This analysis will generate a new set of network-estimates at high frequency as was done for low frequency stimulation in FIGS. 7A-7C.

M3: Human Data

In some embodiments, the third module includes the experiments, data collection, and analyses performed in humans. As above-mentioned, an aspect of the present disclosure includes translating models build using data collected in animals: ($m_1$, $m_2$, . . . ), into human fMRI data. Through this approach a cell type specific description of brain network function in the healthy and the diseased human brain may be provided. The same brain networks as previously examined in animal models may be examined and the contribution of each cell type and frequency dependent network in human brains may be estimated by means of regression analyses such as the general lineal model (GLM) or advanced statistical methods such as support vector machines (SVM).

These analyses may generate regression coefficients for each individual: ($\alpha_i$, $\beta_i$, . . . ), that may reveal the effects of specific cell types (and frequency) on the resting-state brain network of interest, e.g. the basal ganglia-thalamocortical circuitry. These regression coefficients, henceforth neurophysiological scores, may constitute a vector subspace that potentially may characterize behavior, traits, or symptoms observed in those individuals. Then the distribution of these scores may be estimated and examined across individuals: ($\underline{\alpha}$, $\underline{\beta}$, . . . ), and statistical differences on those scores may be investigated at the group-level between the healthy and the diseased brain. In this context, group-analyses are appropriate for analyses.

For instance, considering the previous example, the contribution of D1- and D2-MSN cell types to the basal ganglia-thalamocortical network of the normal and parkinsonian human brain may be quantified by means of rsfMRI. In some cases, for the two optogenetic manipulations, there may be two different, approximately orthogonal patterns of effective connectivity among brain regions (see FIGS. 7A-7C). In other words, between D1- and D2-connectivity estimates, Pearson's r=0.02.

The same resting-state network in a given i-th human subject may be estimated and the contribution of D1- and D2-MSN cell types calculated. In other words, a multiple linear regression problem may be solved according to Equation (I):

$$\text{spDCM}_i = \alpha_i \times [\text{spDCM}_{D1\text{-}MSN}] + \beta_i \times [\text{spDCM}_{D2\text{-}MSN}] + \zeta_i \times [\text{constant}]$$

Equation (I). Multiple Linear Regression Considering the Initial Experimental Design where $\text{spDCM}_i$ is the vector of network-estimates (i.e., connectivity parameters) for the i-th human subject, $\text{spDCM}_{D1\text{-}MSN}$ and $\text{spDCM}_{D2\text{-}MSN}$ are vectors of averaged network-estimates for D1- and D2-MSN stimulations (e.g. thresholded estimates), $\alpha_i$ and $\beta_i$ denote the contribution of direct and indirect pathways to the resting-state network for the i-th human subject, and i runs from 1 to $N_s$, being $N_s$ the total number of participants.

When identifying differences between groups, this approach may generate two (multivariate) distributions: p ($\underline{\alpha}_c$, $\underline{\beta}_c$) and p ($\underline{\alpha}_p$, $\underline{\beta}_p$), where the pairs: {$\alpha_c$, $\beta_c$} and {$\alpha_p$, $\beta_p$}, will denote the contribution of direct and indirect pathway networks for the control and parkinsonian groups respectively. By comparing the two groups, statistical differences in the distribution of the neurophysiological scores: p ($\underline{\alpha}_c$, $\underline{\beta}_c$) vs. p ($\underline{\alpha}_p$, $\underline{\beta}_p$) may be observed, which may indicate the aberrant neurobiology of the PD cohort in relation to the D1- and D2-MSN cell types.

As noted earlier, a more complex experimental designs, e.g., a 2×2 factorial design, may be used in some embodiments. Likewise the same multiple linear regression procedure may be used by using more optogenetic experiments (factors). For example, when considering the above-described 2×2 factorial design, the regression model can be implemented as follows according to Equation (II):

$$\text{spDCM}_i = \alpha_i \times [\text{spDCM}_{D1\text{-}MSN, \, low\text{-}frequency}] + \beta_i \times [\text{spDCM}_{D2\text{-}MSN, \, low\text{-}frequency}] + \gamma_i \times [\text{spDCM}_{D1\text{-}MSN, high\text{-}frequency}] + \delta_i \times [\text{spDCM}_{D2\text{-}MSN, high\text{-}frequency}] + \zeta_i \times [\text{constant}]$$

Equation (II). Multiple Linear Regression Considering the 2×2 Factorial Design where $\text{spDCM}_i$ is the vector of network-estimates (i.e. connectivity parameters) for the i-th human subject, $\text{spDCM}_{D1\text{-}MSN, \, low\text{-}frequency}$ and $\text{spDCM}_{D2\text{-}MSN, \, low\text{-}frequency}$ are vectors of averaged network-estimates for D1- and D2-MSN stimulations at low-frequency (e.g. thresholded estimates), $\text{spDCM}_{D1\text{-}MSN, \, high\text{-}frequency}$ and $\text{spDCM}_{D2\text{-}MSN, \, high\text{-}frequency}$ are vectors of averaged network-estimates for D1- and D2-MSN stimulations at high-frequency (e.g. thresholded estimates), $\alpha_i$ and $\beta_i$ denote the contribution of D1- and D2-MSN stimulations at low-frequency to the resting-state network for the i-th human subject, $\gamma_i$ and $\delta_i$ denote the contribution of D1- and D2-MSN stimulations at high-frequency, and i runs from 1 to $N_s$, being $N_s$ the total number of participants.

In turn, this approach may generate a new set of two (multivariate) distributions: p ($\underline{\alpha}_c$, $\underline{\beta}_c$, $\underline{\gamma}_c$, $\underline{\delta}_c$) and p ($\underline{\alpha}_p$, $\underline{\beta}_p$, $\underline{\gamma}_p$, $\underline{\delta}_p$), where now the quartets: {$\underline{\alpha}_c$, $\underline{\beta}_c$, $\underline{\gamma}_c$, $\underline{\delta}_c$} and {$\underline{\alpha}_p$, $\underline{\beta}_p$, $\underline{\gamma}_p$, $\sqrt{\delta}_p$}, may denote the contribution of D1- and D2-MSN at low and high stimulation frequencies to the resting-state network for the control and parkinsonian groups respectively. Once again, by comparing the two groups, statistical differences in the neurophysiological scores: p ($\underline{\alpha}_c$, $\underline{\beta}_c$, $\underline{\gamma}_c$, $\underline{\delta}_c$) vs. p ($\underline{\alpha}_p$, $\underline{\beta}_p$, $\underline{\gamma}_p$, $\underline{\delta}_p$) may be observed, which may provide insights about the underlying biology in relation to cell types and stimulation frequencies as well.

In summary, this module estimates the same brain networks as previously estimated in animals and establishes the contribution of each cell type (and stimulation frequency) network description to resting-state human brain data. This unit may generate a set of neurophysiological scores that may serve as a diagnosis tool and also contribute to the development of new treatments (cell-specific and frequency-dependent therapeutic trials) and may potentially help to monitor the progression of a core of symptoms (e.g. dyskinesia and/or bradykinesia in PD).

Cell-Types

Medium spiny neurons (MSN), which represent 90-95% of all neurons within the striatum, include 2 intermingled subpopulations. One subpopulation of MSN express high levels of dopamine D1 receptors (together with substance P and dynorphin) (D1-MSN), and the other subpopulation express high levels of dopamine D2 receptors (together with enkephalin) (D2-MSN).

Biophysical Modeling Initiatives

Spectral DCM are deterministic models that generate predicted crossed spectra from a biophysically plausible model of coupled neuronal fluctuations in a distributed neuronal network. Neural mass modeling (NMM) describes the mean activity of entire neural populations, represented by their averaged firing rates and membrane potentials. Both approaches may be used as generative models for noninvasive brain imaging measurements; that is fMRI, MEG, and EEG.

EXAMPLES

The following examples are put forth so as to provide those of ordinary skill in the art with a complete disclosure and description of how to make and use the disclosed subject matter, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

Cell Type Specific Investigation of Global Brain Circuit Mechanisms Underlying Movement Control Using Optogenetic Functional Magnetic Resonance Imaging (ofMRI) in Mice To selectively drive D1- and D2-medium spiny neuron (MSN) in vivo, bacterial artificial chromosome (BAC) transgenic mouse lines expressing Cre recombinase under control of dopamine D1 receptor or dopamine D2 receptor regulatory elements, respectively, were used. A double-floxed inverted (DIO) recombinant adeno-associated virus (AAV) 2 virus was injected into dorsomedial striatum to express ChR2-yellow fluorescent protein (YFP) in Cre-expressing neurons, enabling selective optogenetic control of either pathway. To confirm that inhibitory medium spiny neurons of the direct (D1-MSNs) and indirect (D2-MSNs) pathways could be selectively driven in vivo, the rotational behavior of animals during repeated 20 s periods of optogenetic stimulation of dorsomedial striatum was assessed. As shown previously unilateral stimulation of either striatal D1- or D2-MSNs elicited strong contralateral and ipsilateral rotations, respectively (FIG. 3, panel C and panel F; Wilcoxon signed rank test for ipsilateral/contralateral differences between stimulation and non-stimulation periods; D1, p=0.0005; D2, p=0.002).

Figure 3:
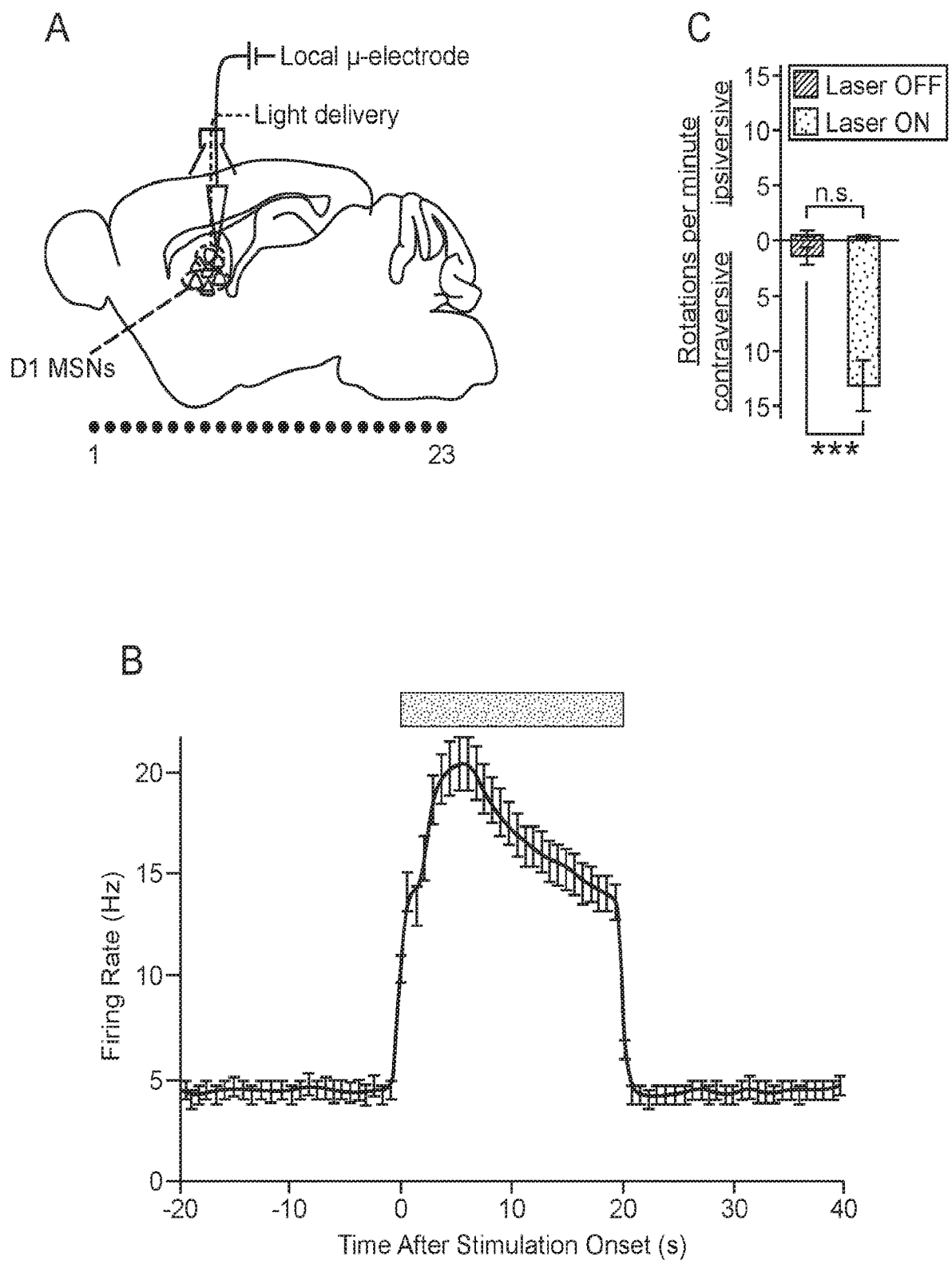
FIG. 3, panels A-J, are a collection of graphs, images and diagrams showing optogenetic fMRI (ofMRI) results with D1- and D2-medium spiny neuron (MSN) stimulations, according to embodiments of the present disclosure.
Figure 3:
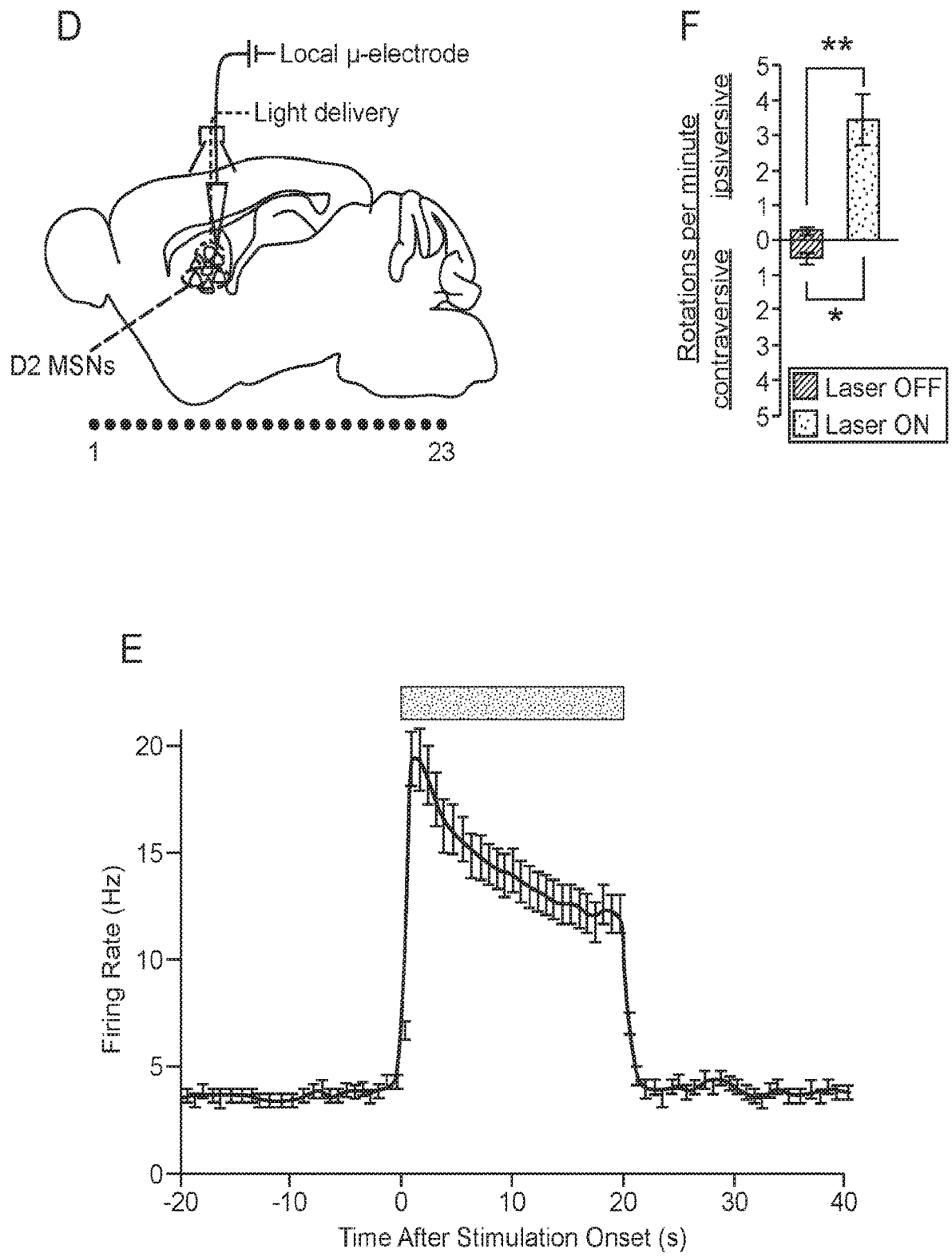
Figure 3:
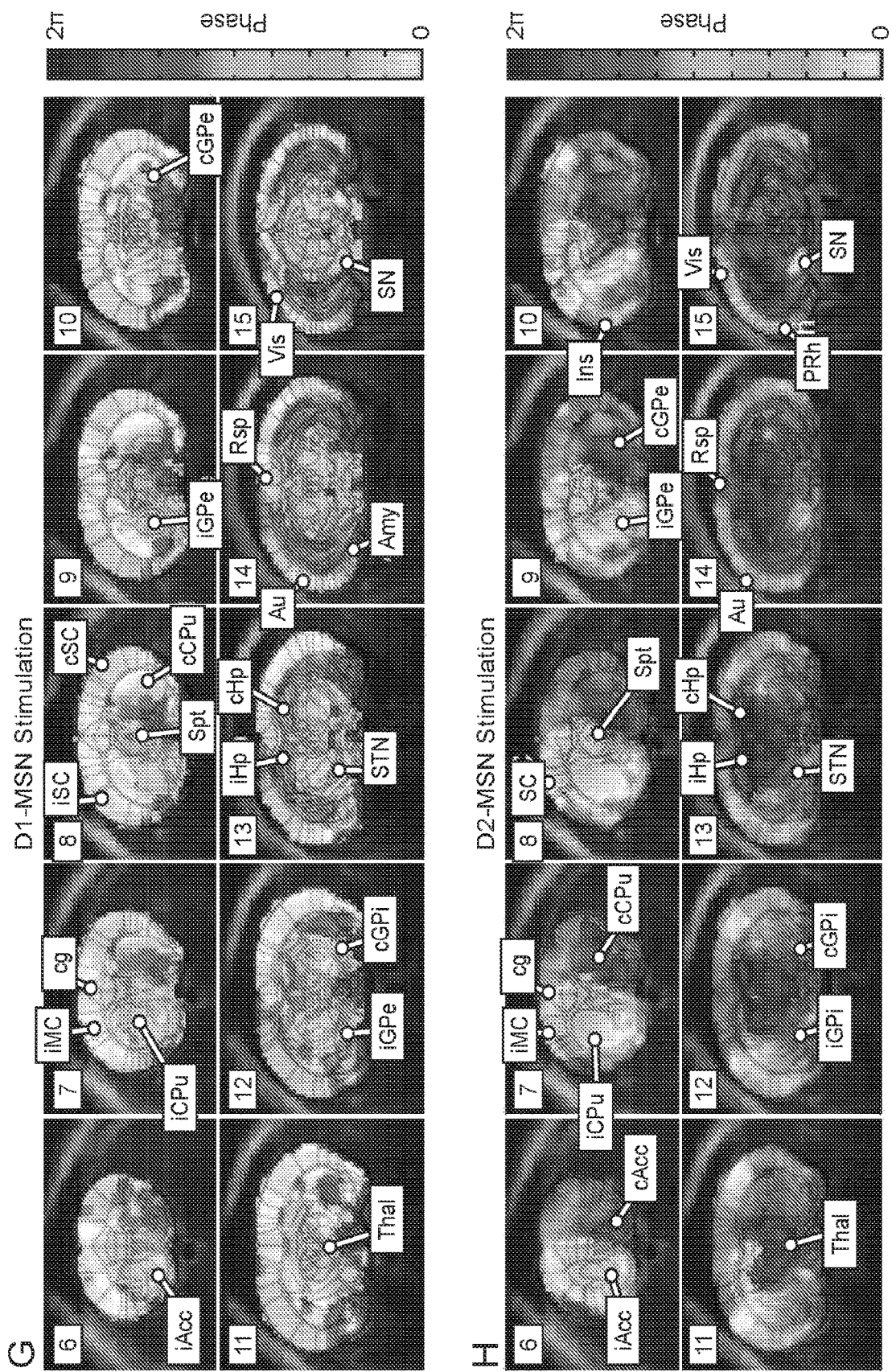
Figure 3:
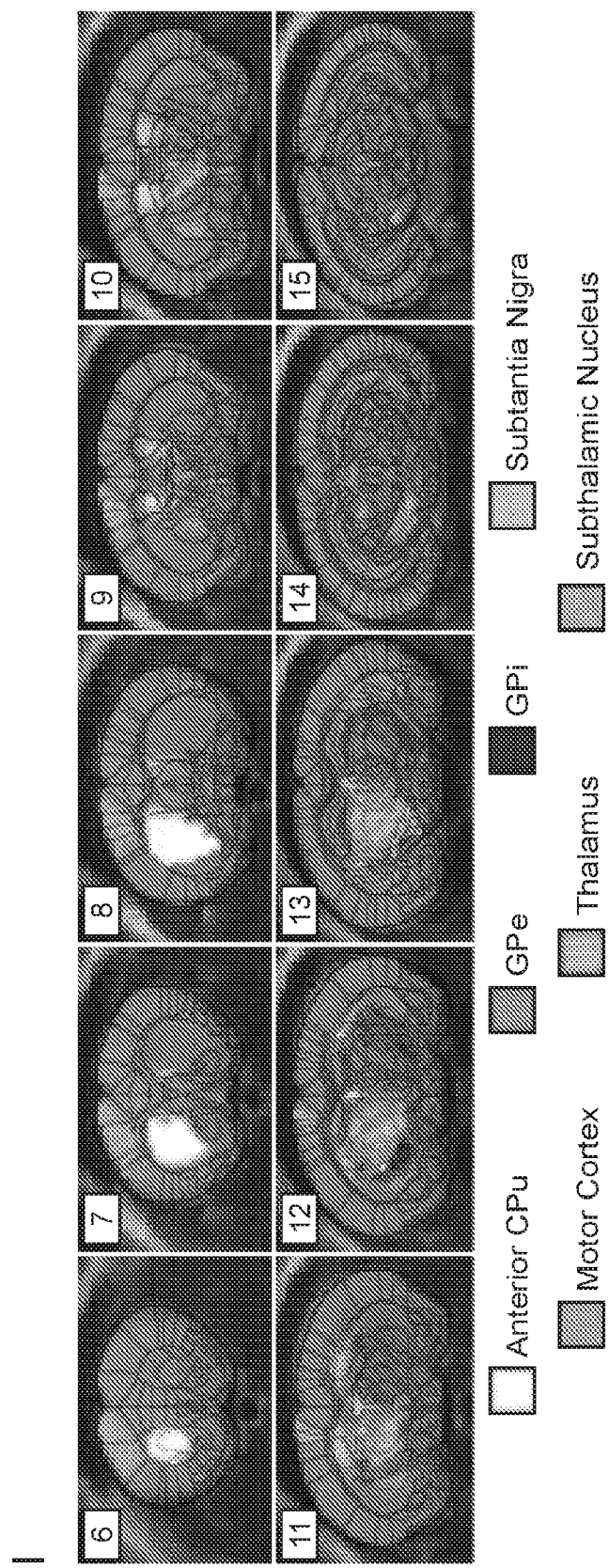
Figure 3:
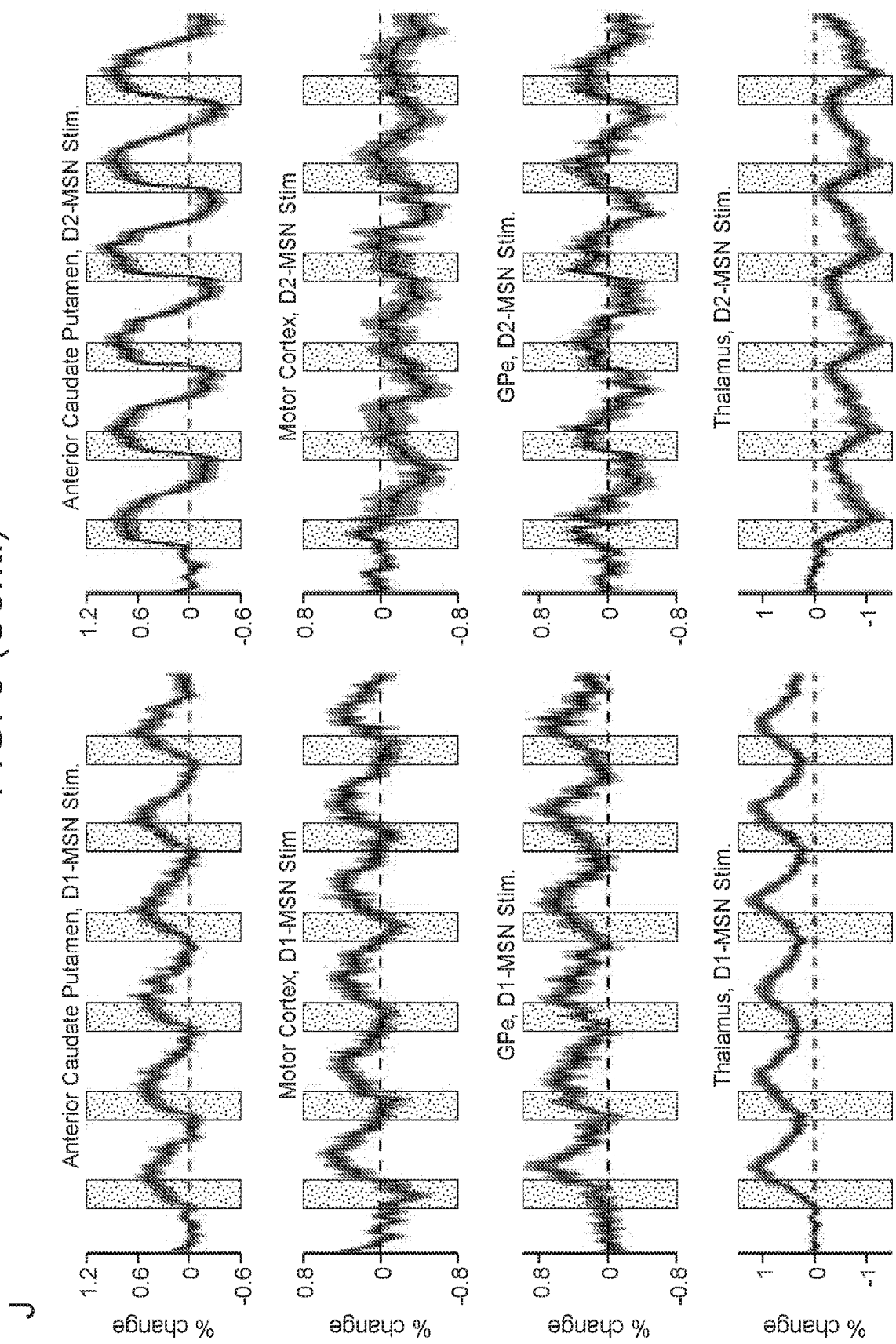
Figure 3:
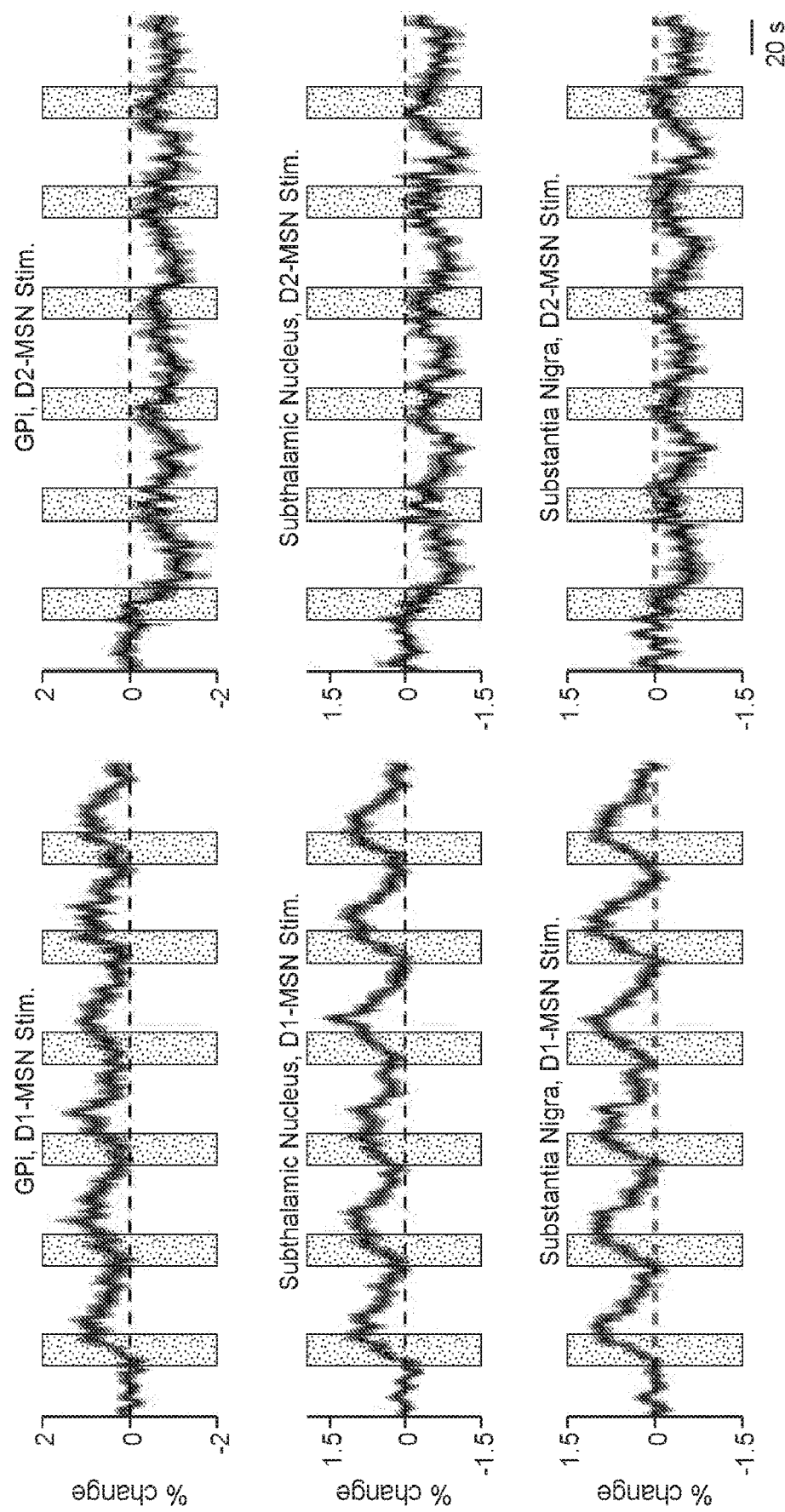

Stimulations of D1- and D2-MSNs both resulted in significant increases in striatal firing rate during in vivo extracellular recordings at the stimulation site (FIG. 3, panel B and panel E). To assess the brain-wide BOLD response driven by inhibitory D1- and D2-MSNs, whole-brain functional magnetic resonance imaging (fMRI) during repeated 20 s periods of optogenetic D1- or D2-MSN stimulation was performed. The fMRI image acquisition was designed to have 25×25 mm2 in-plane field of view (FOV) and 0.36× 0.36×0.5 mm3 spatial resolution with a sliding window reconstruction to update the image every repetition time (TR). The two-dimensional, multi-slice gradientecho sequence used a four-interleave spiral readout, 750 ms TR, and 12 ms echo time, resulting in 23 coronal slices. The spiral kspace samples were reconstructed through a 2-dimensional gridding reconstruction method. Finally, real-time motion correction was performed using a custom-designed GPU-based system. Active voxels were identified as those significantly synchronized to the repeated stimulations. Importantly, the local signal at the site of stimulation was positive for both D1- and D2-MSN stimulations (FIG. 3, panel J), confirming a widely debated issue that activity of inhibitory neurons can evoke a positive BOLD response. Interestingly, stimulation of D2-MSN resulted in larger amplitude BOLD signal. This is in good agreement with earlier findings that show that D2-MSN is more excitable for a given amount of current injection due to their higher input resistance.

The downstream basal ganglia circuit elements such as the subthalamic nuclei, substatia nigra, global pallidus, thalamus, and cortex were then segmented (FIG. 3, panel I). Due to the high image quality afforded by the technical development, signal in these areas could be successfully detected. Traditionally, fMRI signal has signal dropout and large image distortions in these areas near the air-tissue interface. Advanced shimming methods were utilized in combination with fast imaging to improve image quality. In addition, the use of robust, real-time motion correction drastically improved the ability to resolve signals arising from small nuclei.

FIG. 3, panels A-J. ofMRI with D1-, D2-MSN stimulations. FIG. 3, panel A, 20 Hz D1-MSN stim. in dorsomedial striatum results in increase of (FIG. 3, panel B) average firing rate (n=120, 100%), and (FIG. 3, panel C) num. of contralateral rotations (n=13, * P<0.001). FIG. 3, panel D, 20 Hz D2-MSN stim. in dorsomedial striatum results in increase of (FIG. 3, panel E) average firing rate (n=15, 93%), and (FIG. 3, panel F) num. of ipsilateral rotations (n=11,  P<0.005). FIG. 3, panel G and panel H, Group-wise activation maps demonstrate the large-scale modulation of cortical and subcortical regions, including the basal ganglia, during D1- and D2-MSN stimulation. Significantly modulated voxels are color-coded according to their phase relative to six repeated cycles of 20 s, 20 Hz stims. FIG. 3, panel I, Regions of interest (ROIs), used for time series extraction in FIG. 3, panel J. FIG. 3, panel J, Average time series of active voxels during D1- and D2-MSN stimulation within each ROI (left/red traces and right/blue traces, respectively). Values are mean+/−s.e.m. across animals (n=13 D1-MSN, 11 D2-MSN). Responses are generally opposite in direction with the exception of the anterior caudate putamen and globus pallidus external (GPe).

Figure 4:
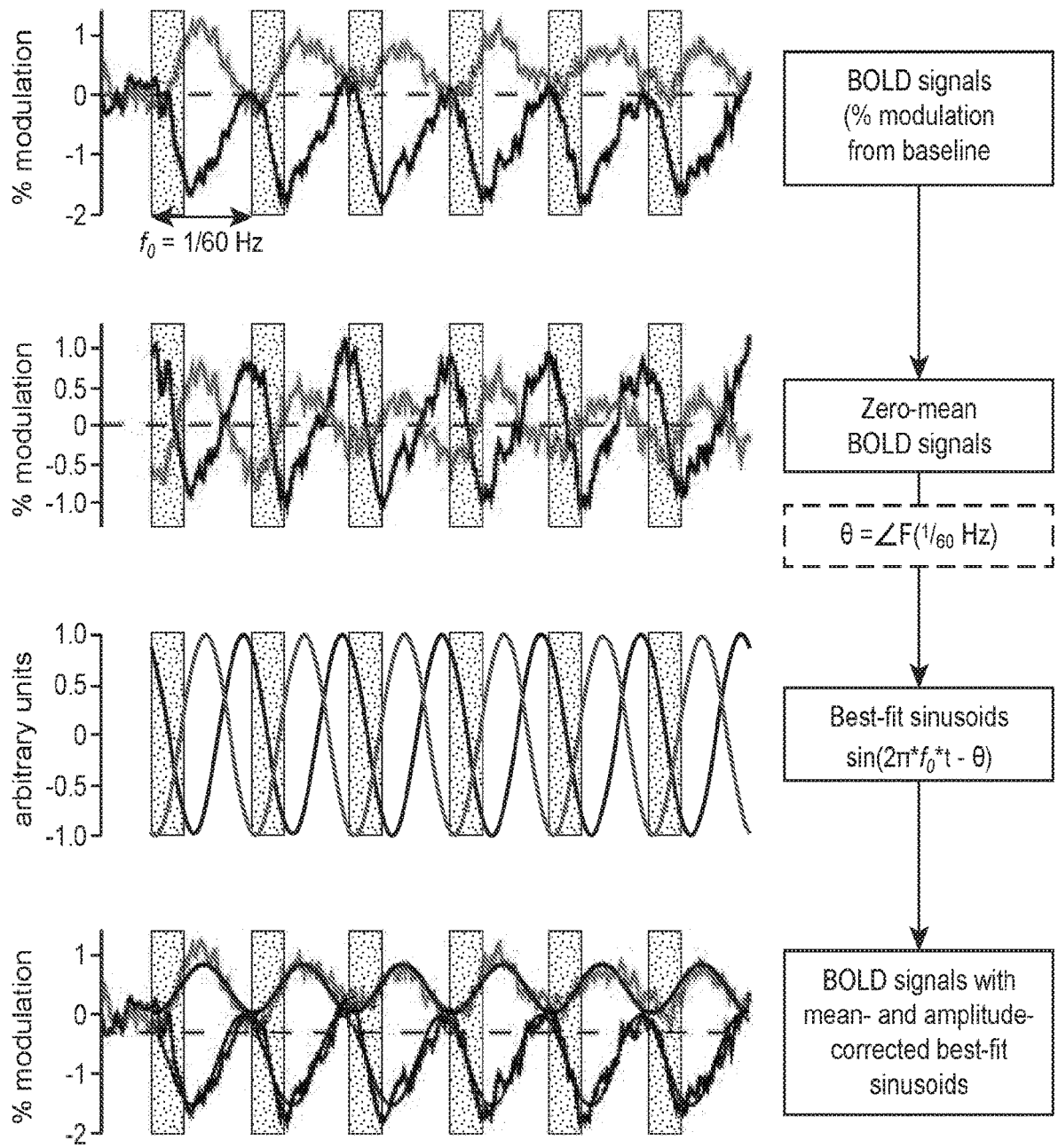
FIG. 4, panels A-D are a collection of graphs and diagrams showing that stimulations of D1- and D2-MSNs drive distinct and opposing fMRI responses, according to embodiments of the present disclosure.
Figure 4:
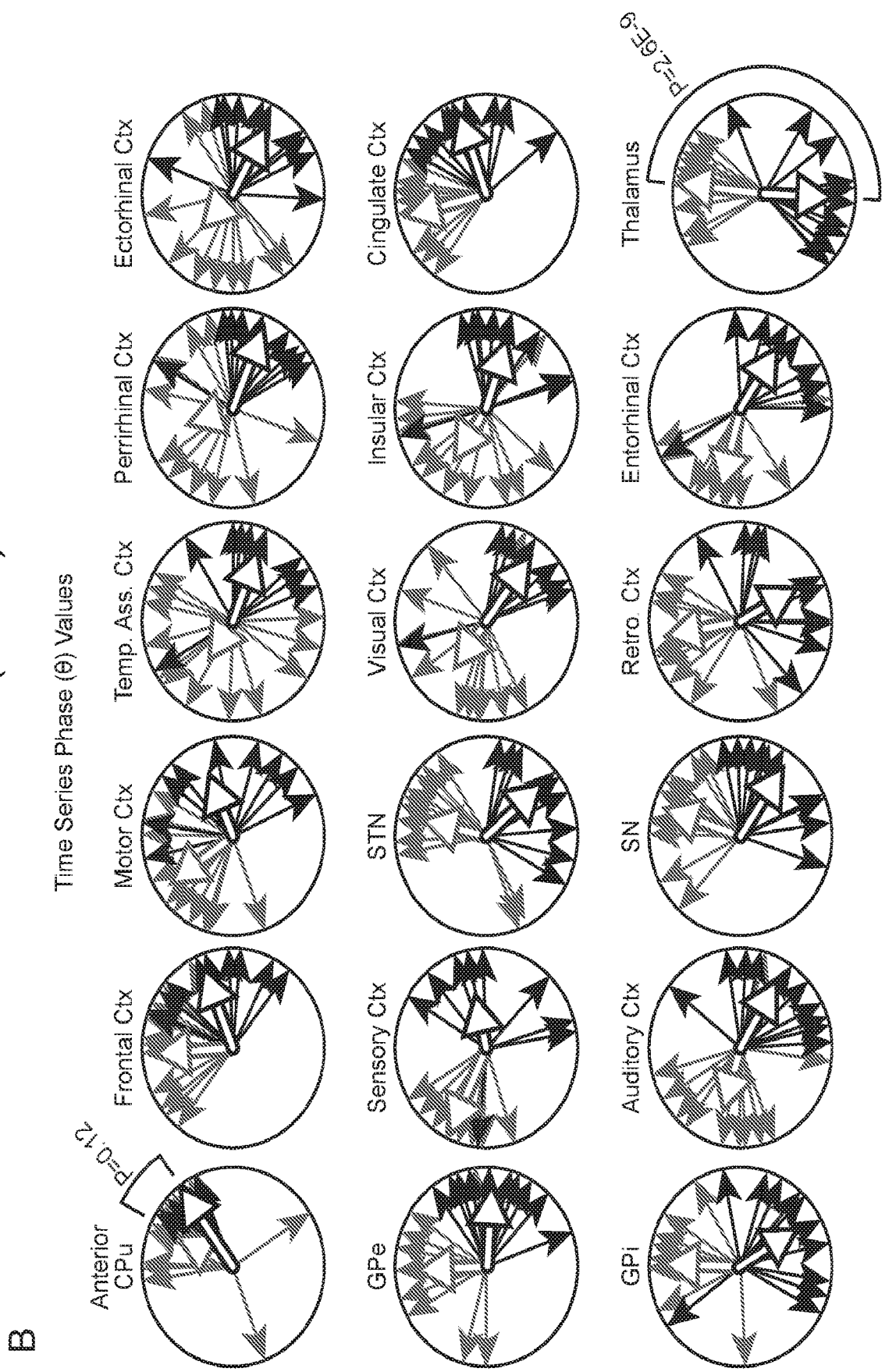

At all regions of the ipsilateral basal ganglia-thalamocortical loop other than the site of stimulation—including GPe, GPi, STN, SN, thalamus, and motor cortex—the evoked response in a given region exhibited qualitatively different temporal profiles between D1- and D2-MSN stimulation (FIG. 3, panel J). In general, positive responses were evoked during D1-MSN stimulation, while negative responses were evoked during D2-MSN stimulation. To quantify these differences in temporal patterns, the average phase of active voxels within each ROI was compared. This value represented the temporal shift of the sinusoid that best fits the modeled data (FIG. 4, panel A). The average phase of modulated voxels at the anterior caudate putamen was not significantly different between D1- and D2-MSN stimulations (FIG. 4, panel B and panel C; p>0.05, circular Watson-Williams test). In contrast, the evoked responses in GPe, GPi, STN, SN, thalamus, and all twelve segmented regions of cortex were significantly different (FIG. 4, panel B and panel C; p<0.001, circular Watson-Williams test). To further characterize the evoked responses, the integral of each ROI's time series (ΣBOLD) was next calculated (FIG. 4, panel D). With the exception of the anterior caudate putamen, all ROIs exhibited a positive mean ΣBOLD value during D1-MSN stimulation and a negative mean ΣBOLD value during D2-MSN stimulation. This difference was significant across most tested ROIs, including the basal ganglia's output nuclei GPi and SN, thalamus, and 10 of 12 segmented cortical regions (p<0.05; two-sided t-test).

FIG. 4, panels A-D. Stimulations of D1- and D2-MSNs drive distinct and opposing fMRI responses. FIG. 4A, Phase calculation for two fMRI time series. FIG. 4B, Distribution of phase values within the basal ganglia thalamocortical loop during D1- and D2-MSN stimulation. Bolded arrows indicate the average across animals. All regions, except the anterior caudate putamen (site of stimulation), exhibit significantly different phase values (p<0.001, circular Watson-Williams test; n=12 and 11 animals for D1- and D2-MSN stimulation, respectively). FIG. 4C, Histogram of p values from circular Watson-Williams tests in FIG. 4B. FIG. 4D, Quantification of ΣBOLD values for each ROI with statistical comparisons between D1- and D2-MSN stimulation.

Given the diversity of BOLD responses evoked by D1- and D2-MSN stimulation, the relationships between these two responses reflected underlying neuronal activity was next verified. Specifically, the opposing influences of the direct and indirect pathways measured on the macroscopic scale with ofMRI were also present at the level of single-unit activity. Thus, extracellular recordings in striatum and thalamus, where the differences between D1- and D2-MSN stimulation-evoked responses were least and most significant, respectively, (FIG. 4, panel C) and where the sign of ΣBOLD was the same and opposite between the two stimulation groups, respectively (FIG. 4, panel D), were performed. Although the striatal BOLD response evoked by D2-MSN stimulation was slightly larger in magnitude than the response evoked by D1-MSN stimulation, both time series exhibited clear and consistent increases upon 20 Hz light delivery (FIG. 5, panel A). Peri-event histograms from two representative neurons showed that the increase in BOLD evoked by stimulation of either pathway was associated with increases in firing rate (FIG. 5, panel B) over repeated trials. Indeed, virtually all recorded units exhibited significant increases in firing rate (FIG. 5, panel C; n=144/144 units over 7 animals and 122/123 units over 5 animals for D1- and D2-MSN stimulation, respectively, p<0.05 one-sided paired t-test). Unlike the BOLD signals observed at the site of stimulation in striatum, the fMRI BOLD signals in thalamus exhibited opposite responses during D1- and D2-MSN stimulation. Specifically, the evoked time series exhibited robust and reliable increases and decreases upon D1- and D2-MSN stimulation, respectively (FIG. 5, panel D). Peri-event time histograms from two representative neurons show that these changes were associated with corresponding changes in neuronal activity that could be consistently driven over many repeated trials (FIG. 5, panel E). Indeed, across all recorded neurons, 95% of single-units exhibited an increase in firing rate during D1-MSN stimulation (FIG. 5, panel F; n=107/114 units over 8 animals; p<0.05 onesided paired t-test). During D2-MSN stimulation, only 1% of recorded units exhibited an increase in firing rate (n=1/70 units over 5 animals; p<0.05 one-sided paired t-test). In agreement with the fMRI BOLD signal, however, 79% of cells exhibited a decrease in firing rate during D2-MSN stimulation (FIG. 5, panel F; n=55/70). Thus, the widespread opposing influences of direct and indirect pathways on thalamic activity measured with ofMRI were also confirmed at a neuronal level.

FIG. 5, panels A-F. Neuronal activity mirrors the polarity of fMRI responses evoked in striatum and thalamus during D1- and D2-MSN stimulations. FIG. 5, panel A, D1- and D2-MSN stimulations both drive robust, positive fMRI responses. mean±s.t.e across animals (n=12 and 11 for D1 and D2, respectively). FIG. 5, panel B, Peri-event time histograms of two representative neurons illustrate the immediate and sustained increase in striatal neuronal activity during both direct and indirect pathway stimulation. FIG. 5, panel C, Virtually all cells recorded in striatum during D1- and D2-MSN stimulation exhibit increases in firing rate. FIG. 5, panel D, D1-MSN stimulation drives a robust positive BOLD response, while D2-MSN stimulation drives a robust negative response in thalamus. mean±s.t.e across animals (n=12 and 11 for D1 and D2, respectively). FIG. 5, panel E, Stimulation of the direct pathway evokes a sustained increase in neuronal activity, while stimulation of the indirect pathway evokes an immediate and sustained decrease in neuronal activity. FIG. 5, panel F, Virtually all cells recorded during D1-MSN stimulation exhibit an increase in firing rate, while the majority of recorded units during D2-MSN stimulation exhibit a decrease in firing rate.

Example 2

Computational Modeling of the Basal Ganglia Pathway's Dynamic Regulation of the Whole Brain Circuit Summary of Dynamical Causal Modelling (DCM)

DCM models the brain as a dynamic system of interconnected regions during a series of specific perturbations, i.e., the experimental task. Here, the perturbation was the optical stimulation shown in Example 1. Assuming a single input defined by u(t) encodes the influence of optogenetic manipulation, i.e., a square function of zeros and ones, the state and measurement equations of DCM for optogenetic fMRI (ofMRI) responses are:

State model: $\frac{dx(t)}{dt} = f(x(t), \theta_n, u(t)) = Ax(t) + Cu(t) + \omega(t)$ Measurement model: $y(t) = g(\theta_h) * x(t) + \varepsilon(t)$ (Equation 1. State and measurement equation of a DCM for ofMRI responses in the time domain)

where x(t) represents the neuronal state, $\theta_n$=(A, C) are the neuronal parameters, A is a matrix of endogenous connection strengths, C denotes the strength of the optogenetic input, g($\theta$h) is a nonlinear convolution operator that links the neuronal state x(t) to a predicted BOLD signal y(t) via changes in vasodilatation, blood flow, blood volume, and deoxyhemoglobin content, and $\theta_h$ are the hemodynamic parameters.

Spectral DCM

Spectral DCMs are based on deterministic models that generate predicted crossed spectra from a biophysically plausible model of coupled neuronal fluctuations in a distributed neuronal network.

Spectral DCM was used to model cell type specific ofMRI data. The autoregressive models of first order, i.e. AR(1) processes, that parameterized fluctuations at the neuronal, i.e., $\omega$(t), and observation level, i.e., $\varepsilon$(t). Eq. 1 were rewritten in the frequency domain as:

State model: $X(f) = (j2\pi f - A)^{-1}(CU(f) + \omega(f))$

Measurement model: $Y(f) = G(\theta_h)(j2\pi f - A)^{-1}(CU(f)) + \omega(f) + \varepsilon(f)$ (Equation 2. State and measurement equations of a DCM for ofMRI responses in the frequency domain)

Cross-spectral responses: $G_y(f) = Y(f)Y(f)^* = S(f)G_i(f)S(f)^* + G_\varepsilon(f)$ (Equation 3. Cross-spectral responses)

where $G_u(f) = PSD\{u(t)\}$, $G_\omega(f) = \frac{\sigma_\omega^2}{|1 - AR_{1,\omega}e^{-j2\pi f}|^2}$, and $G_\varepsilon(f) = \frac{\sigma_\varepsilon^2}{|1 - AR_{1,\varepsilon}e^{-j2\pi f}|^2}$.

$G_u(f)$ is the power spectral density (PSD) of the experimental input, $G_\omega(f)$ is the spectral density of endogenous neural fluctuations parameterized as autoregressive processes of order 1, and $G_\varepsilon(f)$ is the spectral density of the observation noise also parameterized as autoregressive processes of order 1. $\sigma_\omega^2$ and $\sigma_\varepsilon^2$ are the variance of the above-mentioned autoregressive processes and $AR_{1,\omega}$ and $AR_{1,\varepsilon}$ their corresponding autoregressive coefficients. $S(f)=G(\theta_h)(j2\pi f-A)^{-1}$ denotes the transfer function (TF) and $G_i(f)=CG_u(f)C^T+G_\omega(f)$ the input function. With this mathematical formulation, endogenous neural fluctuations could be included, i.e. the $G_\omega(f)$ term (stochastic modeling), or not be included (deterministic modeling).

Model Inversion and Bayesian Model Selection (BMS)

Using the cross-spectral responses described in Eq. 3, models were inverted using variational free energy under the Laplace approximation. In this study, an estimate of the negative free-energy was used as an approximation to the log model evidence. To select the optimal type of modeling (i.e. stochastic or deterministic), Bayesian model selection (BMS) for fMRI responses was used. In this setting, searching for the optimal model corresponded to selecting the model that represents the best balance between fit and complexity. A random effects BMS scheme at the group level that accounts for potential heterogeneity across subjects was also employed. Including the neural fluctuations resulted in better model fit.

Results ofMRI was used to investigate the contribution of two cell-types on basal ganglia pathways. Within this modelling unit, spectral DCM (spDCM) was used to estimate the effective connectivity among brain regions. A 7-node brain network consisting of the following regions was modeled: caudate-putamen aspect (CPu), globus pallidus external segment (GPe), globus pallidus internal segment (GPi), subthalamic nucleus (STN), substantia nigra (SN), thalamus (THL), and motor cortex (MOT) aspects ipsilateral to the stimulation site. To constrain the models, anatomical connectivity information in the literature was searched to select the most likely generative model for the data among neurobiologically plausible candidates (FIG. 6).

Figure 7B:
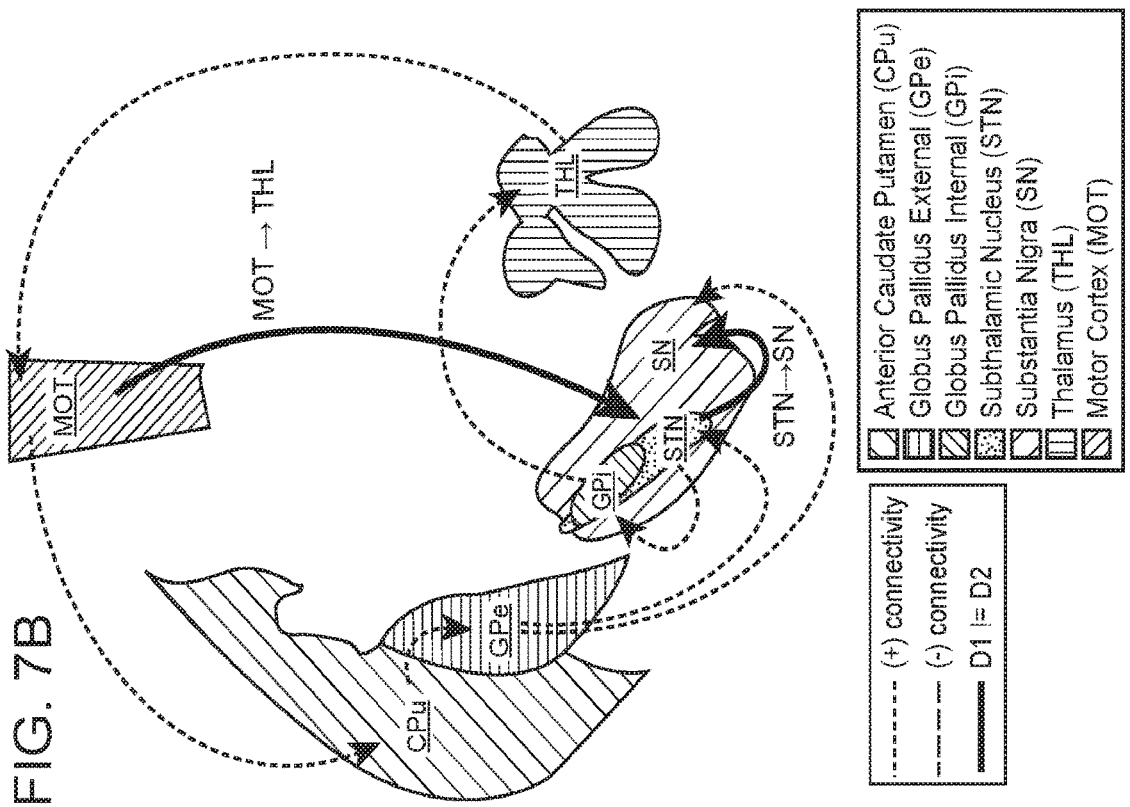
FIGS. 7A-7C are a collection of schematic diagrams and graphs showing spectral dynamic causal modeling of whole brain circuit function driven by basal ganglia pathways, according to embodiments of the present disclosure.
Figure 7A:
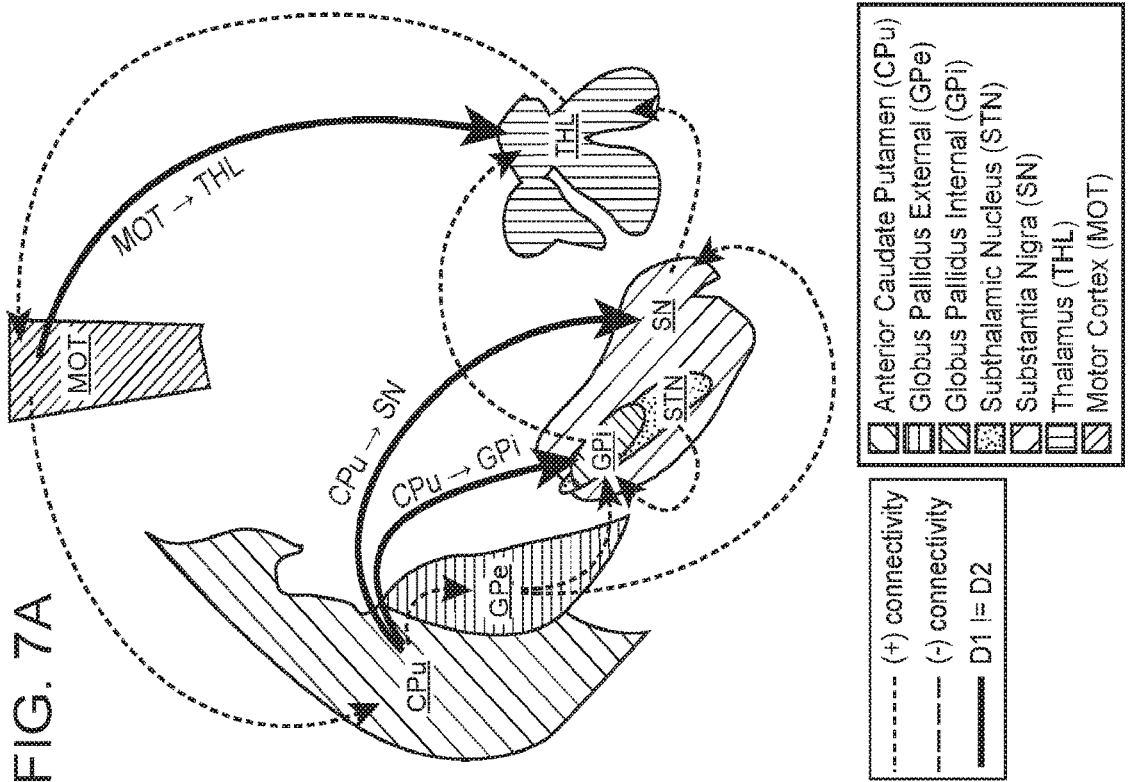
Figure 7C:
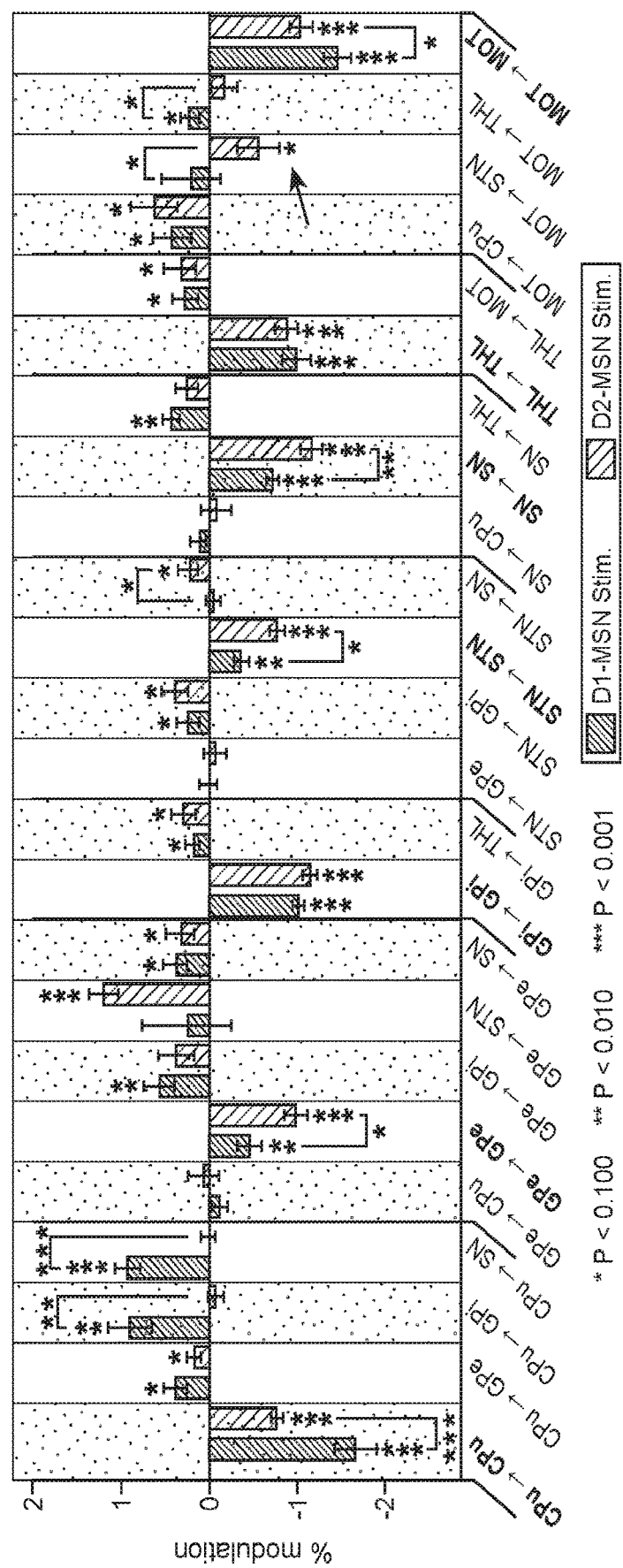

The measured ofMRI responses with D1- and D2-MSN stimulations at 20 Hz was modeled using spectral DCM. Connectivity that quantifies the overall information flow (not anatomical connectivity) from one region to the other were estimated using spectral DCM (FIGS. 7A-7C). The results clearly showed that connectivity estimates differed significantly between stimulation of the two neuron types, reflecting the distinct dynamics of the two pathways. More specifically, the striatal connections to the two output nuclei of the basal ganglia were greater during D1-MSN stimulation in comparison to D2-MSN stimulation, a finding well supported by the literature. Likewise, connection from motor cortex to thalamus was also greater in D1-experiments. On the other hand, connection from subthalamic nucleus to substantia nigra was stronger in D2-manipulations and connection from motor cortex to subthalamic nucleus had negative polarity in D2-manipulations.

Thus, there was direct information flow from striatum (Cpu) to internal globus pallidus (Gpi) and substantia nigra (SN) only in the D1-MSN direct pathway, consistent with the classical model of basal ganglia circuitry. On the other hand, sub thalamic nuclei (STN) to SN information flows were only present in the D2-MSN indirect pathway. These results provide a possible mechanistic link where beta band stimulation of D2-MSN resulted in strong inhibitory influence from motor cortex to STN (FIG. 7B).

FIGS. 7A-7C. Spectral dynamic causal modeling of whole brain circuit function driven by basal ganglia pathways. Spectral dynamic causal modeling of the ofMRI data with D1- and D2-MSN stimulation at 20 Hz gives quantitative estimation of connectivity (information flow) across the basal ganglia pathways. Connectivity with 20 Hz stimulation of (FIG. 7A) D1- and (FIG. 7B) D2-MSN, respectively. (FIG. 7C) Mean connectivity estimates for D1- (black) and D2-(grey) MSN stimulation experiments. Black star indicates locations that show statistically significant connections: * p<0.1,  p<0.01, * p<0.001.

Example 3

Quantitative Modeling of Human fMRI Data for the Diagnosis of Movement Disorders with Cellular Precision Data previously collected as part of the K23 NS075097 and P50 AG047366 (Stanford ADRC) is used. Over the 5-year course of the project, imaging data from 498 individuals will be used. Specifically, 245 patients with Parkinson's disease (PD) and 243 neurologically normal control data from these two studies will be included in this proposal. The subjects with mild cognitive problems are included because the research hypotheses pertain to these populations. The 118 participants (80 PD off and on medication and 38 normal control) from K23 are already recruited and have completed all study procedures. The remaining 370 (165 PD off and on medication and 205 normal control) participants from P50 AG047366 (Stanford ADRC) are currently being recruited. For the scans 29 axial slices with 4.0 mm thickness have been acquired, 0.5 mm skip were collected in parallel to the AC-PC line, covering the whole brain, using a T2*-weighted gradient-echo spiral in-out pulse sequence with the following parameters: repetition time=2 sec, echo time=30 msec, flip angle=80°, field of view was 20 cm, and matrix size of 64×64, providing an inplane spatial resolution of 3.125 mm. The ADRC data will be collected with TR=490 ms, TE=30 ms, flip angle=45°, isotropic 3 mm resolution. Multiband acquisition is used with an acceleration factor of 6 (number of slices acquired simultaneously) acquiring 42 slices and acquire order of [1; 5; 2; 6; 3; 7; 4], field of view of 222×222 mm.

Example 4

Brain Circuit Function with Dynamic Causal Modeling for Optogenetic fMRI

Summary

Experiments were performed to develop a dynamic and cell-type-specific connectivity map from simultaneous measurements across the brain. For such dynamic causal modeling (DCM), optogenetic fMRI experiments were performed, which allowed for cell-type-specific, brain-wide functional measurements to be obtained, which were used to parameterize the causal relationships among regions of a distributed brain network with cell type specificity. When applied to the brain-wide basal ganglia-thalamocortical network, DCM accurately reproduced the empirically observed time series, and the strongest connections were key connections of optogenetically stimulated pathways. Quantitative and cell-type-specific descriptions of dynamic connectivity can be used to determine a systems-level understanding of neuronal circuit dynamics and facilitate the design of more effective neuromodulation therapies.

Introduction

Many of the nervous system's key functions are orchestrated by large-scale distributed networks across the brain, including the basal ganglia-thalamocortical circuit, responsible for motor control. The effective connectivity among multiple brain regions and neuronal populations was determined in order to understand the circuit mechanism underlying motor control. Effective connectivity is conventionally defined as the causal or directed coupling between brain regions, whereas functional connectivity refers to the correlations between them. Determining these causal relationships may facilitate a better understanding of neurological disease involving the basal ganglia and allow for the optimization of therapies for movement disorders, such as deep brain stimulation (DBS) for Parkinson's disease.

Functional MRI (fMRI) provides non-invasive measurements of neural activity across large-scale brain networks through surrogate hemodynamic responses like the blood oxygenation level dependent (BOLD) signal. The basal ganglia-thalamocortical network can be used to define cell-type-specific network function. The striatum—the primary input structure of the basal ganglia—has distinct cell types including D1- and D2-receptor-expressing medium spiny neurons (D1- and D2-MSNs), which send unique inhibitory projections to surrounding basal ganglia nuclei. D1-MSNs project directly to the two output nuclei of the basal ganglia—the internal globus pallidus and the substantia nigra pars reticulata—and are thought to promote motor behavior via disinhibition of downstream thalamocortical circuits, while D2-MSNs project indirectly to the two output nuclei via the external globus pallidus and subthalamic nucleus, and are thought to inhibit movement by suppressing thalamocortical circuits.

Optogenetic fMRI (ofMRI) can be used for monitoring of brain-wide functional activity resulting from cell-type-specific perturbations. For example, opposing patterns of activity across the basal ganglia-thalamocortical network were characterized upon selective stimulation of either D1- or D2-MSNs. Temporal signal patterns across the brain were precisely traced and found to generally match the underlying single-unit electrophysiology.

In the experiments performed herein, dynamic causal modeling (DCM) was used to parameterize causal relationships among regions of a distributed brain network with cell type specificity. DCM is a Bayesian procedure that allows one to estimate coupling (effective connectivity) and evidence for different network models of neuroimaging data. A wide variety of models may be used, including non-linear models, stochastic approaches, and spectral formulations. In stochastic DCM, both the effective connectivity and endogenous (neuronal) fluctuations are estimated. Stochastic DCM has been subject to neurobiological validation using simultaneous EEG-fMRI recordings and has been shown to offer high reproducibility. Spectral DCM (spDCM) parameterizes endogenous fluctuations and adapts a deterministic model of neuronal activity, which leads to a significant increase in computation speed compared to stochastic DCM.

In this Example, spectral DCM was used to investigate the interactions among basal ganglia-thalamocortical network regions with cell type specificity and link the observed activation patterns to quantitative parameters that represent effective connectivity strengths. The dynamic causal modeling approach was used to determine functional relationships underpinning brain-wide networks with cell type specificity beyond the basal ganglia.

Results

Dynamic Causal Modeling of ofMRI Data

In order to computationally model the D1- and D2-MSN stimulation ofMRI data and identify effective connective strengths, spectral DCM was used. For fMRI, DCMs can either be fitted to the time series directly (standard DCM) or to the cross spectral density of the data after applying a Fourier transform (spectral DCM). Both standard and spectral DCM can also include endogenous fluctuations beyond experimental effects. Although experimental effects and endogenous fluctuations are normally not considered together, the fMRI time series used in this Example were elicited under optogenetically controlled experimental stimuli (i.e., a deterministic input), which allowed for a comparison of deterministic and stochastic models of the same data. It was also determined whether stochastic endogenous fluctuations were necessary for explaining the data. Therefore, a Bayesian model comparison was performed using spectral DCM with and without endogenous fluctuations. To quantify the quality of fit of the spectral DCM, the posterior estimates from the spectral DCM were used as priors in a standard (stochastic) DCM and the time series was reinverted. This provided predicted responses in the time domain that were then compared to the observed signal. A network model was selected to use as the a priori generative model based on known basal ganglia anatomy. A seven-node brain network was used, which included the caudate-putamen (CPu), external globus pallidus (GPe), internal globus pallidus (GPi), subthalamic nucleus (STN), substantia nigra (SN), thalamus (THL), and motor cortex (MCX). An alternative network defined by the replacement of motor cortex with sensory cortex (SCX) was also modeled to examine the network's stability, defined here as the stability of connectivity estimates upon perturbations to the network.

Figure 9:
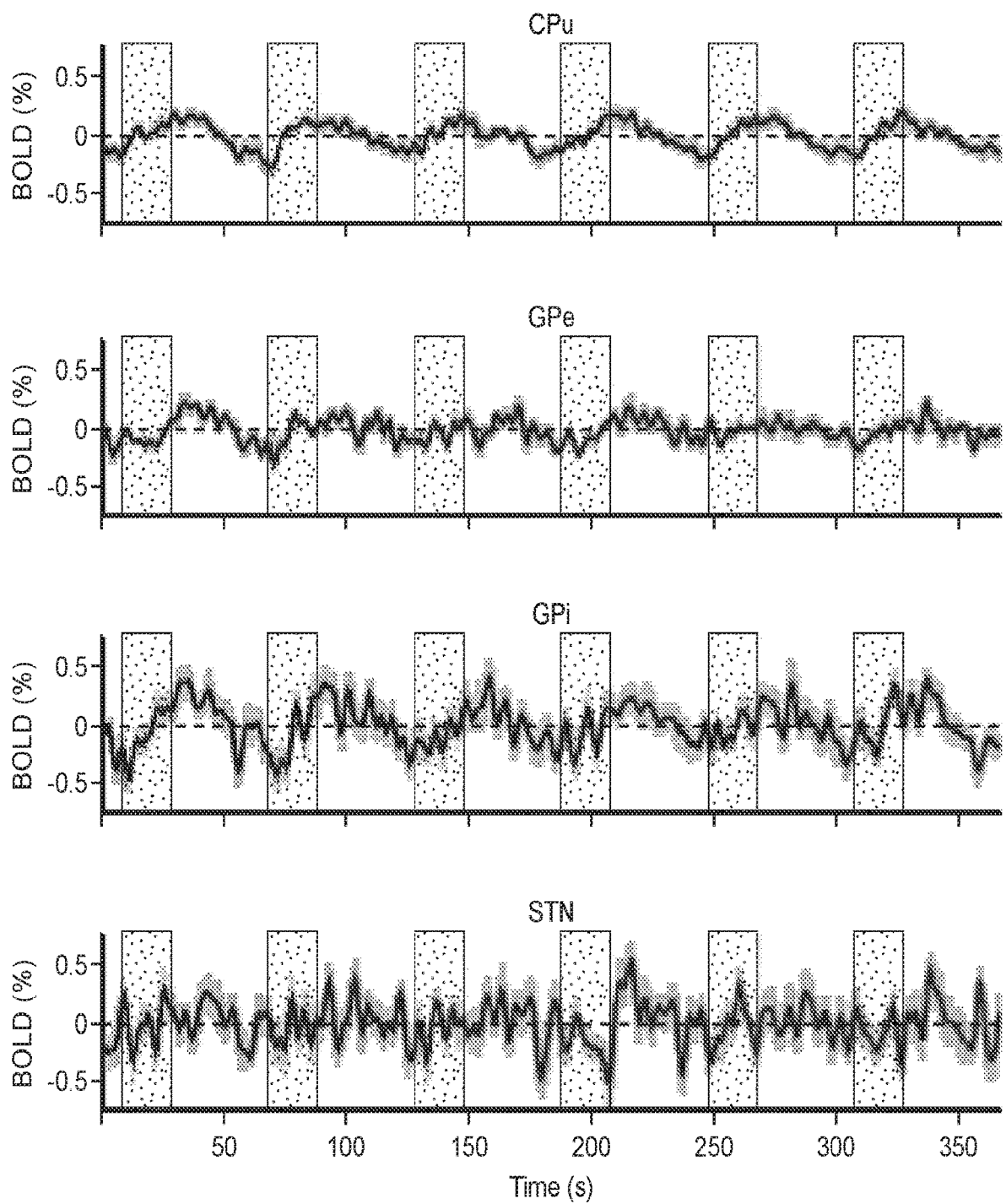
FIG. 9, panels A-D, are a collection of images and graphs of anatomical masks and time series extracted from regions of interest within the basal ganglia-thalamocortical network, according to embodiments of the present disclosure.
Figure 9:
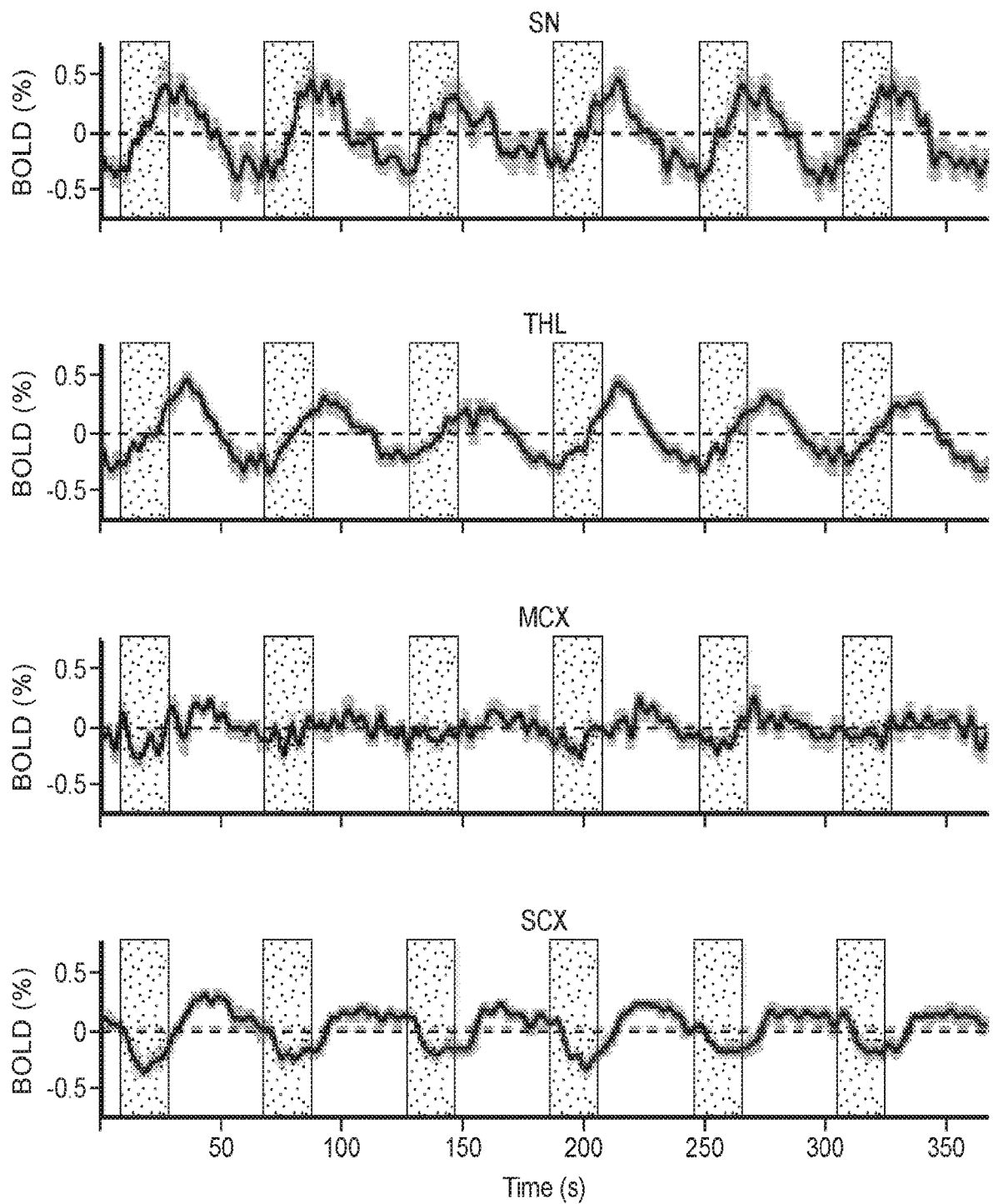
Figure 9:
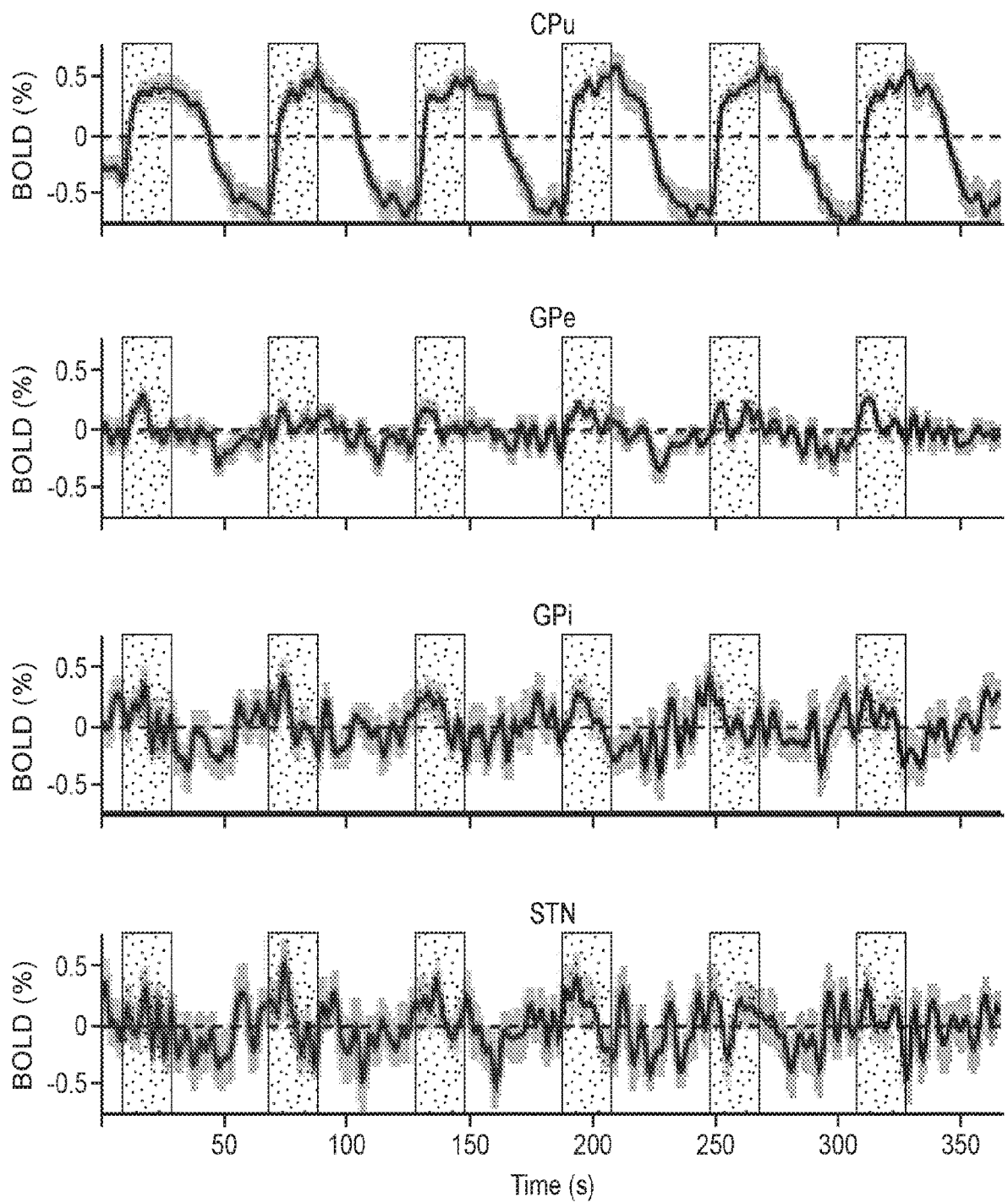
Figure 9:
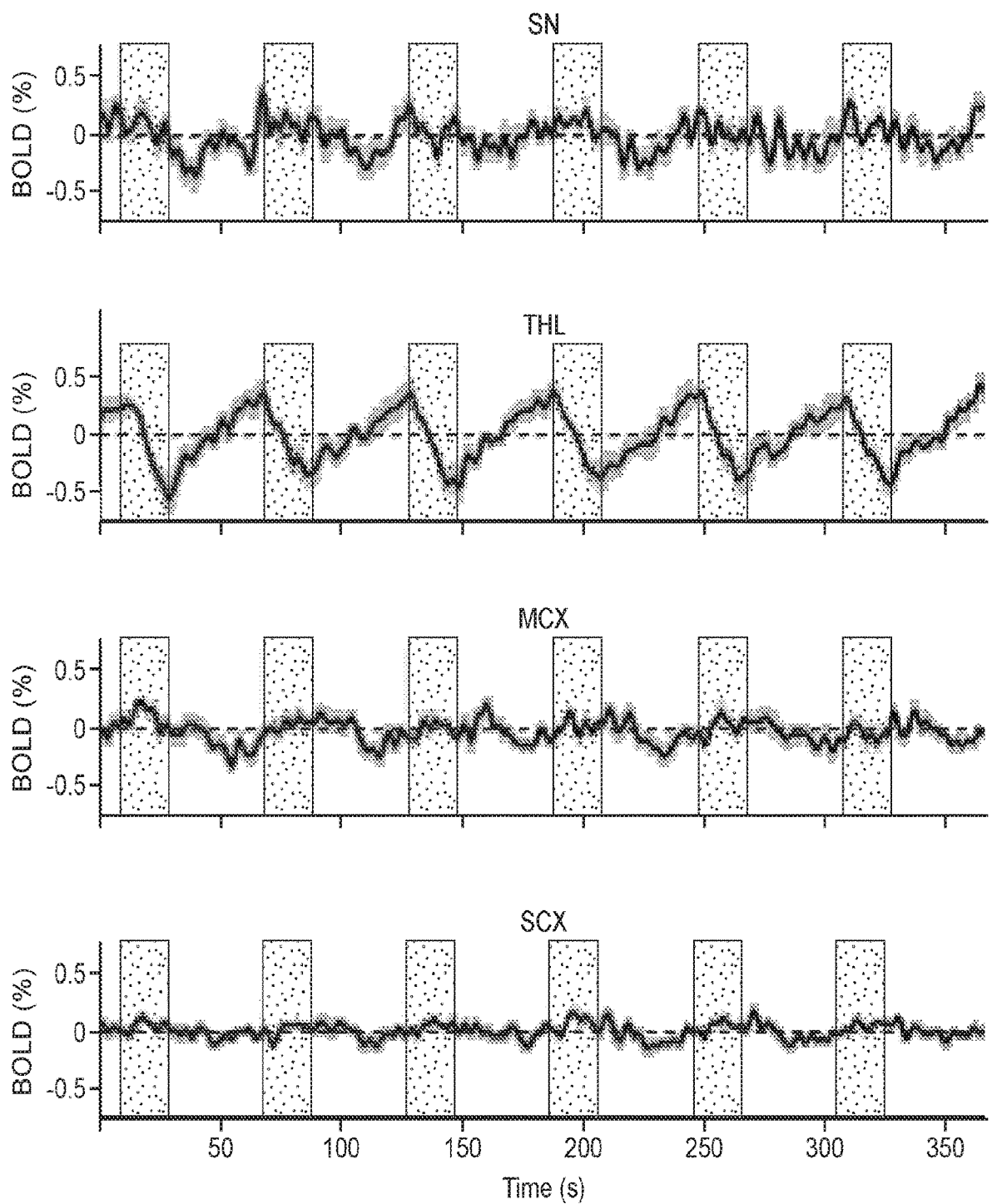
Figure 11:
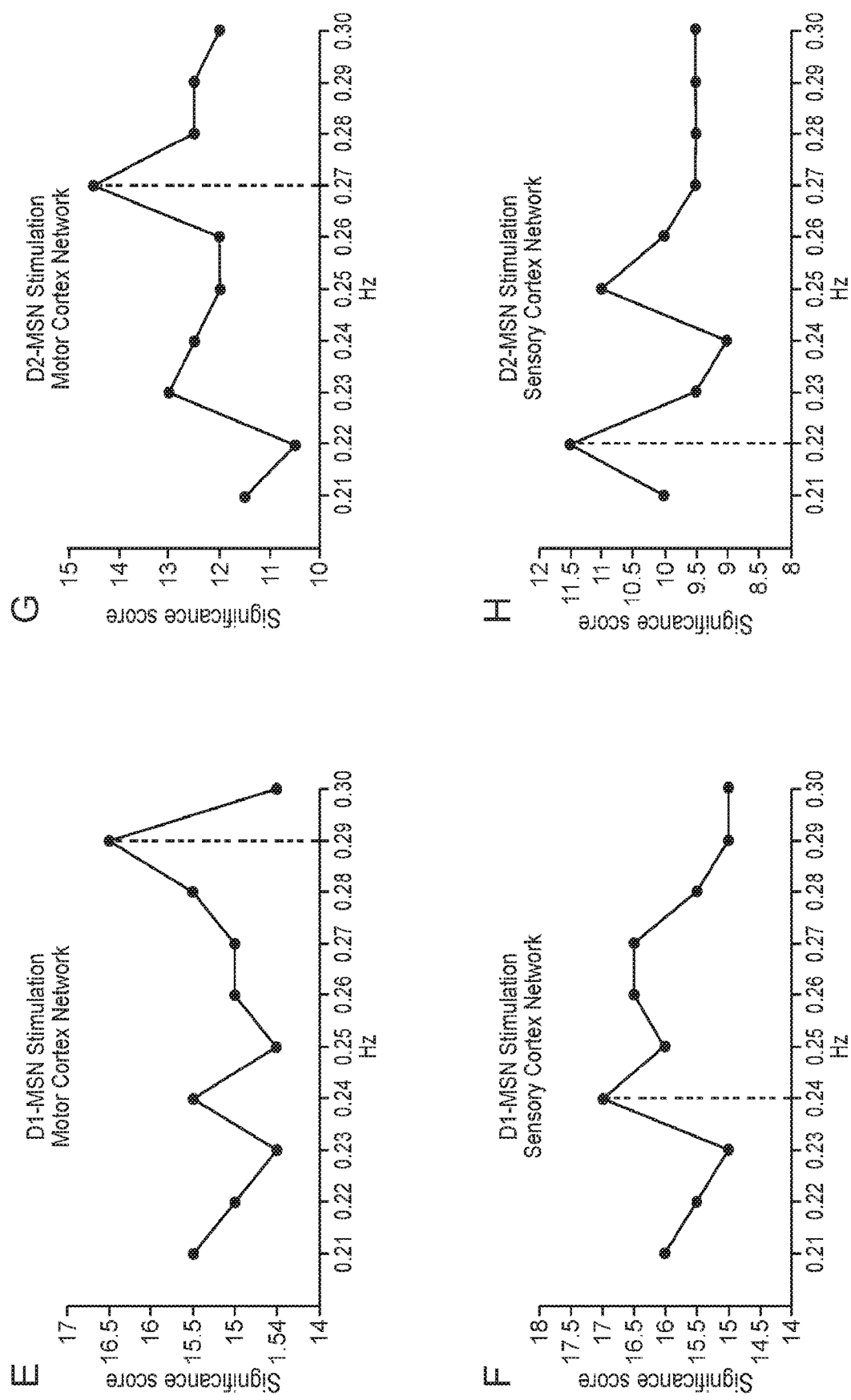
FIG. 11, panels A-H, are a collection of graphs illustrating significant and close-to-significant connections during D1- and D2-MSN stimulations for the MCX and SCX network models at each cutoff frequency, according to embodiments of the present disclosure.

Anatomical regions of interest were defined for each node and a voxel-averaged fMRI time series was extracted (FIG. 9, panels A-D). FIG. 10, panels A and B, depict the a priori connection scheme of the generative model employed throughout the study. Connectivity estimates were computed after low-pass filtering the time series with ten different cutoff frequencies, and the significance of each connection was determined at each cutoff by testing its connectivity estimate against zero across subjects (D1: n=12 and D2: n=10). False discovery rate (FDR) was used to correct the resulting p values for multiple tests of network connections (at the between-subject level). Significant variability in the p values was observed across cutoff frequencies (FIG. 11). For the model's final output, the filter cutoff was selected that maximized a weighted sum of the number of significant and close-to-significant connections. Connections with a corrected p value less than 0.05 were considered significant, while those having a corrected p value between 0.05 and 0.10 were considered close-to-significant. The same criteria were applied for statistical significance when comparing connections under D1- and D2-MSN stimulations and MCX and SCX networks.

To model endogenous fluctuations and observation noise parameters within the model, autoregressive models of order one to four, parameterized by amplitude and autoregressive model coefficients, were used. As described above, the importance of endogenous fluctuations in each network was also determined by comparing results with and without endogenous fluctuations in the model equations for stochastic and deterministic modeling, respectively. In particular, random effects Bayesian model selection (BMS) was used to select which of the two modeling approaches provided the greatest model evidence—in other words, the best balance between accuracy and complexity—and to examine the optimal order of autoregressive processes. The experiments described herein included autoregressive modeling, a comparison of models with and without endogenous fluctuations, and the optimized selection of a low-pass filter cutoff frequency.

D1- and D2-MSN Stimulation Networks

Significant connections during D1-MSN stimulations were largely consistent with direct pathway activation (FIG. 12, panels A and D). Mean connectivity estimates with 95% confidence intervals across subjects and uncorrected and corrected p values are provided in Table 3, which is shown in FIG. 13. Remarkably, the projections exhibiting the strongest connectivity estimates in both MCX and SCX networks were those from CPu to GPi (mean connectivity estimate: 0.9177 Hz, p value [corrected]: 0.0072, in the MCX network) and from CPu to SN (mean connectivity estimate: 0.9155 Hz, p value [corrected]: $3.6572 \times 10^{-5}$, in the MCX network), the two defining connections of the direct pathway. Upon using the posterior estimates from the spectral DCM as priors in a standard (stochastic) DCM, the resulting time series reproduced the amplitude, polarities, and delays of the empirically observed BOLD responses across brain regions for both MCX and SCX network models (FIG. 12, panels B and E). In general, stochastic models (with endogenous fluctuations) were better than deterministic models. For the MCX network, the exceedance probability of stochastic modeling (i.e., the probability that this modeling approach was more likely than any other modeling approach considered) was 0.9148 (FIG. 12, panel C). For the SCX network, the model exceedance probability of stochastic modeling was 0.5918 (FIG. 12, panel F).

The brain-wide fMRI responses to D2-MSN stimulation significantly differed from those evoked by D1-MSN stimulation. In particular, many of the subcortical regions exhibited a decrease in signal during stimulation. Importantly, using the same a priori network described above now led to significant connections that reflected activation of the indirect pathway (FIG. 14, panels A and D). Mean connectivity coefficients with 95% confidence intervals across subjects and uncorrected and corrected p values are listed in Table 4, which is shown in FIG. 15. The greatest connection in both MCX and SCX network models was from GPe to STN (mean connectivity estimate: 1.1176 Hz, p value (corrected): $5.7809 \times 10^4$, in the MCX network), a key projection of the indirect pathway. The time series calculated from these posterior estimates also accurately matched the distinct BOLD responses elicited by D2-MSN stimulation, such as the robust negative signal within the thalamus (FIG. 14, panels B and E). As with D1-MSN stimulations, stochastic models were better than deterministic models in a majority of subjects. The exceedance probability of stochastic modeling was 0.6025 for the MCX network (FIG. 14, panel C) and 0.7529 for the SCX network (FIG. 14, panel F).

In light of the close relationship between model estimates and underlying physiology, the same modeling framework was used to estimate networks during D1- and D2-MSN stimulations. The generative model, fluctuations, and priors remained the same. This demonstrated that the proposed algorithm can be generalized for use in parameterizing different optogenetic fMRI experiments.

Comparison Between MCX and SCX Network Models

The stability of D1-MSN-driven networks was examined. The exchange of MCX with SCX did not change the strength of any connection within the model (FIG. 16, panel A; and FIG. 17, Table 5), supporting the idea that motor and sensory cortices generally exert homologous influence on basal ganglia circuitry during D1-MSN stimulations. Similarly, the replacement of motor cortex with sensory cortex for the D2-MSN stimulation models did not significantly change the strength of inter-regional connectivity estimates (FIG. 16, panel B; and FIG. 17, Table 5). Only the self-connection within cortex was different in strength after replacement (close-to-significant, p<0.10). Collectively, these results demonstrated the stability of dynamic causal modeling in D1- and D2-MSN stimulation networks.

Comparison Between D1- and D2-MSN Stimulation Network Models

To provide a quantitative comparison of the D1- and D2-MSN stimulation network models, statistical comparisons of each model's resulting connectivity estimates were performed (FIG. 18; and FIG. 19, Table 6). Connections from CPu to GPi and from CPu to SN—the defining projections of the direct pathway—were significantly greater during D1-MSN stimulations in both MCX and SCX networks. The connection from STN to SN—another significant projection within the indirect pathway—was greater during D2-MSN stimulations in the SCX network (close-to-significant, p<0.10). Differences were also observed in the strength of cortical efferents between the D1- and D2-MSN stimulations. On the other hand, the connection from MCX to THL was significantly greater during D1-MSN stimulations. These projections were generally positive during D1-MSN stimulation and negative during D2-MSN stimulations. There were also several significant differences in intra-regional estimates between D1- and D2-MSN stimulations (FIG. 19, Table 6).

The self-connection parameters within the CPu were significantly greater in magnitude (more negative) during D1-MSN stimulations in both MCX and SCX networks. In the GPe, the self-connection parameter was significantly greater in magnitude (more negative) during D2-MSN stimulations in the MCX network. The self-connection parameters in GPi were also greater in magnitude (more negative) during D2-MSN stimulations in the SCX network (close-to-significant, $p<0.10$). Likewise, the self-connection parameter in STN was greater in magnitude (more negative) during D2-MSN stimulations in the MCX network (close-to-significant, $p<0.10$). The self-connection parameters within SN were significantly greater in magnitude (more negative) during D2-MSN stimulations in both MCX and SCX networks. Finally, in the SCX network, the self-connection parameter in SCX was significantly greater in magnitude (more negative) during D2-MSN stimulations.

Discussion

While circuit diagrams of basal ganglia pathways have been traditionally delineated by measuring anatomical connectivity and electrophysiological activity in isolation, they have never been simultaneously and directly measured across the brain. The presently disclosed model makes use of brain-wide optogenetic fMRI measurements to construct a cell-type-specific dynamic brain circuit diagram based on data measured in live subjects. In these experiments, a computational approach was developed that can parameterize the brain-wide network function measured by fMRI responses evoked during cell-type-specific stimulations of D1- or D2-receptor-expressing striatal MSNs. Surprisingly, the strongest connections during D1-MSN stimulation were the efferents from the CPu to GPi and SN, while the strongest connection during D2-MSN stimulation was from GPe to STN, the key projections of the direct and indirect pathways, respectively. Comparisons of connectivity estimates between the two stimulation groups also showed that connections belonging to the direct pathway were greater during D1-MSN stimulation, and connections belonging to the indirect pathway were greater during D2-MSN stimulation. These findings confirmed the presently disclosed method's ability to detect selective changes in effective connectivity within a distributed network under cell-type-specific interventions and underscore how effective connectivities among regions may depend on the cell types activated. Formally, this paper offers a construct validation of optogenetic fMRI DCM by appealing to the known functional anatomy and synaptic circuitry of the basal ganglia-thalamocortical system.

Stochastic models were better than deterministic models across networks and stimulation groups. The greater model evidence exhibited by the stochastic models suggested that there were neuronal processes that cannot be explained strictly by the experimental stimulus. Stochastic modeling, which accounted for endogenous fluctuations, may therefore be optimal for future modeling studies and offer greater generalization across experiments, as it provides the best balance between accuracy and complexity for explaining the measured data (i.e., the greatest model evidence) (FIG. 20, panels A-D). The optimal degree of complexity for these endogenous fluctuations was also examined by fitting autoregressive models of increasing order. The results indicated that a relatively low order of local temporal correlations (e.g., AR(1) or AR(2) processes) was optimal across networks and stimulation groups (FIG. 20, panels E-H).

Replacement of the motor cortex with sensory cortex demonstrated a stability of the connectivity parameters within the basal ganglia-thalamocortical circuit. No significant differences were observed in the strength of inter-regional connectivity estimates when replacing MCX by SCX (FIG. 17, Table 5), and both network models yielded similar connections (FIG. 13, Table 3 and FIG. 15, Table 4). This property holds true in order for a causal estimation algorithm to be considered robust. It should be noted, however, that the selection of one model or the other did alter statistical effects across D1- and D2-MSN stimulations (FIG. 13, Table 3 and FIG. 15, Table 4). For example, the connection from thalamus to cortex was not statistically significant in the SCX network model during D2-MSN stimulations, leaving no pathway from the stimulation site to cortex and thus compromising the interpretation of causality within the basal ganglia-thalamocortical system (FIG. 14, panel D). In this respect, the MCX network model may offer more mechanistic insight than the SCX network model, as it exhibited causality between regions across the overall system, including connections from thalamus to cortex and from cortex to striatum during both perturbations (FIGS. 12 and 14). A causal relationship from thalamus to sensory cortex during D2-MSN stimulation was not detected, which may indicate that thalamus may directly influence motor—but not sensory—cortex during D2-MSN stimulations. This did not prevent the accurate prediction of observed responses with either network model. This may be due to the inclusion of endogenous fluctuations in the model equations, which were able to account for hidden neuronal responses that were not explicitly included in the network models.

The signs of significant connections during D1- and D2-MSN stimulations were consistent with the diversity of temporal profiles and polarities of fMRI responses. During D1-MSN stimulations, for example, the time series throughout the basal ganglia increased during stimulation. As expected, significant connectivity estimates throughout the basal ganglia-thalamocortical system were positive (FIG. 12; and FIG. 13, Table 3). While the initial drop in sensory cortex may be seen as an exception to this, the experimental model interpreted this transient as a reflection of a delay in cortical activations. During D2-MSN stimulations, connectivity estimates were positive all the way from CPu to cortex (FIG. 14; and FIG. 15, Table 4). However, the BOLD responses, especially in thalamus, generally decreased during stimulation. The feedforward aspect of the indirect pathway therefore did not explain the decreasing responses observed within STN, GPi, SN, and thalamus. Nevertheless, this issue might be resolved once the signal passes through the cortex. As shown in FIG. 14, the connection from cortex to STN was significantly negative, while the connections from STN to GPi, GPi to THL, and STN to SN were positive. Applying the multiplication operation along this pathway led to a negative response within the STN, GPi, SN, and THL and indicated that it may be the hyperdirect pathway, which was statistically significant and negative during D2-MSN stimulations, that explained the negative BOLD responses within these regions.

Beyond an understanding of normal basal ganglia information processing, the results offered insight into the mechanisms of movement disorders that originate from defects in this network. Optogenetically driving D2-MSNs, for example, simulated the loss of dopamine in striatum that is associated with Parkinson's disease (PD) by creating an imbalance in direct and indirect pathway activity. The connectivity analyses from D2-MSN stimulation revealed several features commonly observed in PD. First, systematically more negative self-connection parameters were observed within the basal ganglia's nuclei (STN, GPe, GPi, and SN) during D2-MSN stimulations compared to D1-MSN stimulations. Many of the self-connections exhibited a statistically significant or close-to-significant difference between D1- and D2-MSN stimulations for both the MCX and SCX network models (FIG. 19, Table 6). Based on the mathematical solution of the state equation (see Method Details, below), a more negative self-connection strength indicated that less time was needed to reach the activation state. One interpretation of this was that brain regions within the basal ganglia synchronized faster during D2-MSN stimulation. Increased synchrony and neural oscillations in the STN and GPi have been observed in primate and rodent models of PD. It has also been shown that STN activity correlates with downstream basal ganglia activity in PD monkeys. Although the causal link between STN oscillations and PD symptoms remain elusive it has been shown that pathological oscillations are suppressed by volitional movement, dopamine replacement therapy, and STN-DBS therapy. As another possible link to PD, statistically significant MCX-STN and close-to-significant SCX-STN connections during D2-, but not D1-MSN stimulations was observed. Cortical-STN interactions have been implicated in PD mechanisms. In some cases, the antiparkinsonian effects of STN stimulation result from selective activation of the M1-STN pathway.

Neurostimulation therapy for PD aims at modulating neuronal activity of the basal ganglia-thalamocortical system. Clinically, the most common brain regions targeted to treat PD motor symptoms with DBS are the STN and GPi. While the exact mechanism of action for DBS in PD remains unclear, many hypotheses have been proposed. For example, DBS may modulate abnormal synchronous oscillatory activity between the basal ganglia and cortical regions such as M1. As a therapeutic alternative, recent data have indicated that epidural chronic motor cortex stimulation (MCS) could also improve symptoms resulting from movement disorders like PD. Among the possible mechanisms of action for MCS, it is hypothesized to reduce synchronized oscillatory activities in basal ganglia nuclei, similar to STN stimulation. The connectivity analyses developed in the presently disclosed experiments may be used to elucidate the effectiveness of different regions as therapeutic targets. For example, the finding that motor cortex exhibits greater connectivity with subcortical structures during D2-MSN stimulation indicated that motor cortex modulation may restore balance to Parkinsonian circuitry and indicated that this region plays a significant role in the descending modulation of basal ganglia network activity.

There were distinct, approximately orthogonal patterns of significant and close-to-significant interregional connections between D1- and D2-MSN stimulations (Pearson's r=−0.0036 and −0.0165 for MCX and SCX network models, respectively). In distributed spatial representations, orthogonal arrangements of effective connectivity may be used to maximize discriminability. For example, they could be valuable in maintaining the separate identity and processing content of two populations with distinct cell types. In addition, orthogonal patterns can be employed to emit two independent sequences (e.g., a set of motor programs) simultaneously and to separate the received information afterward (e.g., within the cerebral cortex).

Methods of the present disclosure may be used to determine causal influences among brain regions driven by a specific cell type, which can be quantified and compared in the healthy and diseased brain by utilizing optogenetic fMRI and the network models disclosed herein. Knowing how neural pathways driven by specific cell populations contribute to diseases like PD will aid the development of treatments based on quantitative circuit mechanisms of disease, which will lead to improved targeted therapies with better efficacy and reduced adverse effects.

Method Details
Experimental Model and Subject Details
Mice

Bacterial artificial chromosome (BAC)-mediated transgenic mouse lines from the gene expression nervous system atlas (GENSAT) were used as subjects (male, 18-20 g, ~4 weeks old). Mice expressed Cre recombinase under control of either the dopamine D1 receptor (BAC-Cre Drd1a-262 mice, RRID: MMRRC_017264-UCD) or dopamine D2 receptor (BAC-Cre Drd2-44 mice, RRID: MMRRC_017263-UCD) regulatory elements. The double-floxed inverted (DIO) recombinant AAV1 virus AAV-EF1a-DIOhChR2(H134R)-EYFP was injected into the dorsomedial striatum (+0.48 mm AP, −1.50 mm ML, −3.00 mm DV), resulting in channelrhodopsin2 expression in either D1- or D2-expressing medium spiny neurons. Virus was acquired from the University of North Carolina vector core using Addgene plasmid #20298. Animals were housed individually following cannula implantation and provided with food and water ad libitum. All experimental procedures and animal husbandry were performed in strict accordance with the NIH, UCLA Institutional Animal Care and Use Committee (IACUC), and Stanford University IACUC guidelines. Animals were involved in behavioral rotation tests to confirm functional opsin expression prior to ofMRI experiments, but were otherwise naive and healthy. No randomization procedure was necessary for allocating animals to experimental groups, since the groups being compared (D1- and D2-MSN stimulation) were determined simply by the genetic strain of the animal (i.e., D1-Cre and D2-Cre). No procedures were used for sample size estimation.

Method Details
ofMRI Experiments fMRI scanning was performed using a 7 Tesla Bruker Biospec small animal MRI system. A single ofMRI scan included six 20 s pulse trains of optical stimulation delivered once per minute over 6 min. Photostimulation was delivered at 20 Hz with a 30% duty cycle via a 105 mm diameter optical fiber. The optical fiber, coupled to a 473 nm laser source (Laserglow Technologies, Toronto, ON), was calibrated to have a 2.5 mW output power. During fMRI scanning, animals were placed into the iso-center of the magnet while very lightly anesthetized with a calibrated vaporizer (Vet Equipment, Pleasanton, Calif., USA) using a mixture of $O_2$ (35%), $N_2O$ (65%), and isoflurane (0.4%-0.7%; Henry Schein, Melville, N.Y., USA). Body temperature was maintained at 36-38° C. using an airflow heater (SA Instrument, Stony Brook, N.Y., USA). Gradient recalled echo (GRE) BOLD methods were used to acquire fMRI images during photostimulation. The fMRI image acquisition was designed to have 25×25 $mm^2$ in-plane field of view (FOV) and 0.36×0.36×0.5 $mm^3$ spatial resolution with a sliding window reconstruction to update the image every repetition time (TR). The two-dimensional, multi-slice gradient-echo sequence used a four-interleave spiral readout, 750 ms TR, and 12 ms echo time, resulting in 23 coronal slices. The spiral k-space samples were reconstructed through a 2-dimensional gridding reconstruction method. Finally, real-time motion correction was performed using a custom-designed GPU-based system.

Precautions were taken during ofMRI experiments to avoid heating and visual-related artifacts. To ensure that visual-related artifacts were not generated, the eyes of each subject were carefully covered with black electrical tape. The connection between the fiber optic cable and the implanted cannula was also covered with black tape to prevent any leakage of light. Furthermore, to prevent heating, the stimulations were 2.5 mW with a 30% duty cycle. These numbers, taking into account the 105 mm diameter fibers employed, lead to a time-averaged light power density of 86.6 mW/mm$^2$. The time-averaged light-intensity range of 56-167 mW/mm$^2$ is far below the range that generated any artifact-derived responses. These data, in addition to the results indicating that optogenetic D1- and D2-MSN stimulations only led to positive local BOLD signals, demonstrated that heating confounds were not present in the current experiment.

ofMRI Data Processing

The motion-corrected images corresponding to individual scans of each animal were first aligned to a single, common coordinate frame using the NiftyReg toolbox. Next, the signal quality of each image was quantified by calculating the average coherence value at the site of stimulation using the mrVista software package (Vision Imaging Science and Technology Laboratory, Stanford University, CA) in MAT-LAB (MathWorks, Natick, Mass.). For each scanning session and animal, the best N motion-corrected images were averaged together, with N typically being 14 and no less than 10. Finally, slice-timing correction and image smoothing (4 mm FWHM Gaussian kernel) were performed using the Statistical Parametric Mapping toolbox (SPM12, Welcome Trust Centre for Neuroimaging, London, UK.

Time series were calculated for each voxel as the percent modulation of the BOLD signal relative to a 30 s baseline period collected prior to stimulation. After temporal detrending to correct for possible scanner drift and mean-correction, anatomical regions from a digital standard mouse brain atlas were used to segment the brain for region of interest (ROI)-specific analyses. Finally, time series were averaged over all voxels within each ROI.

Dynamic Causal Modeling

Dynamic causal modeling (DCM) models the brain as a dynamic system of interconnected regions during a series of specific perturbations or experimental tasks. Here, the perturbation was optical stimulation. Assuming that a single deterministic input defined by u(t) encoded the influence of optogenetic manipulation (i.e., a square function of zeros when the laser was OFF and ones when the laser was ON), and u(t) denoted stochastic region-dependent disturbances referred to as endogenous fluctuations, Equation 1 shows the state-space model of a generic DCM of ofMRI responses in the time domain:

$$\frac{dx(t)}{dt} = f(x(t), \theta_n, u(t)) = Ax(t) + Cu(t) + \omega(t), \quad \text{(Equation 1)}$$

$$y(t) = g(x(t), \theta_h) + \varepsilon(t)$$

where x(t) is the neuronal state, $\theta_n$=(A, C) are the neuronal parameters, A is a matrix of endogenous connection strengths, C is the strength of optogenetic input, $g(x(t),\theta_h)$ is a nonlinear operator that links the neuronal state x(t) to a predicted BOLD signal y(t) via changes in vasodilatation, blood flow, blood volume, and deoxyhemoglobin content, $\theta_h$ are the hemodynamic parameters, and $\varepsilon(t)$ is observation noise. In this study, the input function u(t) was specifically applied to the CPu network node, modeling the effect of in vivo optogenetic stimulation. Functions $f(x(t),\theta_n,u(t))$ and $g(x(t), \theta_h)$ are identical to those introduced by Friston et al.

Spectral DCM

Spectral DCMs were based on deterministic models that predicted cross-spectra from a biophysically plausible model of coupled endogenous fluctuations in a distributed neural system. Endogenous fluctuations and observation noise should be taken into account to formulate an appropriate brain network model. As such, the nature of the endogenous fluctuations (and observation noise) must be parameterized. In this study, we opted for autoregressive models of order one to four [i.e., AR(1) to AR(4) processes] that parameterized endogenous fluctuations u(t) and observation noise $\varepsilon(t)$ with amplitude and autoregressive coefficients as free parameters. This step was performed by modifying the function spm_csd_fmri_mtf.m in the SPM12 toolbox. After linearization of functions $f(x(t),\theta_n,u(t))$ and $g(x(t),\theta_n)$, Equation 1 can be rewritten in the frequency domain. Equation 2 shows the state-space model of a DCM of ofMRI responses in the frequency domain:

$$X(f) = \left(j2\pi f - \frac{df}{dx}\bigg|_{\theta_h,A}\right)^{-1}(CU(f) + \omega(f)), \quad \text{(Equation 2)}$$

$$Y(f) = \frac{dg}{dx}\bigg|_{\theta_h,A}\left(j2\pi f - \frac{df}{dx}\bigg|_{\theta_h,A}\right)^{-1}(CU(f) + \omega(f)) + \varepsilon(f)$$

As described above, spectral DCM predicted the cross-spectral density of the observed BOLD responses Y(f). Equation 3 shows the cross-spectral responses of a DCM for ofMRI:

$$Y(f)X(f)^* = \quad \text{(Equation 3)}$$

$$\left(\frac{dg}{dx}\bigg|_{\theta_h,A}\left(j2\pi f - \frac{df}{dx}\bigg|_{\theta_h,A}\right)^{-1}\right)(CG_u(f)C^T + G_{\omega,h}(f))$$

$$\left(\frac{dg}{dx}\bigg|_{\theta_h,A}\left(j2\pi f - \frac{df}{dx}\bigg|_{\theta_h,A}\right)^{-1}\right)^* + G_{\varepsilon,n}(f)$$

where $$G_u(f) = PSD\{u(t)\}, \; G_{\omega,n}(f) = (\sigma^2_{\omega,n}/|1 - \Sigma_n AR_{\omega,n}e^{-j2\pi fn}|^2),$$

$$\text{and} \; G_{\varepsilon,n}(f) = (\sigma^2_{\varepsilon,n}/|1 - \Sigma_n AR_{\varepsilon,n}e^{-j2\pi fn}|^2).$$

Here, $G_u(f)$ was the power spectral density of the experimental input, $G_{\omega,n}(f)$ was the spectral density of endogenous fluctuations parameterized as autoregressive processes of order n, and $G_{\varepsilon,n}(f)$ was the spectral density of the observation noise also parameterized as autoregressive processes of order n. These terms were the same as those introduced by Friston et al., but with $G_{\omega,n}(f)$ and $G_{\varepsilon,n}(f)$ parameterized as autoregressive processes. $\sigma^2_{\omega,n}$ and $\sigma^2_{\varepsilon,n}$ were the variances of their corresponding autoregressive processes of order n, and $AR_{\omega,n}$ and $AR_{\varepsilon,n}$ were their corresponding autoregressive coefficients. With this mathematical formulation, endogenous fluctuations can be included via the $G_{\omega,n}(f)$ term (stochastic modeling) or excluded (deterministic modeling). To do so, the function spm_csd_fmri_mtf.m was modified in SPM12. Finally, by rearranging terms, Equation 3 can be rewritten by expressing $$S(f) = \frac{dg}{dx}\Big|_{\theta_h,A} \left(j2\pi f - \frac{df}{dx}\Big|_{\theta_h,A}\right)^{-1}$$

as the transfer function, and $$G_{\varepsilon,n}(f) = CG_u(f)C^T + G_{\omega,n}(f)($$

as the input function.

Equation 4 shows the simplified version of the cross-spectral responses of a DCM for ofMRI:

$$G_y(f) = Y(f)Y(f)^* = S(f)G_{\varepsilon,n}(f)S(f)^* + G_{\omega,n}(f) \quad \text{(Equation 4)}$$

Experimental Design

D1- and D2-MSN stimulation experiments were performed in randomized order. The researcher implementing the models was not blinded to the experimental group of individual subjects. No procedures were used for sample-size estimation.

Quantification and Statistical Analysis

Computing Effective Connectivity Estimates

Generative models were estimated after low-pass filtering raw time series to avoid over-fitting of the data. For each of the four network models, appropriate cutoff frequencies were estimated region-by-region by fitting the averaged time series across subjects and calculating the frequency at which the first derivative of the AR(1) process was equal to or less than $4 \times 10^{-5}$. During D1-MSN stimulation, across regions, a mean cutoff frequency of 0.2489 Hz and a 95% confidence interval of 0.2137 to 0.2841 Hz was obtained for the MCX network, and a mean cutoff frequency of 0.2533 Hz and a 95% confidence interval of 0.2209 to 0.2858 Hz was obtained for the SCX network. During D2-MSN stimulation, a mean cutoff frequency of 0.2623 Hz and a 95% confidence interval of 0.2241 to 0.3004 Hz for the MCX network was obtained, and a mean cutoff frequency of 0.2563 and a 95% confidence interval of 0.2105 to 0.3022 Hz was obtained. Therefore, generative models were evaluated using cutoff frequencies from 0.21 to 0.30 Hz with a step size of 0.01 Hz, and distributions of connectivity estimates and p values from these 10 cutoff frequencies were generated. The optimal cutoff frequency was selected as the one which maximized the discriminability of the p values (in accord with the Matched Filter theorem). Specifically, the cutoff that maximized the weighted sum of the number of significant and close-to-significant connections (weights of 1.0 and 0.5, respectively) was selected. These were 0.29 and 0.24 Hz for the MCX and SCX networks during D1-MSN stimulation, respectively, and 0.27 and 0.22 Hz for MCX and SCX networks during D2-MSN stimulation, respectively.

Using the cross-spectral responses described in Equation 4, network models were inverted (i.e., the network parameters were estimated) by minimizing variational free energy under the Laplace approximation. In particular, an estimate of the negative free energy was used as an approximation of the log model evidence. This step was performed by invoking the function spm_nlsi_GN.m in SPM12. To select the optimal modeling approach (i.e., stochastic or deterministic) and the optimal order of autoregressive processes within the winning approach, Bayesian model selection (BMS) was used and a random effects BMS scheme at the group level that accounted for potential heterogeneity across subjects was used.

First, the two families of models were compared: stochastic and deterministic, each family including autoregressive models of order one to four. To do so, Bayesian model selection was first used to calculate the exceedance probabilities of stochastic and deterministic families. This step was performed for each of the seven low-pass filter cutoff frequencies using the function spm_run_bms_dcm.m in SPM12. After finding that stochastic modeling was optimal across cutoff frequencies for each stimulation and network of interest (FIG. 20, panels A-D), Bayesian model was used comparison to determine the autoregressive model order that provided the greatest negative free energy (i.e., model evidence) under stochastic assumptions. The reason for testing AR processes of different order was to explore whether increasing the complexity of the models (i.e., the number of free parameters) minimized free energy. Analyses did not reveal one winning model but a subset of models having comparable exceedance probabilities. With D1-MSN stimulations, AR(1) processes were optimal in both network cases, while with D2-MSN stimulations, AR(2) processes were superior in the MCX model and AR(1) processes were optimal in the SCX case (FIG. 20, panels E-H). Because a clear winning model was not obtained for either optogenetic manipulation, Bayesian model averaging (BMA) was used to compute reliable parameter estimates and account for model uncertainty. This computation was done by invoking the function spm_run_bms_dcm.m in SPM12. BMA averaged network estimates over generative models (e.g., autoregressive processes) by weighting parameter estimates by their corresponding model posterior probabilities.

Before BMA, winning models were checked for at the subject level to identify possible outliers. A subject within the D2-MSN stimulation group exhibited a winning model of AR(3) with exceedance probability equal to 1.00. To confirm the existence of this outlier, after BMA, Euclidean distances were computed as a measure of (dis)similarity among group mean estimates and individual estimates across subjects of the same type of stimulation. It was observed that the Euclidean distance computed for this subject did not lie within the confidence intervals defined by the distribution of mean Euclidean distances of the D2-MSN stimulation group and excluded the subject from subsequent analyses.

Statistics

Finally, following BMA, the resulting connectivity estimate means from the averaged stochastic models were used for examining statistical significances in D1- and D2-MSN stimulations at the between subject level in the usual way (using classical t tests; see below for assessment of statistical test assumptions). The resulting network parameters estimated at each cutoff frequency were used to determine statistical significance within and between optogenetic stimulations. The statistical significance of connectivity strengths within the same stimulation at each cutoff frequency was assessed by a one-sample t test, and 95% confidence intervals were computed across cutoff frequencies. Likewise, statistical differences between MCX and SCX networks, and between D1- and D2-MSN stimulation networks, at each cutoff frequency were assessed by a two-sample t test and 95% confidence intervals were computed across cutoff frequencies. False discovery rate (FDR) was then used to correct for multiple testing, with the number of tests being equal to the number of a priori network connections, i.e., 24 connections/tests as illustrated in FIG. 10, panel B. Exact p values for statistical tests are reported in FIG. 13, Table 3; FIG. 15, Table 4; FIG. 17, Table 5; and FIG. 19, Table 6. For all reported modeling results (FIGS. 12, 14, 16, 18, 11, and 20; and FIG. 13, Table 3; FIG. 15, Table 4; FIG. 17, Table 5; and FIG. 19, Table 6), the numbers of subjects used for statistical testing were n=12 for D1-MSN stimulation and n=10 for D2-MSN stimulation. As explained in the previous section, one subject from the D2-MSN stimulation group had been excluded as an outlier. The time series presented in FIG. 9 represent the average of the 11 subjects originally scanned during D2-MSN stimulation (i.e., including the outlier).

We tested for normality in our connectivity estimates using the Lilliefors test (as implemented in MATLAB). More specifically, we tested for Gaussianity in the 24 connectivity estimates calculated in each of the 2 optogenetic stimulations, the 2 networks of interest, and the 10 cutoff frequencies, giving a total of 960 statistical tests. In the majority of tests (88%), the null hypothesis that connectivity estimates were normally distributed was not rejected (uncorrected $p>0.05$). Thus, we opted for parametric tests (classical t tests) for examining statistical significances within and between groups.

While the present disclosure has been described with reference to the specific embodiments thereof, it should be understood by those skilled in the art that various changes may be made and equivalents may be substituted without departing from the true spirit and scope of the present disclosure. In addition, many modifications may be made to adapt a particular situation, material, composition of matter, process, process step or steps, to the objective, spirit and scope of the present disclosure. All such modifications are intended to be within the scope of the claims appended hereto.

What is claimed is:

1. A method comprising:
   obtaining functional activity data for a region of a brain of a first individual, wherein the functional activity data represent a collective activity of a plurality of neurons in the region; and
   estimating relative activities of neural pathways regulated by each of a plurality of neuronal subtypes by computationally processing the functional activity data, wherein the computational processing comprises:
   i) generating a connectivity model from the functional activity data based on a network model of functional connections among interconnected nodes representing the region, wherein the interconnected nodes comprise a node corresponding to each of the plurality of neuronal subtypes; and
   ii) deriving a set of coefficients from a linear regression between a) the connectivity model; and b) neuronal subtype-specific connectivity estimates among the interconnected nodes,
   wherein the set of coefficients of the regression represent the contribution to the functional activity data of a neural pathway regulated by each of the plurality of distinct neuronal subtypes, wherein each of the neuronal subtypes comprise neurons categorized by neuronal identity and the neuronal identity comprises expression of neuronal subtype-specific marker and/or neuronal subtype-specific spatial location.

2. The method of claim 1, wherein the functional activity data is resting-state functional activity data.

3. The method of claim 1, wherein the functional activity data is obtained by functional magnetic resonance imaging (fMRI), magentoencephalography (MEG), and/or electroencephalography (EEG).

4. The method of claim 1, wherein the obtaining comprises measuring functional activity of the region using fMRI, MEG, and/or EEG, to obtain the functional activity data.

5. The method of claim 1, wherein the region of the brain comprises the thalamus, cortex, ventral tegmental area (VTA), prefontal cortex (PFC), nucleus accumbens (NAc), amygdala (BLA), substantia nigra (SN), ventral pallidum, globus pallidus, dorsal striatum, ventral striatum, subthalamic nucleus (STN), anterior caudate putamen (CPu), globus pallidus external (GPe), globus pallidus internal (GPi), hippocampus, dentate gyrus, cingulate gyrus, entorhinal cortex, olfactory cortex, motor cortex, or cerebellum, or combinations thereof.

6. The method of claim 1, wherein the neuronal subtypes comprise dopaminergic, cholinergic, gamma-aminobutyric acid-(GABA)ergic, glutamatergic, or peptidergic neurons.

7. The method of claim 1, wherein the neuronal subtype-specific connectivity estimate is derived from a different species of organism than the species of organism to which the first individual belongs.

8. The method of claim 1, wherein the first individual is a human individual.

9. The method of claim 1, wherein the first individual is a healthy individual.

10. The method of claim 1, wherein the first individual has a neurological disorder.

11. The method of claim 10, wherein the neurological disorder is a neurological disease, or an age-related neurological disorder.

12. The method of claim 11, wherein the neurological disease is Parkinson's disease, Alzheimer's disease, dementia, epilepsy, autism, bipolar disorder, schizophrenia, Tourette's syndrome, obsessive compulsive disorder, attention deficit hyperactivity disorder, Huntington's disease, multiple sclerosis, or migraine.

13. A method of identifying a neural circuit-level biomarker associated with a neurological disorder, comprising:
   i) estimating relative activities of neural pathways regulated by each of a plurality of neuronal subtypes by performing the method of claim 1 in each first individual of a plurality of groups of first individuals, the plurality of groups comprising:
   a case group of first individuals having the neurological disorder; and a control group of first individuals, thereby generating a plurality of sets of regression coefficients comprising:
   a case set of regression coefficients representing the contribution to a case functional activity data of the neural pathway regulated by each of the plurality of distinct neuronal subtypes in the case group; and
   a control set of regression coefficients representing the contribution to a control functional activity data of the neural pathway regulated by each of the plurality of distinct neuronal subtypes in the control group;
   ii) calculating a difference measurement between the case set and the control set of regression coefficients; and
   iii) determining that the case set of regression coefficients is a neural circuit-level biomarker associated with the neurological disorder when the difference measurement for one or more regression coefficients meets a threshold criterion, or determining that the case set of regression coefficients is not a neural circuit-level biomarker associated with the neurological disorder when the difference measurement for one or more regression coefficients does not meet the threshold criterion.

14. The method of claim 13, wherein the control group comprises individuals not having the neurological disorder.

15. The method of claim 13, wherein the case group comprises individuals having a neurological disorder and to whom a treatment for the neurological disorder has been administered, and the control group comprises individuals having a neurological disorder and to whom a treatment for the neurological disorder has not been administered.

16. The method of claim 13, wherein the neurological disorder is a neurological disease, or an age-related neurological disorder.

17. The method of claim 16, wherein the neurological disease is Parkinson's disease, Alzheimer's disease, dementia, epilepsy, autism, bipolar disorder, schizophrenia, Tourette's syndrome, obsessive compulsive disorder, attention deficit hyperactivity disorder, Huntington's disease, multiple sclerosis, or migraine.

18. A method of treating an individual for a neurological disease, the method comprising:
   i) estimating relative activities of neural pathways regulated by each of a plurality of neuronal subtypes in a brain of a first individual by performing the method of claim 1, wherein the first individual has a neurological disorder;
   ii) stimulating a region of the brain in a manner sufficient to modulate the activity of neurons of one or more of the plurality of neuronal subtypes based on the estimated relative activities.

19. A system, comprising:
   a magnetic resonance imaging (MRI) device,
   a processor; and
      a non-transient computer-readable medium comprising instructions that, when executed by the processor, cause:
         the MRI device to record a functional activity of a brain of an individual, thereby generating functional activity data for a region of the brain; and
         the processor to perform the method of claim 1 using the generated functional activity data.

20. The system of claim 19, further comprising a deep brain stimulation device, or a transcranial magnetic stimulation device.

21. The system of claim 19, further comprising a user interface and a data connector that transmits data from the processor to the user interface.

22. A method comprising:
   obtaining functional activity data for a region of a brain of a first individual, wherein the functional activity data represent a collective activity of a plurality of neurons in the region; and
   estimating relative activities of neural pathways regulated by each of a plurality of neuronal subtypes by computationally processing the functional activity data, wherein the computational processing comprises:
      i) generating a connectivity model from the functional activity data based on a network model of functional connections among interconnected nodes representing the region, wherein the interconnected nodes comprise a node corresponding to each of the plurality of neuronal subtypes; and
      ii) deriving a set of coefficients from a linear regression between a) the connectivity model; and b) neuronal subtype-specific connectivity estimates among the interconnected nodes,
   wherein the set of coefficients of the regression represent the contribution to the functional activity data of a neural pathway regulated by each of the plurality of distinct neuronal subtypes, wherein each of the neuronal subtypes comprise neurons categorized by activity pattern.

23. The method of claim 22, wherein the activity pattern comprises neuronal subtype-specific frequency, duration, and/or magnitude of activity.

24. A method comprising:
   obtaining functional activity data for a region of a brain of a first individual, wherein the functional activity data represent a collective activity of a plurality of neurons in the region; and
   estimating relative activities of neural pathways regulated by each of a plurality of neuronal subtypes by computationally processing the functional activity data, wherein the computational processing comprises:
      i) generating a connectivity model from the functional activity data based on a network model of functional connections among interconnected nodes representing the region, wherein the interconnected nodes comprise a node corresponding to each of the plurality of neuronal subtypes; and
      ii) deriving a set of coefficients from a linear regression between a) the connectivity model; and b) neuronal subtype-specific connectivity estimates among the interconnected nodes,
   wherein the set of coefficients of the regression represent the contribution to the functional activity data of a neural pathway regulated by each of the plurality of distinct neuronal subtypes, wherein the generating comprises using dynamic causal modeling (DCM) to generate a DCM connectivity model.

25. The method of claim 24, wherein the DCM is spectral DCM (spDCM).

26. The method of claim 25, wherein the spDCM comprises stochastic modeling.

27. A method comprising:
   obtaining functional activity data for a region of a brain of a first individual, wherein the functional activity data represent a collective activity of a plurality of neurons in the region; and
   estimating relative activities of neural pathways regulated by each of a plurality of neuronal subtypes by computationally processing the functional activity data, wherein the computational processing comprises:
      i) generating a connectivity model from the functional activity data based on a network model of functional connections among interconnected nodes representing the region, wherein the interconnected nodes comprise a node corresponding to each of the plurality of neuronal subtypes; and
      ii) deriving a set of coefficients from a linear regression between a) the connectivity model; and b) neuronal subtype-specific connectivity estimates among the interconnected nodes,
   wherein the set of coefficients of the regression represent the contribution to the functional activity data of a neural pathway regulated by each of the plurality of distinct neuronal subtypes, wherein the generating comprises using neural mass modeling (NMM).

28. A method comprising:
   obtaining functional activity data for a region of a brain of a first individual, wherein the functional activity data represent a collective activity of a plurality of neurons in the region; and estimating relative activities of neural pathways regulated by each of a plurality of neuronal subtypes by computationally processing the functional activity data, wherein the computational processing comprises:
i) generating a connectivity model from the functional activity data based on a network model of functional connections among interconnected nodes representing the region, wherein the interconnected nodes comprise a node corresponding to each of the plurality of neuronal subtypes; and
ii) deriving a set of coefficients from a linear regression between a) the connectivity model; and b) neuronal subtype-specific connectivity estimates among the interconnected nodes,
wherein the set of coefficients of the regression represent the contribution to the functional activity data of a neural pathway regulated by each of the plurality of distinct neuronal subtypes, wherein the deriving comprises using a general linear model, linear least squares regression, robust linear regression, support vector machine, quadratic programming, or ridge regression.

29. A method comprising:
obtaining functional activity data for a region of a brain of a first individual, wherein the functional activity data represent a collective activity of a plurality of neurons in the region; and
estimating relative activities of neural pathways regulated by each of a plurality of neuronal subtypes by computationally processing the functional activity data, wherein the computational processing comprises:
i) generating a connectivity model from the functional activity data based on a network model of functional connections among interconnected nodes representing the region, wherein the interconnected nodes comprise a node corresponding to each of the plurality of neuronal subtypes; and
ii) deriving a set of coefficients from a linear regression between a) the connectivity model; and b) neuronal subtype-specific connectivity estimates among the interconnected nodes,
wherein the set of coefficients of the regression represent the contribution to the functional activity data of a neural pathway regulated by each of the plurality of distinct neuronal subtypes, wherein the neuronal subtypes comprise neurons of the thalamus, cortex, ventral tegmental area (VTA), prefontal cortex (PFC), nucleus accumbens (NAc), amygdala (BLA), substantia nigra (SN), ventral pallidum, globus pallidus, striatum, dorsal striatum, ventral striatum, subthalamic nucleus (STN), anterior caudate putamen (CPu), globus pallidus external (GPe), globus pallidus internal (GPi), hippocampus, dentate gyrus, cingulate gyrus, entorhinal cortex, olfactory cortex, motor cortex, or cerebellum.

30. The method of claim 29, wherein the neuronal subtypes comprise medium spmy neurons.

31. A method comprising:
obtaining functional activity data for a region of a brain of a first individual, wherein the functional activity data represent a collective activity of a plurality of neurons in the region; and
estimating relative activities of neural pathways regulated by each of a plurality of neuronal subtypes by computationally processing the functional activity data, wherein the computational processing comprises:
i) generating a connectivity model from the functional activity data based on a network model of functional connections among interconnected nodes representing the region, wherein the interconnected nodes comprise a node corresponding to each of the plurality of neuronal subtypes; and
ii) deriving a set of coefficients from a linear regression between a) the connectivity model; and b) neuronal subtype-specific connectivity estimates among the interconnected nodes,
wherein the set of coefficients of the regression represent the contribution to the functional activity data of a neural pathway regulated by each of the plurality of distinct neuronal subtypes, wherein the neuronal subtypes comprise neurons expressing dopamine receptor subtypes, metabotropic glutamate receptor subtypes, ionotropic glutamate receptor subtypes, metabotropic acetylcholine receptor subtypes, ionotropic acetylcholine receptor subtypes, GABAA receptor subtypes, or GABAB receptor subtypes.

32. A method comprising:
obtaining functional activity data for a region of a brain of a first individual, wherein the functional activity data represent a collective activity of a plurality of neurons in the region; and
estimating relative activities of neural pathways regulated by each of a plurality of neuronal subtypes by computationally processing the functional activity data, wherein the computational processing comprises:
i) generating a connectivity model from the functional activity data based on a network model of functional connections among interconnected nodes representing the region, wherein the interconnected nodes comprise a node corresponding to each of the plurality of neuronal subtypes; and
ii) deriving a set of coefficients from a linear regression between a) the connectivity model; and b) neuronal subtype-specific connectivity estimates among the interconnected nodes,
wherein the set of coefficients of the regression represent the contribution to the functional activity data of a neural pathway regulated by each of the plurality of distinct neuronal subtypes, wherein the estimating further comprises: iii) generating the neuronal subtype-specific connectivity estimates before the deriving (ii).

33. The method of claim 32, wherein generating the neuronal subtype-specific connectivity estimates comprises, for each neuronal subtype:
obtaining neuronal subtype functional activity data for the region of a brain of one or more second individuals, wherein the region of the brain of the one or more second individuals corresponds to the region of the brain of the first individual, and wherein the functional activity data represent a collective activity of a plurality of neurons in the region of the brain of the one or more second individuals caused by selective activity modulation of neurons of the neuronal subtype in the brain of the one or more second individuals;
generating, for each of the plurality of neuronal subtypes, a neuronal subtype-specific connectivity model from the neuronal subtype functional activity data based on the network model; and
estimating the connectivity among the interconnected nodes of the network model for each of the plurality of neuronal subtypes based on an average across the one or more second individuals of the neuronal subtype-specific connectivity model.

34. The method of claim 33, wherein the neuronal subtype functional activity data is obtained by functional magnetic resonance imaging (fMRI), magentoencephalography (MEG), and/or electroencephalography (EEG).

35. The method of claim 34, wherein obtaining the neuronal subtype functional activity data comprises measuring functional activity of the region using fMRI, MEG, and/or EEG, to obtaining the neuronal subtype functional activity data.

36. The method of claim 33, wherein neurons of the neuronal subtype in the one or more second individuals selectively express a light-activated polypeptide configured to modulate the activity of the neurons when the neurons are illuminated by an activating light stimulus.

37. The method of claim 36, wherein the obtaining comprises, for each of the plurality of neuronal subtypes in the one or more second individuals:
   illuminating neurons of the neuronal subtype with an activating light stimulus; and measuring functional activity of the region, thereby generating the neuronal subtype functional activity data.

38. The method of claim 33, wherein generating the neuronal subtype-specific connectivity model comprises using dynamic causal modeling (DCM) to generate a neuronal subtype-specific DCM connectivity model.

39. The method of claim 38, wherein the DCM is spectral DCM (spDCM).

40. The method of claim 39, wherein the spDCM comprises stochastic modeling.

\* \* \* \* \*